(12) United States Patent
Sasaki et al.

(10) Patent No.: US 10,881,649 B2
(45) Date of Patent: Jan. 5, 2021

(54) THERAPEUTIC AGENT OR PREVENTIVE AGENT FOR ALOPECIA AREATA

(71) Applicant: Toray Industries, Inc., Tokyo (JP)

(72) Inventors: Rie Sasaki, Kamakura (JP); Shinnosuke Hayashi, Kamakura (JP); Martial Vallet, Ehime (JP); Shinya Yokosaka, Kamakura (JP); Kazuya Osumi, Kamakura (JP); Takumi Aoki, Tokyo (JP); Hiroyuki Meguro, Kamakura (JP); Mie Kaino, Kamakura (JP); Kozue Takagaki, Kamakura (JP); Takehiro Takahashi, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 16/633,956

(22) PCT Filed: Jul. 27, 2018

(86) PCT No.: PCT/JP2018/028277
§ 371 (c)(1),
(2) Date: Jan. 24, 2020

(87) PCT Pub. No.: WO2019/022235
PCT Pub. Date: Jan. 31, 2019

(65) Prior Publication Data
US 2020/0215046 A1    Jul. 9, 2020

(30) Foreign Application Priority Data
Jul. 27, 2017    (JP) .................................. 2017-145442

(51) Int. Cl.
| | | |
|---|---|---|
| A61K 31/445 | (2006.01) | |
| A61K 31/451 | (2006.01) | |
| A61P 17/14  | (2006.01) | |
| A61K 31/4525 | (2006.01) | |
| A61K 31/454 | (2006.01) | |

(52) U.S. Cl.
CPC .......... *A61K 31/451* (2013.01); *A61K 31/454* (2013.01); *A61K 31/4525* (2013.01); *A61P 17/14* (2018.01)

(58) Field of Classification Search
CPC .............................. A61K 31/445; A61P 17/14
USPC ....................................................... 514/330
See application file for complete search history.

(56) References Cited

U.S. PATENT DOCUMENTS

| | | |
|---|---|---|
| 2012/0322837 A1 | 12/2012 | Maeba et al. |
| 2015/0065507 A1 | 3/2015  | Birault et al. |
| 2015/0175562 A1 | 6/2015  | Gege et al. |
| 2018/0370916 A1 | 12/2018 | Hayashi et al. |

FOREIGN PATENT DOCUMENTS

| | | |
|---|---|---|
| JP | 2012-236822 A | 12/2012 |
| JP | 2015-514794 A | 5/2015 |
| JP | 2015-521193 A | 7/2015 |
| WO | 2010/007046 A2 | 1/2010 |
| WO | 2010/096371 A2 | 8/2010 |
| WO | 2012/027965 A1 | 3/2012 |
| WO | 2015/103507 A1 | 7/2015 |
| WO | 2015/103508 A1 | 7/2015 |
| WO | 2017/131156 A1 | 8/2017 |

OTHER PUBLICATIONS

Hordinsky, M. K., "Overview of Alopecia Areata," *Journal of Investigative Dermatology Symposium Proceedings*, 2013, vol. 16, Issue 1, pp. S13-S15.

Hordinsky, M. K., "Current Treatments for Alopecia Areata," *Journal of Investigative Dermatology Symposium Proceedings*, 2015, vol. 17, Issue 2, pp. 44-46.

Ivanov, I. I. et al., "The Orphan Nuclear Receptor RORγt Directs the Differentiation Program of Proinflammatoly IL-17⁺ T Helper Cells," *Cell*, 2006, vol. 126, pp. 1121-1133.

Jetten, A. M., "Retinoid-related orphan receptors (RORs): critical roles in development, immunity, circadian rhythm, and cellular metabolism," *Nuclear Receptor Signaling*, 2009, vol. 7, e003, pp. 1-32.

Solt, L. A. et al., "Suppression of $T_H17$ differentiation and autoimmunity by a synthetic ROR ligand," *Nature*, 2011, vol. 472, pp. 491-494.

Xing, L. et al. "Alopecia areata is driven by cytotoxic T lymphocytes and is reversed by JAK inhibition," *Nature Medicine*, 2014, No. 20, pp. 1043-1049.

(Continued)

*Primary Examiner* — Charanjit Aulakh
(74) *Attorney, Agent, or Firm* — DLA Piper LLP (US)

(57) ABSTRACT

A therapeutic agent or a preventive agent for alopecia areata has an RORγ antagonistic activity, and, there is a therapeutic agent or a preventive agent for alopecia areata, including a cyclic amine derivative typified by the following compound or a pharmacologically acceptable salt thereof as an active ingredient.

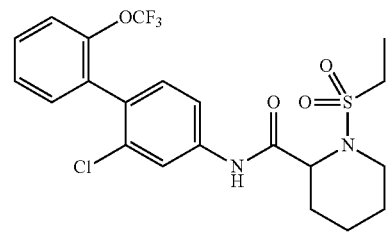

8 Claims, 2 Drawing Sheets

(56) References Cited

OTHER PUBLICATIONS

Mackay-Wiggan, J. et al. "Oral ruxolitinib induces hair regrowth in patients with moderate-to-severe alopecia areata," *Journal of Clinical Investigation Insight*, 2016, No. 22, e89790, pp. 1-9.
Fauber, B. P. et al., "Discovery of 1-{4-[3-Fluoro-4-((3S,6R)-3-methyl-1,1-dioxo-6-phenyl-[1,2]thiazinan-2-ylmethyl)-phenyl]-piperazin-l-yl}-ethanone (GNE-3500): a Potent, Selective, and Orally Bioavailable Retinoic Acid Receptor-Related Orphan Receptor C (RORc or RORγ) Inverse Agonist," *Journal of Medicinal Chemistry*, 2015, vol. 58, pp. 5308-5322, Abstract only.

THERAPEUTIC AGENT OR PREVENTIVE AGENT FOR ALOPECIA AREATA

TECHNICAL FIELD

This disclosure relates to a therapeutic agent or a preventive agent for alopecia areata.

BACKGROUND

Alopecia areata is a disease which develops as a result of temporary impairment of hair matrix cells due to some kind of cause; which lacks prodromal symptoms or subjective symptoms; and in which well-defined patches of hair loss appear suddenly. According to the severity, alopecia areata is classified into ophiasis in which hair loss occurs in the hairlines in the occipital to temporal regions of the head, alopecia totalis in which the entire scalp hair is lost due to fusion of patches of hair loss, and alopecia universalis in which not only the scalp hair but also the hair of the whole body are lost (Hordinsky et al., Journal of Investigative Dermatology Symposium Proceedings, 2013, Vol. 16, p. S13-S15).

As treatment of alopecia areata, mainly oral administration or external use of steroids, as well as carpronium chloride, DNCB sensitization therapy, and PUVA therapy and the like have been used (Hordinsky et al., Journal of Investigative Dermatology Symposium, 2015, Vol. 17, p. 44-46).

Meanwhile, recently, it became clear that retinoid-related orphan receptor γ (hereinafter referred to as RORγ), which is a nuclear receptor, functions as a transcription factor essential for the differentiation and proliferation of Th17 cells and the expression of IL-17 (Ivanov et al., Cell, 2006, Vol. 126, p. 1121-1133), and it was shown that suppression of the expression or function of RORγ results in suppression of the differentiation and activation of Th17 cells and the production of IL-17 (Jetten, Nuclear Receptor Signaling, 2009, Vol. 7, e003).

As an RORγ antagonist, N-(5-(N-(4-(1,1,1,3,3,3-hexafluoro-2-hydroxypropan-2-yl)phenyl)sulfamoyl)-4-methylthiazol-2-yl)acetamide (Solt et al., Nature, 2011, Vol. 472, p. 491-494), substituted azole derivatives (JP 2012-236822 A) such as 6-(2-chloro-4-methylphenyl)-3-(4-cyclopropyl-5-(3-neopentylcyclobutyl)isoxazol-3-yl)-5-oxohexanoic acid, and sulfonylbenzene derivatives (WO 2012/027965 A) such as N-(5-(2-chlorobenzoyl)-4-(3-chlorophenyl)thiazol-2-yl)-2-(4-(ethylsulfonyl)phenyl)acetamide, have been reported previously, but compounds having a cyclic amine structure such as 1-substituted piperidine-2-carboxamide, have not been disclosed.

As the compound having a cyclic amine structure such as 1-substituted piperidine-2-carboxamide, (S)-1-(2-(3,3-difluoropyrrolidin-1-yl)acetyl)-N-(1-ethyl-5-phenyl-1H-1,2,4-triazol-3-yl)piperidine-2-carboxamide and the like has been reported as a cannabinoid 2 receptor agonist (WO 2010/096371 A), and (R)—N-(5-benzyl-4-phenylthiazol-2-yl)-1-(2-cyclopentylacetyl)piperidine-2-carboxamide and the like has been reported as an acyl-coenzyme A: diacylglycerol acyltransferase 1 inhibitor (WO 2010/007046 A), but the effects on RORγ and therapeutic effects or preventive effects on alopecia areata of these compounds are neither disclosed nor suggested.

However, alopecia areata often accompanies emotional distress due to cosmetic problems, and various preventive agents or therapeutic agents for alopecia areata have been studied, but no drugs that meet satisfaction in terms of their effects and safety have been found. At present, even with steroids, which have been mainly used for treatment of alopecia areata, their effects are limited, or almost no effects are expected. The current situation is that there are many clinical cases in which administration must be discontinued before sufficient drug efficacy is observed due to concerns about serious side effects such as infection. Therefore, it is desired to develop a novel therapeutic agent or preventive agent for alopecia areata in which these problems were solved or improved.

Hence, it could be helpful to provide a therapeutic agent or a preventive agent for alopecia areata, having an RORγ antagonistic activity.

SUMMARY

We found that a novel cyclic amine derivative having an RORγ antagonistic activity or a pharmacologically acceptable salt thereof is effective for treatment or prevention of alopecia areata.

We thus provide a therapeutic agent or a preventive agent for alopecia areata, containing a cyclic amine derivative represented by general formula (I) or a pharmacologically acceptable salt thereof as an active ingredient:

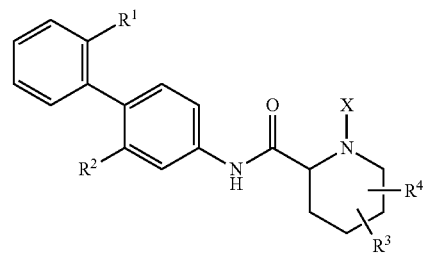

wherein
$R^1$ represents an alkyloxy group having 1 to 3 carbon atoms, any 1 to 3 hydrogen atoms of which are optionally substituted with a halogen atom(s),
$R^2$ represents a halogen atom,
$R^3$ represents a hydrogen atom, a halogen atom, or a hydroxy group,
$R^4$ represents a hydrogen atom or a halogen atom,
X represents —C(=O)—(CH$_2$)$_n$—R$^5$ or —S(=O)$_2$—R$^6$,
n represents an integer of 0 to 5,
$R^5$ represents a hydrogen atom, —OR$^7$, —SR$^7$, —S(=O)$_2$—R$^7$, —C(=O)—OR$^7$, —N(R$^7$)R$^8$, an alkyl group having 1 to 3 carbon atoms, any 1 to 3 hydrogen atoms of which are optionally substituted with a halogen atom(s), or a heteroaryl group, any hydrogen atom(s) of which is/are optionally substituted with an alkyl group(s) having 1 to 3 carbon atoms,
$R^6$ represents an alkyl group having 1 to 5 carbon atoms,
$R^7$ represents a hydrogen atom or an alkyl group having 1 to 3 carbon atoms, any 1 to 3 hydrogen atoms of which are optionally substituted with a halogen atom(s), and
$R^8$ represents a hydrogen atom, an alkyl group having 1 to 3 carbon atoms, an acyl group having 2 to 4 carbon atoms, or an alkylsulfonyl group having 1 to 3 carbon atoms.

In the cyclic amine derivative represented by general formula (I), it is preferable that $R^1$ is an alkyloxy group having 1 to 3 carbon atoms, any 1 to 3 hydrogen atoms of which are optionally substituted with a fluorine atom(s) or a chlorine atom(s), $R^2$ is a fluorine atom or a chlorine atom, $R^3$ is a hydrogen atom, a fluorine atom, a chlorine atom, or a hydroxy group, $R^4$ is a hydrogen atom, a fluorine atom, or a chlorine atom, $R^5$ is a hydrogen atom, —$OR^7$, —$SR^7$, —$S(=O)_2$—$R^7$, —$C(=O)$—$OR^7$, —$N(R^7)R^8$, an alkyl group having 1 to 3 carbon atoms, any 1 to 3 hydrogen atoms of which are optionally substituted with a fluorine atom(s) or a chlorine atom(s), or a heteroaryl group, any hydrogen atom(s) of which is/are optionally substituted with a methyl group(s), $R^6$ is an alkyl group having 1 to 3 carbon atoms, and $R^7$ is a hydrogen atom or an alkyl group having 1 to 3 carbon atoms, any 1 to 3 hydrogen atoms of which are optionally substituted with a fluorine atom(s) or a chlorine atom(s).

In this example, a higher RORγ antagonistic activity can be expected.

In the cyclic amine derivative represented by general formula (I), it is more preferable that $R^1$ is a methoxy group, any 1 to 3 hydrogen atoms of which are optionally substituted with a fluorine atom(s), $R^2$ is a fluorine atom or a chlorine atom, $R^3$ is a hydrogen atom, a fluorine atom, or a hydroxy group, $R^4$ is a hydrogen atom or a fluorine atom, n is an integer of 0 to 4, $R^5$ is a hydrogen atom, —$OR^7$, —$N(R^7)R^8$, an alkyl group having 1 to 3 carbon atoms, any 1 to 3 hydrogen atoms of which are optionally substituted with a fluorine atom(s), or a 5-membered heteroaryl group, any hydrogen atom(s) of which is/are optionally substituted with a methyl group(s), $R^6$ is a methyl group or an ethyl group, $R^7$ is a hydrogen atom or an alkyl group having 1 to 3 carbon atoms, any 1 to 3 hydrogen atoms of which are optionally substituted with a fluorine atom(s), and $R^8$ is a hydrogen atom, a methyl group, an acyl group having 2 to 4 carbon atoms, or an alkylsulfonyl group having 1 to 3 carbon atoms.

In this example, a higher RORγ antagonistic activity can be expected.

In the cyclic amine derivative represented by general formula (I), it is still more preferable that $R^1$ is a trifluoromethoxy group, $R^2$ is a chlorine atom, $R^3$ is a hydrogen atom, $R^4$ is a hydrogen atom, X is —$C(=O)$—$(CH_2)_n$—$R^5$, n is an integer of 0 to 3, $R^5$ is a methyl group, a trifluoromethyl group, —$N(R^7)R^8$, an imidazolyl, triazolyl, or tetrazolyl group, any hydrogen atom(s) of which is/are optionally substituted with a methyl group(s), $R^7$ is a hydrogen atom, a methyl group, or an ethyl group, and $R^8$ is a hydrogen atom, a methyl group, an acetyl group, a propionyl group, a methylsulfonyl group, or an ethylsulfonyl group.

In this example, a higher RORγ antagonistic activity can be expected, and further an excellent therapeutic effect or preventive effect in alopecia areata can be expected.

We also provide a method of treating or preventing alopecia areata, including a step of administering a cyclic amine derivative represented by general formula (I) or a pharmacologically acceptable salt thereof to a subject in need of treatment or prevention of alopecia areata. The above preferred aspect relating to the cyclic amine derivative represented by general formula (I) also applies to this method.

We further provide a cyclic amine derivative represented by general formula (I) or a pharmacologically acceptable salt thereof for use in a method of treating or preventing alopecia areata. The above preferred aspect relating to the cyclic amine derivative represented by general formula (I) also applies to this derivative.

We still further provide use of a cyclic amine derivative represented by general formula (I) or a pharmacologically acceptable salt thereof for production of a therapeutic agent or a preventive agent for alopecia areata. The above preferred derivative relating to the cyclic amine derivative represented by general formula (I) also applies to this use.

The therapeutic agent or the preventive agent for alopecia areata can effectively suppress the function of RORγ and can remarkably improve the symptoms of alopecia areata.

DETAILED DESCRIPTION

Figure 1:
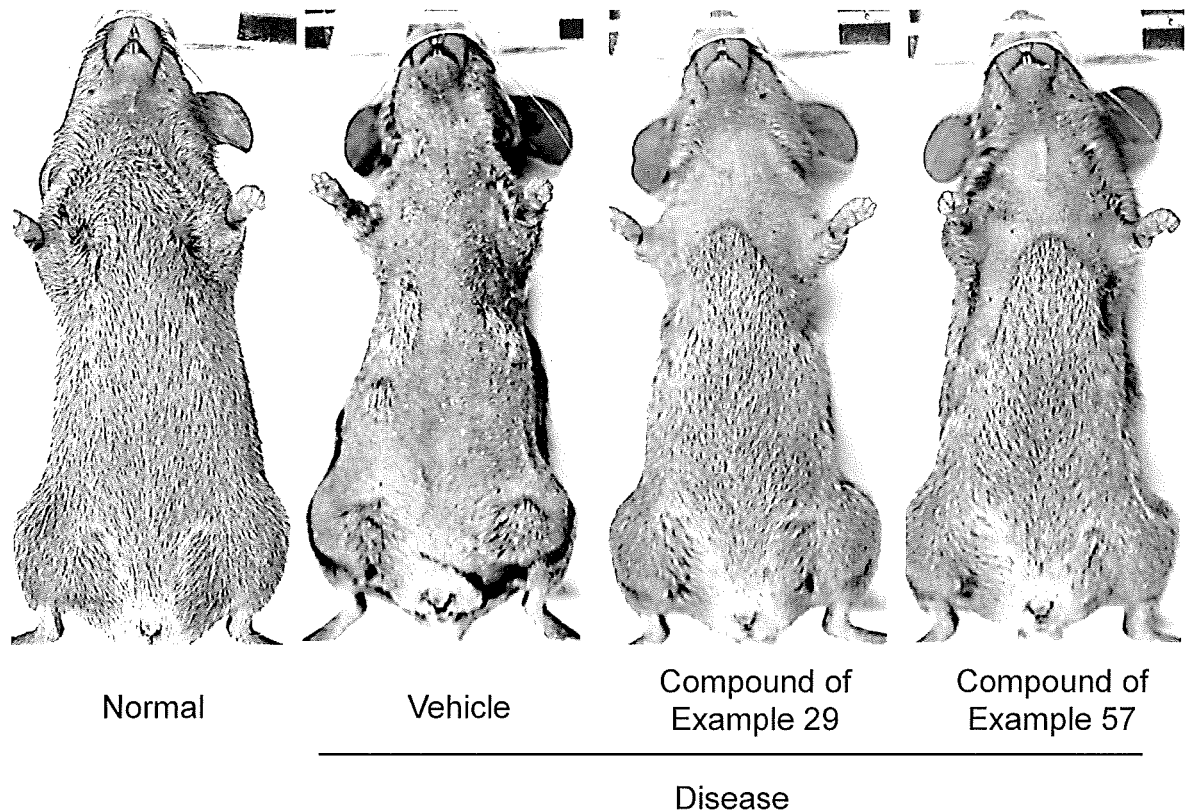
FIG. 1 is a photograph showing the suppressing effects of the compound of Example 29 and the compound of Example 57 on increase in the range of hair loss in a mouse alopecia areata model.

The therapeutic agent or the preventive agent for alopecia areata is characterized by containing the cyclic amine derivative represented by general formula (I) or a pharmacologically acceptable salt thereof as an active ingredient:

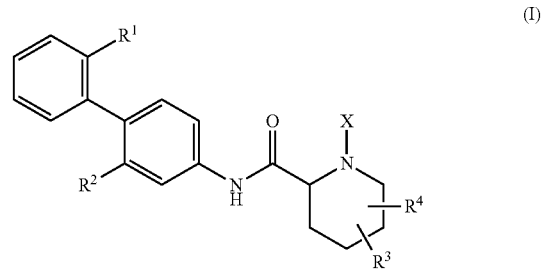

wherein
$R^1$ represents an alkyloxy group having 1 to 3 carbon atoms, any 1 to 3 hydrogen atoms of which are optionally substituted with a halogen atom(s),
$R^2$ represents a halogen atom,
$R^3$ represents a hydrogen atom, a halogen atom, or a hydroxy group,
$R^4$ represents a hydrogen atom or a halogen atom,
X represents —$C(=O)$—$(CH_2)_n$—$R^5$ or —$S(=O)_2$—$R^6$,
n represents an integer of 0 to 5,
$R^5$ represents a hydrogen atom, —$OR^7$, —$SR^7$, —$S(=O)_2$—$R^7$, —$C(=O)$—$OR^7$, —$N(R^7)R^8$, an alkyl group having 1 to 3 carbon atoms, any 1 to 3 hydrogen atoms of which are optionally substituted with a halogen atom(s), or a heteroaryl group, any hydrogen atom(s) of which is/are optionally substituted with an alkyl group(s) having 1 to 3 carbon atoms,
$R^6$ represents an alkyl group having 1 to 5 carbon atoms,
$R^7$ represents a hydrogen atom or an alkyl group having 1 to 3 carbon atoms, any 1 to 3 hydrogen atoms of which are optionally substituted with a halogen atom(s), and
$R^8$ represents a hydrogen atom, an alkyl group having 1 to 3 carbon atoms, an acyl group having 2 to 4 carbon atoms, or an alkylsulfonyl group having 1 to 3 carbon atoms.

The following terms as used herein are defined as follows, unless otherwise specified.

The term "alkyl group having 1 to 3 carbon atoms" means a methyl group, an ethyl group, a propyl group, or an isopropyl group.

The term "alkyl group having 1 to 5 carbon atoms" means a linear saturated hydrocarbon group having 1 to 5 carbon atoms or a branched saturated hydrocarbon group having 3 to 5 carbon atoms, and examples thereof include a methyl group, an ethyl group, a propyl group, an isopropyl group, a butyl group, an isobutyl group, a sec-butyl group, a tert-butyl group, a pentyl group, an isopentyl group, a neopentyl group, or a tert-pentyl group.

The term "alkyloxy group having 1 to 3 carbon atoms" means a methoxy group, an ethoxy group, a propyloxy group, or an isopropyloxy group.

The term "acyl group having 2 to 4 carbon atoms" means an acetyl group, a propionyl group, a butanoyl group, or a 2-methylpropanoyl group.

The term "alkylsulfonyl group having 1 to 3 carbon atoms" means a methylsulfonyl group, an ethylsulfonyl group, a propylsulfonyl group, or an isopropylsulfonyl group.

The term "heteroaryl group" means a heterocyclic aromatic group containing 1 to 4 heteroatoms independently selected from the group consisting of a nitrogen atom, an oxygen atom, and a sulfur atom, and examples thereof include a thienyl group, a pyrrolyl group, a furyl group, a thiazolyl group, an imidazolyl group, an oxazolyl group, a pyrazolyl group, an isothiazolyl group, an isoxazolyl group, a triazolyl group, an oxadiazolyl group, a tetrazolyl group, a pyridyl group, a pyridazinyl group, a pyrimidinyl group, a pyrazinyl group, or a triazinyl group.

The term "5-membered heteroaryl group" means a heterocyclic aromatic group having 5 ring-constituting atoms containing 1 to 4 heteroatoms independently selected from the group consisting of a nitrogen atom, an oxygen atom, and a sulfur atom, and examples thereof include a thienyl group, a pyrrolyl group, a furyl group, a thiazolyl group, an imidazolyl group, an oxazolyl group, a pyrazolyl group, an isothiazolyl group, an isoxazolyl group, a triazolyl group, an oxadiazolyl group, or a tetrazolyl group.

The term "halogen atom" means a fluorine atom, a chlorine atom, a bromine atom, or an iodine atom.

The term "alkyl group having 1 to 3 carbon atoms, any 1 to 3 hydrogen atoms of which are optionally substituted with a halogen atom(s)" means an alkyl group having 1 to 3 carbon atoms as defined above, any 1 to 3 hydrogen atoms of which may be each independently substituted with a halogen atom as defined above, and examples thereof include a methyl group, an ethyl group, a propyl group, an isopropyl group, a fluoromethyl group, a difluoromethyl group, a trifluoromethyl, a 2-fluoroethyl group, a trifluoroethyl group, a trichloromethyl group, or a trichloroethyl group.

The term "alkyl group having 1 to 3 carbon atoms, any 1 to 3 hydrogen atoms of which are optionally substituted with a fluorine atom(s) or a chlorine atom(s)" means an alkyl group having 1 to 3 carbon atoms as defined above, any 1 to 3 hydrogen atoms of which may be each independently substituted with a fluorine atom or a chlorine atom, and examples thereof include a methyl group, an ethyl group, a propyl group, an isopropyl group, a fluoromethyl group, a difluoromethyl group, a trifluoromethyl group, a 2-fluoroethyl group, a trifluoroethyl group, a trichloromethyl group, or a trichloroethyl group.

The term "alkyl group having 1 to 3 carbon atoms, any 1 to 3 hydrogen atoms of which are optionally substituted with a fluorine atom(s)" means an alkyl group having 1 to 3 carbon atoms as defined above, any 1 to 3 hydrogen atoms of which may be substituted with a fluorine atom(s), and examples thereof include a methyl group, an ethyl group, a propyl group, an isopropyl group, a fluoromethyl group, a difluoromethyl group, a trifluoromethyl group, a 2-fluoroethyl group, or a trifluoroethyl group.

The term "alkyloxy group having 1 to 3 carbon atoms, any 1 to 3 hydrogen atoms of which are optionally substituted with a halogen atom(s)" means an alkyloxy group having 1 to 3 carbon atoms as defined above, any 1 to 3 hydrogen atoms of which may be each independently substituted with a halogen atom as defined above, and examples thereof include a methoxy group, an ethoxy group, a propyloxy group, an isopropyloxy group, a fluoromethoxy group, a difluoromethoxy group, a trifluoromethoxy group, a 2-fluoroethoxy group, a trifluoroethoxy group, a trichloromethoxy group, or a trichloroethoxy group.

The term "alkyloxy group having 1 to 3 carbon atoms, any 1 to 3 hydrogen atoms of which are optionally substituted with a fluorine atom(s) or a chlorine atom(s)" means an alkyloxy group having 1 to 3 carbon atoms as defined above, any 1 to 3 hydrogen atoms of which may be each independently substituted with a fluorine atom or a chlorine atom, and examples thereof include a methoxy group, an ethoxy group, a propyloxy group, an isopropyloxy group, a fluoromethoxy group, a difluoromethoxy group, a trifluoromethoxy group, a 2-fluoroethoxy group, a trifluoroethoxy group, a trichloromethoxy group, or a trichloroethoxy group.

The term "methoxy group, any 1 to 3 hydrogen atoms of which are optionally substituted with a fluorine atom(s)" means a methoxy group, a fluoromethoxy group, a difluoromethoxy group, or a trifluoromethoxy group.

The term "heteroaryl group, any hydrogen atom(s) of which is/are optionally substituted with an alkyl group(s) having 1 to 3 carbon atoms" means a heteroaryl group as defined above, any one or more hydrogen atoms (e.g., any 1 to 4 hydrogen atoms) of which may be each independently substituted with an alkyl group having 1 to 3 carbon atoms as defined above, and examples thereof include a thienyl group, a pyrrolyl group, a furyl group, a thiazolyl group, an imidazolyl group, an oxazolyl group, a pyrazolyl group, an isothiazolyl group, an isoxazolyl group, a triazolyl group, an oxadiazolyl group, a tetrazolyl group, a pyridyl group, a pyridazinyl group, a pyrimidinyl group, a pyrazinyl group, a triazinyl group, a methylthienyl group, a dimethylthienyl group, an ethylthienyl group, a methylpyrrolyl group, a dimethylpyrrolyl group, an ethylpyrrolyl group, a methylfuryl group, a dimethylfuryl group, an ethylfuryl group, a methylthiazolyl group, a dimethylthiazolyl group, an ethylthiazolyl group, a methylimidazolyl group, a dimethylimidazolyl group, an ethylimidazolyl group, a methyloxazolyl group, a dimethyloxazolyl group, an ethyloxazolyl group, a methylpyrazolyl group, a dimethylpyrazolyl group, an ethylpyrazolyl group, a methylisothiazolyl group, a dimethylisothiazolyl group, an ethylisothiazolyl group, a methylisoxazolyl group, a dimethylisoxazolyl group, an ethylisoxazolyl group, a methyltriazolyl group, a dimethyltriazolyl group, an ethyltriazolyl group, a methyloxadiazolyl group, a dimethyloxadiazolyl group, an ethyloxadiazolyl group, a methyltetrazolyl group, an ethyltetrazolyl group, a methylpyridyl group, a dimethylpyridyl group, an ethylpyridyl group, a methylpyridazinyl group, a dimethylpyridazinyl group, an ethylpyridazinyl group, a methylpyrimidinyl group, a dimethylpyrimidinyl group, an ethylpyrimidinyl group, a methylpyrazinyl group, a dimethylpyrazinyl group, an ethylpyrazinyl group, a methyltriazinyl group, a dimethyltriazinyl group, or an ethyltriazinyl group.

The term "heteroaryl group, any hydrogen atom(s) of which is/are optionally substituted with a methyl group(s)" means a heteroaryl group as defined above, any one or more hydrogen atoms (e.g., any 1 to 4 hydrogen atoms) of which may be each independently substituted with a methyl group, and examples thereof include a thienyl group, a pyrrolyl group, a furyl group, a thiazolyl group, an imidazolyl group, an oxazolyl group, a pyrazolyl group, an isothiazolyl group, an isoxazolyl group, a triazolyl group, an oxadiazolyl group, a tetrazolyl group, a pyridyl group, a pyridazinyl group, a pyrimidinyl group, a pyrazinyl group, a triazinyl group, a methylthienyl group, a dimethylthienyl group, a methylpyrrolyl group, a dimethylpyrrolyl group, a methylfuryl group, a dimethylfuryl group, a methylthiazolyl group, a dimethylthiazolyl group, a methylimidazolyl group, dimethylimidazolyl group, a methyloxazolyl group, a dimethyloxazolyl group, a methylpyrazolyl group, a dimethylpyrazolyl group, a methylisothiazolyl group, a dimethylisothiazolyl group, a methylisoxazolyl group, a dimethylisoxazolyl group, a methyltriazolyl group, dimethyltriazolyl group, a methyloxadiazolyl group, a dimethyloxadiazolyl group, a methyltetrazolyl group, a methylpyridyl group, a dimethylpyridyl group, a methylpyridazinyl group, a dimethylpyridazinyl group, a methylpyrimidinyl group, a dimethylpyrimidinyl group, a methylpyrazinyl group, a dimethylpyrazinyl group, a methyltriazinyl group, or a dimethyltriazinyl group.

The term "5-membered heteroaryl group, any hydrogen atom(s) of which is/are optionally substituted with a methyl group(s)" means a 5-membered ring heteroaryl group as defined above, any one or more hydrogen atoms (e.g., any 1 to 4 hydrogen atoms) of which may be each independently substituted with a methyl group, and examples thereof include a thienyl group, a pyrrolyl group, a furyl group, a thiazolyl group, an imidazolyl group, an oxazolyl group, a pyrazolyl group, an isothiazolyl group, an isoxazolyl group, a triazolyl group, an oxadiazolyl group, a tetrazolyl group, a methylthienyl group, a dimethylthienyl group, a methylpyrrolyl group, a dimethylpyrrolyl group, a methylfuryl group, a dimethylfuryl group, a methylthiazolyl group, a dimethylthiazolyl group, a methylimidazolyl group, a dimethylimidazolyl group, a methyloxazolyl group, a dimethyloxazolyl group, a methylpyrazolyl group, a dimethylpyrazolyl group, a methylisothiazolyl group, a dimethylisothiazolyl group, a methylisoxazolyl group, a dimethylisoxazolyl group, a methyltriazolyl group, dimethyltriazolyl group, a methyloxadiazolyl group, a dimethyloxadiazolyl group, or a methyltetrazolyl group.

With respect to the abovementioned cyclic amine derivative, in general formula (I), $R^1$ is preferably an alkyloxy group having 1 to 3 carbon atoms, any 1 to 3 hydrogen atoms of which may be each independently substituted with a fluorine atom or a chlorine atom, more preferably a methoxy group, any 1 to 3 hydrogen atoms of which may be each independently substituted with a fluorine atom, and still more preferably a trifluoromethoxy group.

$R^2$ is preferably a fluorine atom or a chlorine atom, and more preferably a chlorine atom.

$R^3$ is preferably a hydrogen atom, a fluorine atom, a chlorine atom, or a hydroxy group, more preferably a hydrogen atom, a fluorine atom, or a hydroxy group, and still more preferably a hydrogen atom.

$R^4$ is preferably a hydrogen atom, a fluorine atom, or a chlorine atom, more preferably a hydrogen atom or a fluorine atom, and still more preferably a hydrogen atom.

X is preferably —C(═O)—(CH$_2$)$_n$—R$^5$.

n is preferably an integer of 0 to 4, and more preferably an integer of 0 to 3.

$R^5$ is preferably a hydrogen atom, —OR$^7$, —SR$^7$, —S(═O)$_2$—R$^7$, —C(═O)—OR$^7$, —N(R$^7$)R$^8$, an alkyl group having 1 to 3 carbon atoms, any 1 to 3 hydrogen atoms of which may be each independently substituted with a fluorine atom or a chlorine atom, or a heteroaryl group, any one or more hydrogen atoms of which may be each independently substituted with a methyl group, more preferably a hydrogen atom, —OR$^7$, —N(R$^7$)R$^8$, an alkyl group having 1 to 3 carbon atoms, any 1 to 3 hydrogen atoms of which may be each independently substituted with a fluorine atom, or a 5-membered heteroaryl group, any one or more hydrogen atoms of which may be each independently substituted with a methyl group, and still more preferably a methyl group, a trifluoromethyl group, —N(R$^7$)R$^8$, an imidazolyl, triazolyl, or tetrazolyl group, any one or more hydrogen atoms of which may be each independently substituted with a methyl group.

$R^6$ is preferably an alkyl group having 1 to 3 carbon atoms, and more preferably a methyl group or an ethyl group.

$R^7$ is preferably a hydrogen atom or an alkyl group having 1 to 3 carbon atoms, any 1 to 3 hydrogen atoms of which may be each independently substituted with a fluorine atom or a chlorine atom, more preferably a hydrogen atom or an alkyl group having 1 to 3 carbon atoms, any 1 to 3 hydrogen atoms of which may be each independently substituted with a fluorine atom, and still more preferably a hydrogen atom, a methyl group, or an ethyl group.

$R^8$ is more preferably a hydrogen atom, a methyl group, an acyl group having 2 to 4 carbon atoms, or an alkylsulfonyl group having 1 to 3 carbon atoms, and more preferably a hydrogen atom, a methyl group, an acetyl group, a propionyl group, a methylsulfonyl group, or an ethylsulfonyl group.

Specific examples of preferred compounds of the cyclic amine derivative represented by general formula (I) are shown in Tables 1-1 to 1-3, but this disclosure is not limited thereto.

TABLE 1-1

Structural formula

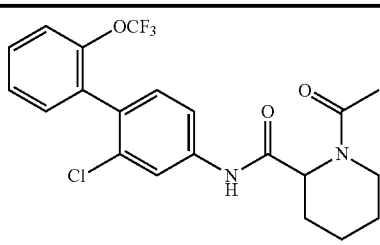

TABLE 1-1-continued

Structural formula

TABLE 1-1-continued

Structural formula

TABLE 1-2

Structural formula (chemical structures)

TABLE 1-2-continued
Structural formula
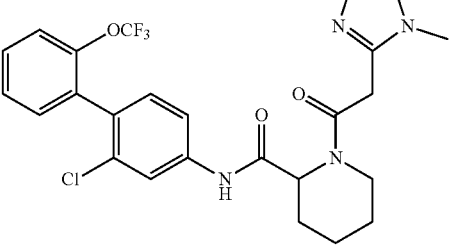
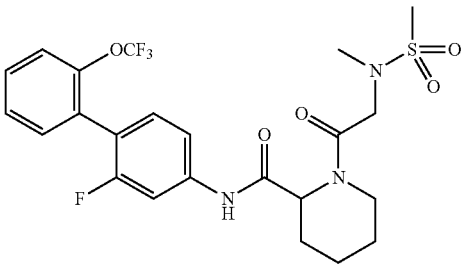
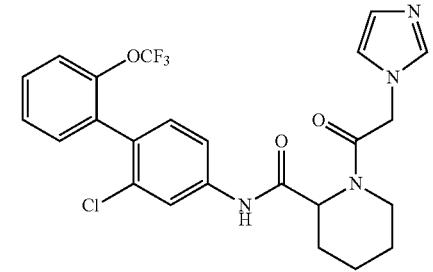
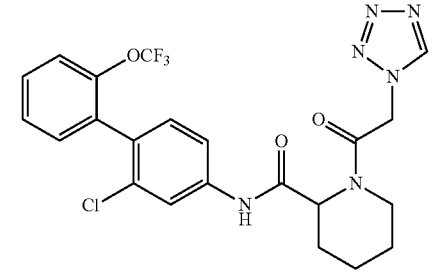
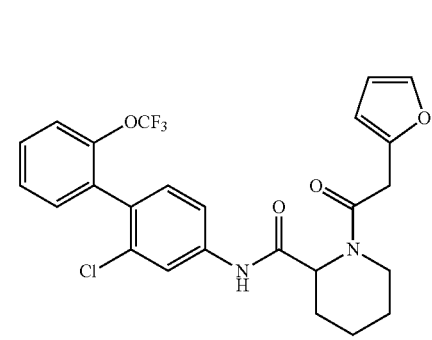 [SMILES: O=C(Nc1ccc(-c2ccccc2OC(F)(F)F)c(Cl)c1)C1CCCCN1C(=O)Cc1ccco1]
TABLE 1-2-continued
Structural formula
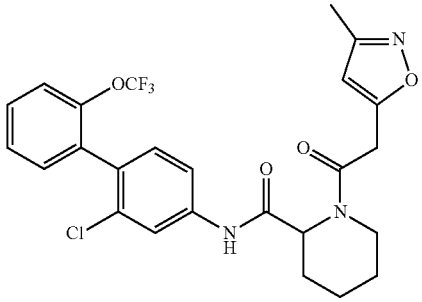 [SMILES: Cc1cc(CC(=O)N2CCCCC2C(=O)Nc2ccc(-c3ccccc3OC(F)(F)F)c(Cl)c2)on1]
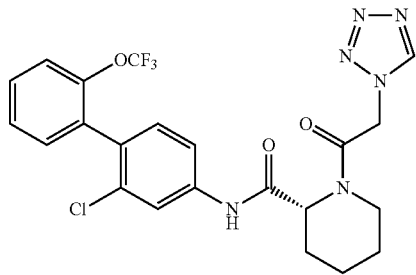
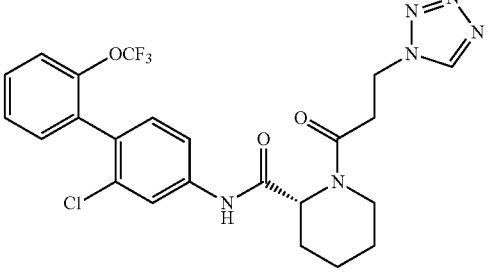
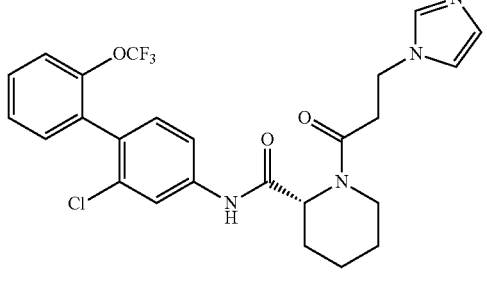
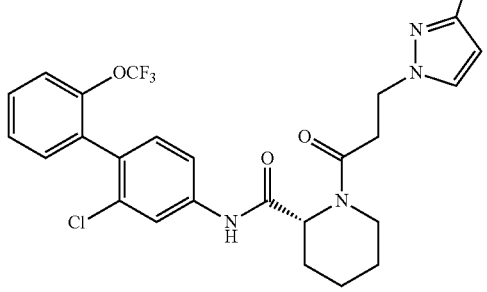

TABLE 1-3
| Structural formula |
|---|
| 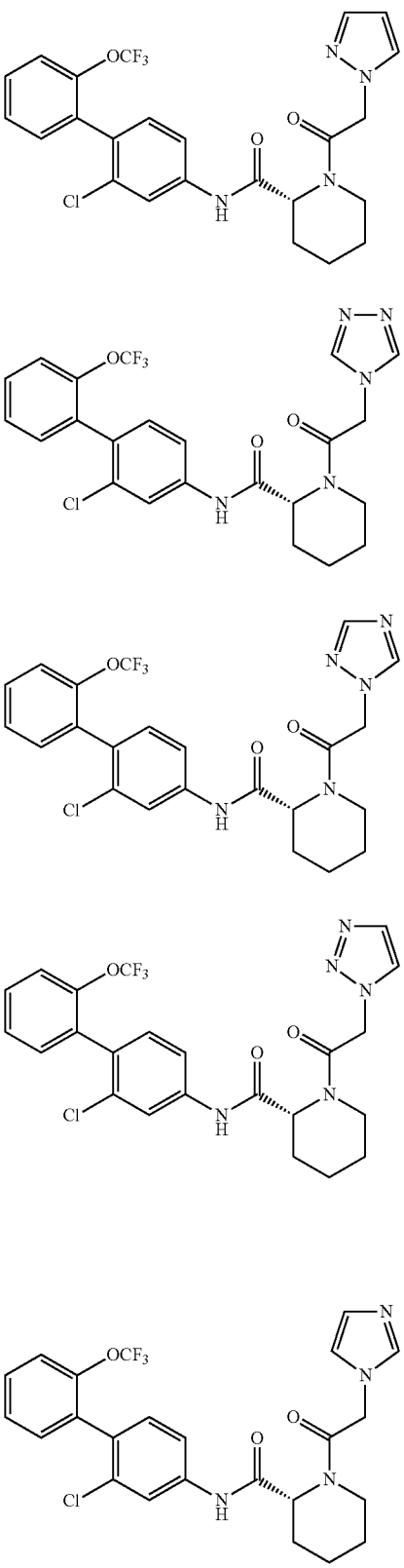 |
TABLE 1-3-continued
| Structural formula |
|---|
| 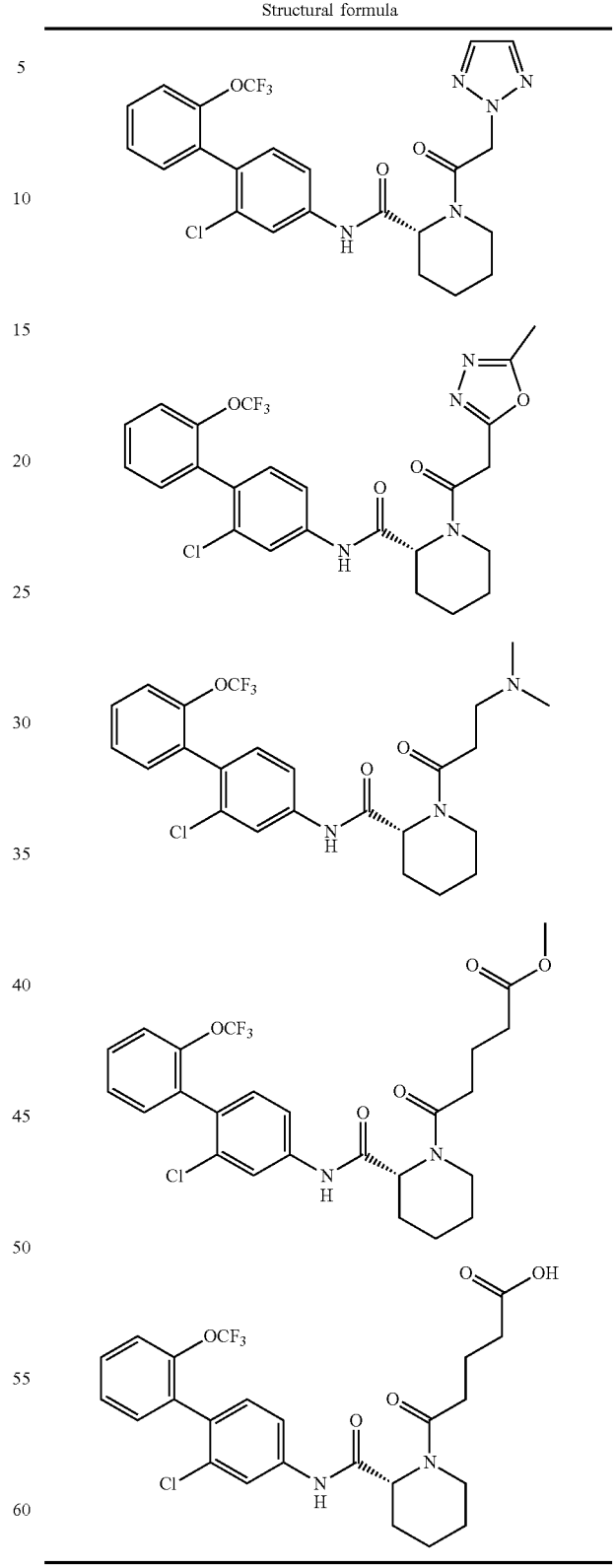 |
The compounds mentioned in Tables 1-1 to 1-3 also include a pharmacologically acceptable salt thereof.
The cyclic amine derivative represented by general formula (I) might include conformational isomers, rotamers, tautomers, optical isomers, diastereomers and the like, and include not only a single isomer but also racemates and diastereomer mixtures.

The cyclic amine derivative represented by general formula (I) may be labeled by one or more isotopes, and examples of the labeled isotope include $^{2}H$, $^{3}H$, $^{13}C$, $^{14}C$, $^{15}N$, $^{15}O$, $^{18}O$, and/or $^{125}I$.

Examples of the "pharmacologically acceptable salt" of the cyclic amine derivative represented by general formula (I) include a salt with an inorganic base, a salt with an organic base, a salt with an inorganic acid, and a salt with an organic acid. Examples of the salt with an inorganic base include an alkali metal salt such as a sodium salt or a potassium salt, an alkaline earth metal salt such as a calcium salt or a magnesium salt, an ammonium salt, an aluminum salt or a zinc salt, and examples of the salt with an organic base include a salt with an organic amine such as triethylamine, ethanolamine, morpholine, piperidine or dicyclohexylamine, or a salt with a basic amino acid such as arginine or lysine. Examples of the salt with an inorganic acid include a hydrochloride, a sulfate, a nitrate, a hydrobromide, a hydroiodide, a phosphate or the like, and examples of the salt with an organic acid include an oxalate, a malonate, a citrate, a fumarate, a lactate, a malate, a succinate, a tartrate, an acetate, a trifluoroacetate, a maleate, a gluconate, a benzoate, an ascorbate, a glutarate, a mandelate, a phthalate, a methanesulfonate, an ethanesulfonate, a benzenesulfonate, a p-toluenesulfonate, a camphorsulfonate, an aspartate, a glutamate, a cinnamate or the like.

The cyclic amine derivative represented by general formula (I) or a pharmacologically acceptable salt thereof may be an anhydride or a solvate such as a hydrate. Here, the solvate is preferably a pharmacologically acceptable solvate. The pharmacologically acceptable solvate may be either a hydrate or a non-hydrate and is preferably a hydrate. Examples of the solvent constituting the solvate include alcohol-based solvents such as methanol, ethanol, or n-propanol, N,N-dimethylformamide (hereinafter abbreviated to DMF), dimethylsulfoxide (hereinafter abbreviated to DMSO), or water.

The cyclic amine derivative represented by general formula (I) (hereinafter referred to as cyclic amine derivative (I)) can be produced by an appropriate method based on features derived from a basic skeleton and types of substituents thereof. A starting material and a reagent used in the production of these compounds can generally be commercially available or produced by known methods.

Cyclic amine derivative (I) and the intermediate and starting material to be used in the production thereof can be isolated and purified by known means. Examples of known means for isolation and purification include solvent extraction, recrystallization, or chromatography.

When cyclic amine derivative (I) contains an optical isomer or a stereoisomer, each isomer can be obtained as a single compound by a known method. Examples of the known method include crystallization, enzymatic resolution, or chiral chromatography.

In each of the reactions of the production methods mentioned below, when the starting compound has an amino group or a carboxyl group, a protective group may be introduced into these groups, and after the reaction, the protective group can be deprotected as appropriate to obtain the target compound.

Examples of the protective group of the amino group include an alkylcarbonyl group having 2 to 6 carbon atoms (e.g., an acetyl group), a benzoyl group, an alkyloxycarbonyl group having 2 to 8 carbon atoms (e.g., a tert-butoxycarbonyl group or a benzyloxy carbonyl group), an aralkyl group having 7 to 10 carbon atoms (e.g., a benzyl group), or a phthaloyl group.

Examples of the protective group of the carboxyl group include an alkyl group having 1 to 6 carbon atoms (e.g., a methyl group, an ethyl group, or a tert-butyl group) or an aralkyl group having 7 to 10 carbon atoms (e.g., a benzyl group).

The deprotection of the protective group varies depending on the kind of the protective group, but deprotection can be performed according to a known method (for example, Greene, TW, "Greene's Protective Groups in Organic Synthesis", Wiley-Interscience) or a method analogous thereto.

As shown in, for example, Scheme 1, cyclic amine derivative (I) can be obtained by a coupling reaction (first step) of boronic acid derivative (II) with aryl halide derivative (III) in the presence of a metal catalyst and a base, followed by a condensation reaction (second step) of biphenylamine derivative (IV) obtained in the first step with pipecolic acid derivative (V) in the presence of a condensing agent and a base, followed by a deprotection reaction (third step) of N-tert-butoxycarbonylpipecolic acid amide derivative (VI) obtained in the second step in the presence of an acid, and followed by a condensation reaction (fourth step) of pipecolic acid amide derivative (VII) obtained in the third step with organic acid anhydride derivative (VIII) in the presence of a base. Cyclic amine derivative (I) can also be obtained by a condensation reaction of pipecolic acid amide derivative (VII) with organic acid ester derivative (IX). Cyclic amine derivative (I) can also be obtained by a condensation reaction of pipecolic acid amide derivative (VII) with organic acid chloride derivative (X) in the presence of a base. Cyclic amine derivative (I) can also be obtained by a condensation reaction of pipecolic acid amide derivative (VII) and organic acid derivative (XI) in the presence of a condensing agent and a base. Cyclic amine derivative (I) can also be obtained by a condensation reaction of pipecolic acid amide derivative (VII) with trimethylsilyl isocyanate in the presence of a base.

When cyclic amine derivative (I) contains, for example, an amino group, the amino group may be converted into an amide group, a sulfonamide group or the like, or an N-alkyl derivative by a condensation reaction, a reductive amination reaction or the like. When cyclic amine derivative (I) contains a sulfide group, the sulfide group may be converted into a sulfonyl group by an oxidation reaction. When cyclic amine derivative (I) contains an ester group, the ester group may be converted into a carboxyl group by a hydrolysis reaction.

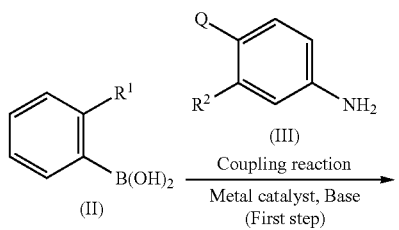

Scheme 1

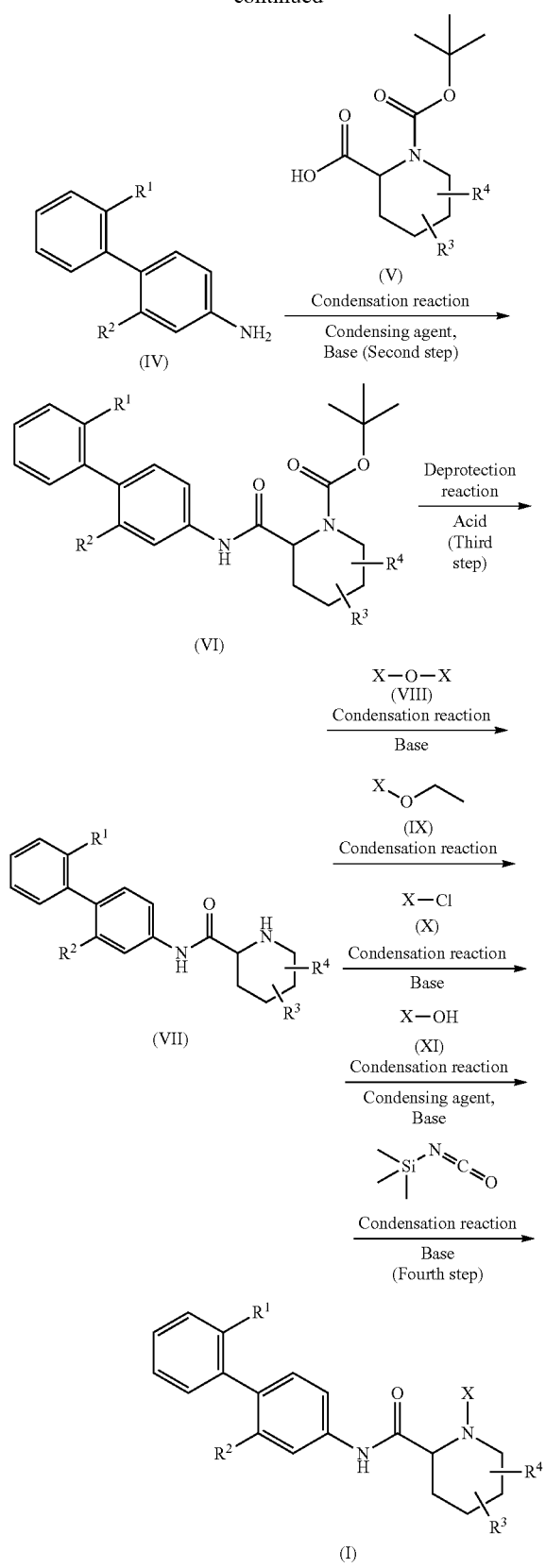

In Scheme 1, Q represents a halogen atom, and R¹ to R⁴ and X are as defined above.

First Step

The amount of aryl halide derivative (III) used in the coupling reaction is preferably 0.5 to 10 equivalents, and more preferably 0.7 to 3 equivalents, based on boronic acid derivative (II).

Examples of the metal catalyst used in the coupling reaction include 1,1'-bis(diphenylphosphino)ferrocene dichloropalladium(II) dichloromethane adduct, palladium (II) chloride, bis(dibenzylideneacetone)palladium(0), tetrakistriphenylphosphine palladium(0), or dichlorobistriphenylphosphine palladium(0), and 1,1'-bis (diphenylphosphino)ferrocene dichloropalladium(II) dichloromethane adduct is preferable.

The amount of the metal catalyst to be used for the coupling reaction is preferably 0.01 to 5 equivalents, and more preferably 0.05 to 0.5 equivalents, based on boronic acid derivative (II).

Examples of the base used in the coupling reaction include an organic base such as triethylamine or diisopropylethylamine, an inorganic base such as sodium carbonate or potassium carbonate, a lithium amide such as lithium hexamethyldisilazide or lithium diisopropylamide, or a metal alkoxide such as tert-butyloxy sodium, tert-butyloxy potassium, or a mixture thereof, and an inorganic base such as sodium carbonate or potassium carbonate, is preferable.

The amount of the base to be used for the coupling reaction is preferably 0.5 to 10 equivalents, and more preferably 1 to 3 equivalents based on boronic acid derivative (II).

The reaction solvent used for the coupling reaction is appropriately selected according to the type of reagent to be used or the like, but is not particularly limited as long as it does not inhibit the reaction, and examples thereof include ether-based solvents such as tetrahydrofuran, 1,4-dioxane, ethylene glycol dimethyl ether, or dimethoxyethane, nitrile-based solvents such as acetonitrile or propionitrile, aromatic hydrocarbon solvents such as benzene or toluene, aprotic polar solvents such as DMF or DMSO, water, or a mixture thereof. A mixed solvent of nitrile-based solvents such as acetonitrile or propionitrile, and water, is preferable.

The reaction temperature of the coupling reaction is preferably 0 to 200° C., and more preferably 50 to 150° C.

The reaction time of the coupling reaction is appropriately selected according to the conditions such as the reaction temperature, and the reaction time is preferably 1 to 30 hours.

The concentration of boronic acid derivative (II) used in the coupling reaction at the start of the reaction is preferably 1 mmol/L to 1 mol/L.

Boronic acid derivative (II) and aryl halide derivative (III) used in the coupling reaction can be purchased or produced by a known method.

Step 2

The amount of pipecolic acid derivative (V) used in the condensation reaction is preferably 0.1 to 10 equivalents, and more preferably 0.5 to 3 equivalents, based on biphenylamine derivative (IV).

Examples of the condensing agent used in the condensation reaction include N,N'-dicyclohexylcarbodiimide, N-ethyl-N'-3-dimethylaminopropylcarbodiimide hydrochloride, N,N'-carbodiimidazole, {{[(1-cyano-2-ethoxy-2-oxo-ethylidene)amino]oxy}-4-morpholinomethylene}dimethylammonium hexafluorophosphate (hereinafter abbreviated to COMU), O-(7-azabenzotriazol-1-yl)-1,1,3,3-tetramethyluronium hexafluorophosphate (hereinafter abbreviated to HATU), or O-(benzotriazol-1-yl)-N,N,N',N'-tetramethyluronium hexafluorophosphate (hereinafter abbreviated to HBTU), and HATU or HBTU is preferable.

The amount of the condensing agent used in the condensation reaction is preferably 0.5 to 10 equivalents, and more preferably 1 to 3 equivalents, based on biphenylamine derivative (IV).

Examples of the base used in the condensation reaction include an organic base such as triethylamine or diisopropylethylamine, an inorganic base such as sodium hydrogen carbonate or potassium carbonate, a hydrogenated metal compound such as sodium hydride, potassium hydride, or calcium hydride, an alkyl lithium such as methyl lithium or butyl lithium, a lithium amide such as lithium hexamethyldisilazide or lithium diisopropylamide, or a mixture thereof, and an organic base such as triethylamine or diisopropylethylamine, is preferable.

The amount of the base used in the condensation reaction is preferably 0.5 to 10 equivalents, and more preferably 1 to 5 equivalents, based on biphenylamine derivative (IV).

Biphenylamine derivative (IV) used in the condensation reaction may be a free form or a salt such as a hydrochloride.

The reaction solvent used in the condensation reaction is appropriately selected according to the type of the reagent to be used or the like, but is not particularly limited as long as it does not inhibit the reaction, and examples thereof include ether-based solvents such as tetrahydrofuran, 1,4-dioxane, ethylene glycol dimethyl ether, or dimethoxyethane, halogen-based solvents such as dichloromethane, chloroform, or 1,2-dichloroethane, aprotic polar solvents such as DMF or DMSO, or nitrile-based solvents such as acetonitrile or propionitrile, and halogen-based solvents such as dichloromethane, chloroform, or 1,2-dichloroethane, or aprotic polar solvents such as DMF or DMSO, are preferable.

The reaction temperature of the condensation reaction is preferably 0 to 200° C., and more preferably 20 to 100° C.

The reaction time of the condensation reaction is appropriately selected according to the conditions such as the reaction temperature, and is preferably 0.5 to 100 hours.

The concentration of biphenylamine derivative (IV) used in the condensing reaction at the start of the reaction is preferably 1 mmol/L to 1 mol/L.

Pipecolic acid derivative (V) used in the condensation reaction can be purchased or produced by a known method or a method analogous thereto.

Third Step

Examples of the acid used in the deprotection reaction include hydrochloric acid, trifluoroacetic acid, or hydrofluoric acid, and hydrochloric acid or trifluoroacetic acid is preferable.

The amount of the acid used in the deprotection reaction is preferably 0.5 to 100 equivalents, and more preferably 1 to 30 equivalents, based on N-tert-butoxycarbonylpipecolic acid amide derivative (VI).

The reaction solvent used in the deprotection reaction is appropriately selected according to the type of the reagent to be used, but is not particularly limited as long as it does not inhibit the reaction, and examples thereof include ether-based solvents such as diethyl ether, tetrahydrofuran, dimethoxyethane, or 1,4-dioxane, ester-based solvents such as ethyl acetate or propyl acetate, chlorine-based solvents such as dichloromethane, chloroform, or 1,2-dichloroethane, alcohol-based solvents such as methanol or ethanol, aprotic polar solvents such as DMF or DMSO, or mixed solvents thereof, and halogen-based solvents such as dichloromethane, chloroform, or 1,2-dichloroethane, or aprotic polar solvents such as DMF or DMSO, are preferable.

The reaction temperature of the deprotection reaction is preferably −78° C. to 200° C., and more preferably −20° C. to 100° C.

The reaction time of the deprotection reaction is appropriately selected according to the conditions such as the reaction temperature, and the reaction time is preferably 1 to 50 hours.

The concentration of N-tert-butoxycarbonylpipecolic acid amide derivative (VI) used in the deprotection reaction at the start of the reaction is preferably 1 mmol/L to 1 mol/L.

Step 4

The amount of organic acid anhydride derivative (VIII), organic acid ester derivative (IX), organic acid chloride derivative (X), organic acid derivative (XI), or trimethylsilyl isocyanate used in the condensation reaction is preferably 1 to 200 equivalents, and more preferably 1 to 80 equivalents, based on pipecolic acid amide derivative (VII).

Examples of the condensing agent used in the condensation reaction include N,N'-dicyclohexylcarbodiimide, N-ethyl-N'-3-dimethylaminopropylcarbodiimide hydrochloride, N,N'-carbodiimidazole, COMU, HATU, or HBTU, and HATU or HBTU is preferable.

The amount of the condensing agent used in the condensation reaction is preferably 0 to 10 equivalents, and more preferably 0 to 3 equivalents, based on pipecolic acid amide derivative (VII).

Examples of the base used in the condensation reaction include an organic base such as triethylamine or diisopropylethylamine, an inorganic base such as sodium hydrogen carbonate or potassium carbonate, a hydrogenated metal compound such as sodium hydride, potassium hydride, or calcium hydride, an alkyl lithium such as methyl lithium or butyl lithium, lithium amide such as lithium hexamethyldisilazide or lithium diisopropylamide, or a mixture thereof, and an organic base such as triethylamine or diisopropylethylamine, is preferable.

The amount of the base used in the condensation reaction is preferably 0 to 10 equivalents, and more preferably 0 to 5 equivalents, based on pipecolic acid amide derivative (VII).

Pipecolic acid amide derivative (VII) used in the condensation reaction may be a free form or a salt such as a hydrochloride.

The reaction solvent used in the condensation reaction is appropriately selected according to the type of the reagent to be used or the like, but is not particularly limited as long as it does not inhibit the reaction, and examples thereof include ether-based solvents such as tetrahydrofuran, 1,4-dioxane, ethylene glycol dimethyl ether, or dimethoxyethane, chlorine-based solvents such as dichloromethane, chloroform, or 1,2-dichloroethane, aprotic polar solvents such as DMF or DMSO, or nitrile-based solvents such as acetonitrile or propionitrile, and halogen-based solvents such as dichloromethane, chloroform, or 1,2-dichloroethane, or aprotic polar solvents such as DMF or DMSO, are preferable.

The reaction temperature of the condensation reaction is preferably −78° C. to 200° C., and more preferably −20° C. to 100° C.

The reaction time of the condensation reaction is appropriately selected according to the conditions such as the reaction temperature, and the reaction time is preferably 0.5 to 100 hours.

The concentration of pipecolic acid amide derivative (VII) used in the coupling reaction at the start of the reaction is preferably 1 mmol/L to 1 mol/L.

Organic acid anhydride derivative (VIII), organic acid ester derivative (IX), organic acid chloride derivative (X), organic acid derivative (XI), and the trimethylsilyl isocyanate used in the condensation reaction can be purchased or produced by a known method or a method analogous thereto.

"RORγ antagonist" means a compound having an effect to suppress the functions of RORγ, thereby eliminating or attenuating its activity.

"Alopecia areata" is a disease which develops as a result of temporary impairment of hair matrix cells due to any cause; which lacks prodromal symptoms or subjective symptoms; and in which well-defined patches of hair loss appear suddenly. According to the severity, alopecia areata is classified into ophiasis in which hair loss occurs in the hairlines in the occipital to temporal regions of the head, alopecia totalis in which the entire scalp hair is lost due to fusion of patches of hair loss, and alopecia universalis in which not only the scalp hair but also the hair of the whole body are lost.

It is possible to evaluate that cyclic amine derivative (I) or a pharmacologically acceptable salt thereof has RORγ antagonist activity that inhibits the binding between RORγ and a coactivator, using an in vitro study. Examples of the in vitro study include a method of evaluating the binding between RORγ and an agonist (e.g., cholesterol) (WO 2012/158784, WO 2013/018695) and a method of evaluating the binding between a ligand-binding domain of RORγ and a coactivator (WO 2012/064744, WO 2013/018695). The inhibitory effect on the transcription activity of RORγ can be evaluated using various reporter gene assays (WO 2012/158784, WO 2012/064744, WO 2013/018695).

The fact that cyclic amine derivative (I) or a pharmacologically acceptable salt thereof suppresses the function of RORγ can be evaluated using lymphocytic cells derived from various organs such as spleen or peripheral blood, with IL-17 production or Th17 cell differentiation as an index. Examples of the method using IL-17 production as an index include a method of measuring IL-17 production by IL-23 stimulation using mouse splenocytes (The Journal of Biological Chemistry, 2003, Vol. 278, No. 3, p. 1910-1914). Examples of the method using Th17 cell differentiation as an index include a method of measuring the IL-17 production amount or the proportion of IL-17-positive cells and the like by stimulating CD4-positive naive T cells derived from mouse splenocytes or human PBMC with various cytokines (e.g., IL-1β, IL-6, IL-23, and/or TGF-β) and various antibodies (e.g., anti-CD3 antibody, anti-CD28 antibody, anti-IL-4 antibody, anti-IFN-γ antibody, and/or anti-IL-2 antibody) to be differentiated into Th17 (WO 2012/158784, WO 2013/018695).

The fact that cyclic amine derivative (I) or a pharmacologically acceptable salt thereof is effective for treatment or prevention of alopecia areata can be evaluated using a disease model. Example of the disease model include an alopecia areata model (Journal of Investigative Dermatology, 2015, Vol. 135, p. 2530-2532). The alopecia areata model is an animal model in which lymphocytes of a donor mouse with spontaneous hair loss are transplanted into a recipient mouse to induce systemic hair loss. Due to the similarity of its symptoms and pathological findings to those of humans, the animal model has been widely used for studying the drug efficacy of a therapeutic agent or a preventive agent for alopecia areata.

For example, in this disease model, a suppressive effect on hair loss symptoms has been observed by administration of ruxolitinib, which is a Janus kinase (JAK) inhibitor (Nature Medicine, 2014, No. 20, p. 1043-1049). Furthermore, by administration of ruxolitinib to patients with alopecia areata, a hair growth effect has been observed in 75% of patients in the treatment group (Journal of Clinical Investigation Insight, 2016, No. 22, e89790). These results show that the drug efficacy evaluation using this disease model animal is useful for studying a therapeutic agent or a preventive agent for alopecia areata.

The efficacy of cyclic amine derivative (I) or a pharmacologically acceptable salt thereof on treatment or prevention of alopecia areata can be evaluated by, for example, using decrease in the amount of binding between a ligand-binding domain of RORγ and a coactivator or decrease in the amount of IL-17 production, which is an index of the function of RORγ, using the above in vitro study. The efficacy of treatment or prevention of alopecia areata can also be evaluated by, for example, using decrease in the hair loss score, which is a characteristic index of alopecia areata, as an index, using the above alopecia areata model.

Cyclic amine derivative (I) or a pharmacologically acceptable salt thereof can be used as a useful therapeutic agent or preventive agent for alopecia areata when administered to mammals (e.g., mice, rats, hamsters, rabbits, dogs, cats, monkeys, cattle, sheep, or humans), particularly humans. When cyclic amine derivative (I) or a pharmacologically acceptable salt thereof is clinically used as a therapeutic agent or a preventive agent for alopecia areata, cyclic amine derivative (I) or a pharmacologically acceptable salt thereof can be administered orally or parenterally as it is or by appropriately mixing with pharmacologically acceptable carriers including additives such as excipients, stabilizers, preservatives, buffers, solubilizers, emulsifiers, diluents, or isotonizing agents. The above therapeutic agent or preventive agent for alopecia areata can be produced by a usual method using these carriers for drugs appropriately. Examples of the dosage form of the above therapeutic agent or preventive agent for alopecia areata include oral agents such as tablets, capsules, granules, powders, or syrups, parenteral agents such as inhalants, injections, suppositories, or solutions, or ointments, creams, or patches for topical administration. The dosage form may also include known long-acting preparations.

The above therapeutic agent or preventive agent for alopecia areata contains preferably 0.00001 to 90% by weight, and more preferably 0.01 to 70% by weight of cyclic amine derivative (I) or a pharmacologically acceptable salt thereof. The dose is appropriately selected according to symptoms, age, and body weight of a patient, and an administration method, but is preferably 0.1 μg to 1 g per day for injections, 1 μg to 10 g per day for oral agents, 1 μg to 10 g per day for patches, 1 μg to 10 g per day for ointments, or 1 μg to 10 g per day for creams as an amount of active ingredient for an adult, each of which can be administered once or several times in divided doses.

Examples of the pharmacologically acceptable carriers or diluents of the above therapeutic agent or preventive agent for alopecia areata include binders (such as syrup, gelatin, gum arabic, sorbitol, polyvinyl chloride, or tragacanth), excipients (such as sugar, lactose, cornstarch, calcium phosphate, sorbitol, or glycine), or lubricants (such as magnesium stearate, polyethylene glycol, talc, or silica).

The above therapeutic agent or preventive agent for alopecia areata may be used by containing an appropriate amount of other drugs or in combination with other drugs for complementing or enhancing its treatment or preventive effect or reducing the dose.

Our agents, derivatives, methods and uses will be described in more detail by way of the following Reference Examples and Examples, but this disclosure is not limited thereto.

EXAMPLES

Commercially available compounds were used for the compounds used in the synthesis of the compounds of Reference Examples and Examples, no mention being made on the synthesis method thereof. "Room temperature" in the following Reference Examples and Examples usually indicates the temperature in a range of about 10° C. to about 35° C. Percentage (%) is mol/mol % for yield, % by volume for solvents used in column chromatography and high-performance liquid chromatography, and % by weight for others unless otherwise specified. The name of the solvent shown in the NMR data indicates the solvent used for the measurement. 400 MHz NMR spectrum was measured using JNM-AL 400 nuclear magnetic resonance spectrometer (JEOL Ltd.) or JNM-ECS 400 nuclear magnetic resonance spectrometer (JEOL Ltd.). Chemical shift was indicated by δ (unit: ppm) with tetramethylsilane as a standard, signals were indicated by s (singlet), d (doublet), t (triplet), q (quartet), quint (quintet), sept (septet), m (multiplet), br (broad), dd (double doublet), dt (double triplet), ddd (double double doublet), dq (double quartet), td (triplet doublet), and tt (triplet triplet). Mention is not made when protons of a hydroxyl group, an amino group or the like have a very gentle peak. ESI-MS spectra were measured using Agilent Technologies 1200 Series, G6130A (Agilent Technologies). Silica gel 60 (Merck) was used as silica gel, amine silica gel DM 1020 (Fuji Silysia Chemical Ltd.) was used as amine silica gel, and YFLC W-prep2XY (Yamazen Corporation) was used as chromatography.

Reference Example 1 Synthesis of 2-chloro-2'-(trifluoromethoxy)-[1,1'-biphenyl]-4-amine

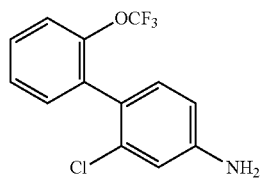 [SMILES: Nc1ccc(-c2ccccc2OC(F)(F)F)c(Cl)c1]

To an acetonitrile (9.0 mL) solution of 2-trifluoromethoxyphenylboronic acid (1.10 g, 5.33 mmol), 4-bromo-3-chloroaniline (1.00 g, 4.84 mmol), potassium carbonate (1.00 g, 7.27 mmol), 1,1'-bis(diphenylphosphino)ferrocene dichloropalladium(II) dichloromethane adduct (0.396 g, 0.484 mmol), and distilled water (3.0 mL) were added at room temperature and the temperature was raised to 90° C., followed by stirring for 18 hours. The reaction solution was filtered through silica gel and then the filtrate was concentrated under reduced pressure. The residue was purified by column chromatography (silica gel, n-hexane/ethyl acetate=85/15 to 67/33) to obtain 2-chloro-2'-(trifluoromethoxy)-[1,1'-biphenyl]-4-amine (hereinafter referred to as the compound of Reference Example 1) (1.03 g, 3.57 mmol, 73.6%) as a yellow oily product.

$^1$H-NMR (400 MHz, CDCl$_3$) δ: 3.79 (s, 2H), 6.62 (dd, J=8.3, 2.3 Hz, 1H), 6.80 (d, J=2.3 Hz, 1H), 7.05 (d, J=8.3 Hz, 1H), 7.30-7.41 (m, 4H).
ESI-MS: m/z=288 (M+H)$^+$.

Reference Example 2 Synthesis of tert-butyl 2-((2-chloro-2'-(trifluoromethoxy)-[1,1'-biphenyl]-4-yl)carbamoyl)piperidine-1-carboxylate

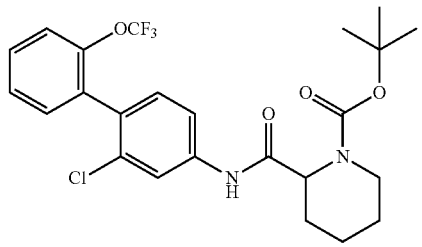 [SMILES: CC(C)(C)OC(=O)N1CCCCC1C(=O)Nc1ccc(-c2ccccc2OC(F)(F)F)c(Cl)c1]

To a DMF (2.0 mL) solution of 1-(tert-butoxycarbonyl)piperidine-2-carboxylic acid (0.263 g, 1.15 mmol), a DMF (2.0 mL) solution of the compound of Reference Example 1 (0.300 g, 1.04 mmol), HATU (0.436 g, 1.15 mmol), and diisopropylethylamine (0.273 mL, 1.56 mmol) were added at room temperature, followed by stirring at the same temperature for 16 hours. To the reaction solution, distilled water was added, and the solution was extracted with a mixed solvent of n-hexane/ethyl acetate=20/80(v/v). The organic layer was washed with saturated brine, dried over anhydrous sodium sulfate and filtered, and then the filtrate was concentrated under reduced pressure. The residue was purified by column chromatography (silica gel, n-hexane/ethyl acetate=90/10 to 67/33) to obtain tert-butyl 2-((2-chloro-2'-(trifluoromethoxy)-[1,1'-biphenyl]-4-yl)carbamoyl)piperidine-1-carboxylate (hereinafter referred to as the compound of Reference Example 2) (0.483 g, 0.968 mmol, 92.8%) as a white solid.

$^1$H-NMR (400 MHz, CDCl$_3$) δ: 1.43-1.51 (m, 2H), 1.53 (s, 9H), 1.60-1.75 (m, 3H), 2.35 (d, J=12.7 Hz, 1H), 2.80-2.89 (m, 1H), 4.03-4.13 (m, 1H), 4.86-4.89 (m, 1H), 7.22 (d, J=8.3 Hz, 1H), 7.29-7.45 (m, 6H), 7.80 (br, 1H).
ESI-MS: m/z=499 (M+H)$^+$.

Reference Example 3 Synthesis of N-(2-chloro-2'-(trifluoromethoxy)-[1,1'-biphenyl]-4-yl)piperidine-2-carboxamide

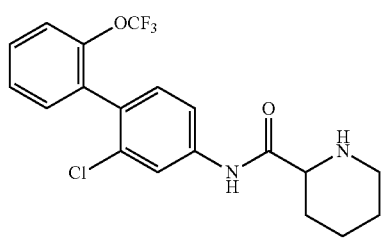 [SMILES: O=C(Nc1ccc(-c2ccccc2OC(F)(F)F)c(Cl)c1)C1CCCCN1]

To a dichloromethane (5.0 mL) solution of the compound of Reference Example 2 (0.483 g, 0.968 mmol), trifluoroacetic acid (0.522 mL, 6.78 mmol) was added at room temperature, followed by stirring at the same temperature for 20 hours. The reaction solution was concentrated under reduced pressure, neutralized with an aqueous potassium carbonate solution, and then extracted with chloroform. The organic layer was dried over anhydrous sodium sulfate and filtered, and then the filtrate was concentrated under reduced pressure. The residue was purified by column chromatography (amine silica gel, n-hexane/ethyl acetate=60/40 to 20/80) to obtain N-(2-chloro-2'-(trifluoromethoxy)-[1,1'-biphenyl]-4-yl)piperidine-2-carboxamide (hereinafter referred to as the compound of Reference Example 3) (0.309 g, 0.775 mmol, 80.0%) as a white solid.

$^1$H-NMR (400 MHz, CDCl$_3$) δ: 1.53 (ddd, J=36.8, 17.9, 8.8 Hz, 4H), 1.78-1.86 (m, 1H), 2.00-2.07 (m, 1H), 2.74-2.82 (m, 1H), 3.03-3.10 (m, 1H), 3.38 (dd, J=9.6, 3.5 Hz, 1H), 7.23 (d, J=8.3 Hz, 1H), 7.31-7.37 (m, 3H), 7.40-7.45 (m, 1H), 7.53 (dd, J=8.3, 2.0 Hz, 1H), 7.82 (d, J=2.2 Hz, 1H), 9.02 (br, 1H). ESI-MS: m/z=399 (M+H)$^+$.

Example 1 Synthesis of 1-acetyl-N-(2-chloro-2'-(trifluoromethoxy)-[1,1'-biphenyl]-4-yl)piperidine-2-carboxamide

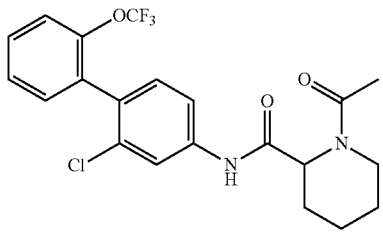 [SMILES: CC(=O)N1CCCCC1C(=O)Nc1ccc(-c2ccccc2OC(F)(F)F)c(Cl)c1]

To a dichloromethane (3.0 mL) solution of the compound of Reference Example 3 (0.0700 g, 0.176 mmol), triethylamine (0.0367 mL, 0.263 mmol) and acetic anhydride (0.0182 mL, 0.193 mmol) were added at 0° C. and the temperature was raised to room temperature, followed by stirring for 1 hour. To the reaction solution, distilled water was added, and the solution was extracted with chloroform. The organic layer was washed with distilled water and saturated brine, dried over anhydrous sodium sulfate and filtered, and then the filtrate was concentrated under reduced pressure. The residue was purified by column chromatography (silica gel, chloroform/methanol=95/5) to obtain 1-acetyl-N-(2-chloro-2'-(trifluoromethoxy)-[1,1'-biphenyl]-4-yl)piperidine-2-carboxamide (hereinafter referred to as the compound of Example 1) (0.0730 g, 0.166 mmol, 94.3%) as a white solid.

$^1$H-NMR (400 MHz, CDCl$_3$) δ: 1.46-1.63 (m, 1H), 1.67 (d, J=7.8 Hz, 1H), 1.89-2.02 (m, 2H), 2.22 (s, 3H), 2.29 (d, J=12.9 Hz, 1H), 3.22 (t, J=13.2 Hz, 1H), 3.78 (d, J=12.7 Hz, 1H), 5.29 (d, J=5.1 Hz, 1H), 7.20 (d, J=8.3 Hz, 1H), 7.29-7.37 (m, 3H), 7.40-7.44 (m, 2H), 7.80 (br, 1H), 8.65 (br, 1H).

ESI-MS: m/z=441 (M+H)$^+$.

Example 2 Synthesis of N-(2-chloro-2'-(trifluoromethoxy)-[1,1'-biphenyl]-4-yl)-1-(2,2,2-trifluoroacetyl)piperidine-2-carboxamide

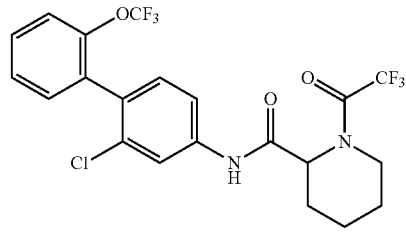

According to the same procedure as in Example 1, except that trifluoroacetic anhydride was used in place of acetic anhydride, N-(2-chloro-2'-(trifluoromethoxy)-[1,1'-biphenyl]-4-yl)-1-(2,2,2-trifluoroacetyl)piperidine-2-carboxamide (hereinafter referred to as the compound of Example 2) (0.0500 g, 0.101 mmol, 99.0%) was obtained as a white solid.

$^1$H-NMR (400 MHz, CDCl$_3$) δ: 1.56-1.86 (m, 4H), 1.98 (dt, J=11.2, 4.6 Hz, 1H), 2.36 (d, J=14.1 Hz, 1H), 3.37 (td, J=13.4, 2.6 Hz, 1H), 4.01 (d, J=13.9 Hz, 1H), 5.18 (d, J=5.4 Hz, 1H), 7.21 (d, J=8.3 Hz, 1H), 7.30-7.46 (m, 5H), 7.79 (br, 1H), 7.89 (br, 1H).

ESI-MS: m/z=495 (M+H)$^+$.

Example 3 Synthesis of N-(2-chloro-2'-(trifluoromethoxy)-[1,1'-biphenyl]-4-yl)-1-propionylpiperidine-2-carboxamide

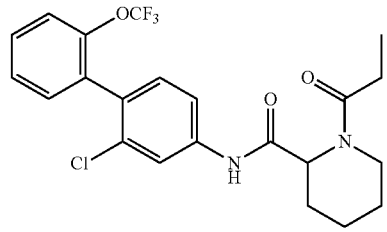 [SMILES: CCC(=O)N1CCCCC1C(=O)Nc1ccc(-c2ccccc2OC(F)(F)F)c(Cl)c1]

To a dichloromethane (2.0 mL) solution of the compound of Reference Example 3 (0.0300 g, 0.0752 mmol), triethylamine (0.0157 mL, 0.113 mmol) and propionyl chloride (0.00719 mL, 0.0828 mmol) were added at 0° C. and the temperature was raised to room temperature, followed by stirring for 30 minutes. To the reaction solution, methanol was added, and the solution was concentrated under reduced pressure. The residue was purified by column chromatography (silica gel, chloroform/methanol=100/0 to 90/10) to obtain N-(2-chloro-2'-(trifluoromethoxy)-[1,1'-biphenyl]-4-yl)-1-propionylpiperidine-2-carboxamide (hereinafter referred to as the compound of Example 3) (0.0340 g, 0.0747 mmol, 99.4%) as a white solid.

$^1$H-NMR (400 MHz, CDCl$_3$) δ: 1.22 (t, J=7.3 Hz, 3H), 1.55 (br, 2H), 1.76 (br, 2H), 1.97 (t, J=13.2 Hz, 1H), 2.30 (d, J=12.7 Hz, 1H), 2.48 (dq, J=6.6, 2.0 Hz, 2H), 3.12 (td, J=13.2, 2.8 Hz, 1H), 3.83 (d, J=13.2 Hz, 1H), 5.29 (d, J=5.4 Hz, 1H), 7.20 (d, J=8.3 Hz, 1H), 7.29-7.36 (m, 4H), 7.39-7.45 (m, 1H), 7.84 (br, 1H), 8.56 (br, 1H).

ESI-MS: m/z=455 (M+H)$^+$.

Example 4 Synthesis of N-(2-chloro-2'-(trifluoromethoxy)-[1,1'-biphenyl]-4-yl)-1-(2-methoxyacetyl)piperidine-2-carboxamide

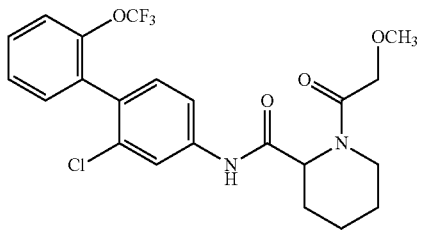 [SMILES: COCC(=O)N1CCCCC1C(=O)Nc1ccc(-c2ccccc2OC(F)(F)F)c(Cl)c1]

To a DMF (0.5 mL) solution of 2-methoxyacetic acid (0.00693 ml, 0.0903 mmol), a DMF (0.5 mL) solution of the compound of Reference Example 3 (0.0300 g, 0.0752 mmol), HATU (0.0343 g, 0.0902 mmol) and diisopropylethylamine (0.0197 mL, 0.113 mmol) were added at room temperature, followed by stirring at the same temperature for 3 hours. To the reaction solution, distilled water was added, and the solution was extracted with a mixed solvent of n-hexane/ethyl acetate=20/80. The organic layer was washed with saturated brine, dried over anhydrous sodium sulfate and filtered, and then the filtrate was concentrated under reduced pressure. The residue was purified by column chromatography (silica gel, n-hexane/ethyl acetate=50/50 to 0/100) to obtain N-(2-chloro-2'-(trifluoromethoxy)-[1,1'-biphenyl]-4-yl)-1-(2-methoxyacetyl)piperidine-2-carboxamide (hereinafter referred to as the compound of Example 4) (0.0266 g, 0.0565 mmol, 74.6%) as a white solid.

$^1$H-NMR (400 MHz, CDCl$_3$) δ: 1.58-2.00 (m, 5H), 2.33 (d, J=14.4 Hz, 0.8H), 2.48 (d, J=12.7 Hz, 0.2H), 2.63 (t, J=12.7 Hz, 0.2H), 3.14 (t, J=13.0 Hz, 0.8H), 3.48 (s, 2.4H), 3.51 (s, 0.6H), 3.82 (d, J=12.7 Hz, 0.8H), 4.12 (d, J=11.7 Hz, 0.2H), 4.18 (d, J=13.9 Hz, 0.8H), 4.26 (d, J=13.9 Hz, 0.8H), 4.34 (d, J=11.7 Hz, 0.2H), 4.52-4.60 (m, 0.2H), 4.64-4.68 (m, 0.2H), 5.23 (d, J=6.1 Hz, 0.8H), 7.20 (d, J=8.3 Hz, 1H), 7.28-7.45 (m, 5H), 7.65-7.90 (m, 1H), 8.46 (br, 0.8H), 8.57 (br, 0.2H).
ESI-MS: m/z=471 (M+H)$^+$.

Example 5 Synthesis of N-(2-chloro-2'-(trifluoromethoxy)-[1,1'-biphenyl]-4-yl)-1-(2-hydroxyacetyl)piperidine-2-carboxamide

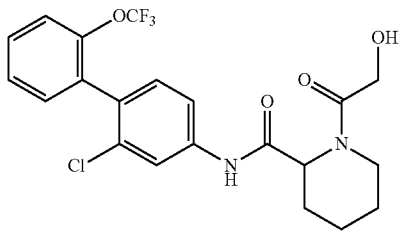 [SMILES: O=C(Nc1ccc(-c2ccccc2OC(F)(F)F)c(Cl)c1)C1CCCCN1C(=O)CO]

According to the same procedure as in Example 4, except that glycolic acid was used in place of 2-methoxyacetic acid, N-(2-chloro-2'-(trifluoromethoxy)-[1,1'-biphenyl]-4-yl)-1-(2-hydroxyacetyl)piperidine-2-carboxamide (hereinafter referred to as the compound of Example 5) (0.0114 g, 0.0250 mmol, 33.2%) was obtained as a white solid.

$^1$H-NMR (400 MHz, CDCl$_3$) δ: 1.48-1.55 (m, 1H), 1.63-1.71 (m, 1H), 1.75-1.85 (m, 2H), 1.91-2.02 (m, 1H), 2.32 (d, J=13.4 Hz, 1H), 3.17-3.25 (m, 1H), 3.43-3.53 (m, 2H), 4.28-4.32 (m, 2H), 5.26 (d, J=5.6 Hz, 1H), 7.22 (d, J=8.3 Hz, 1H), 7.30-7.45 (m, 51H), 7.77 (br, 1H), 8.14 (br, 1H).
ESI-MS: m/z=457 (M+H)+.

Example 6 Synthesis of N-(2-chloro-2'-(trifluoromethoxy)-[1,1'-biphenyl]-4-yl)-1-(2-(dimethylamino)acetyl)piperidine-2-carboxamide

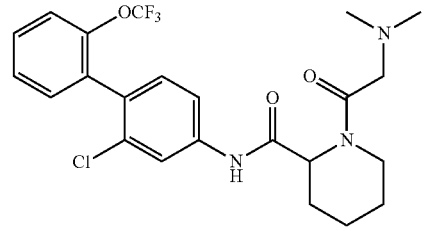 [SMILES: CN(C)CC(=O)N1CCCCC1C(=O)Nc1ccc(-c2ccccc2OC(F)(F)F)c(Cl)c1]

According to the same procedure as in Example 4, except that N,N-dimethylglycine hydrochloride was used in place of 2-methoxyacetic acid, N-(2-chloro-2'-(trifluoromethoxy)-[1,1'-biphenyl]-4-yl)-1-(2-(dimethylamino)acetyl)piperidine-2-carboxamide (hereinafter referred to as the compound of Example 6) (0.0273 g, 0.0564 mmol, 90.0%) was obtained as a white solid.

$^1$H-NMR (400 MHz, CDCl$_3$) δ: 1.40-2.20 (m, 6H), 2.34 (s, 3H), 2.47-2.50 (m, 3.4H), 2.56-2.64 (m, 0.411), 2.92 (d, J=12.6 Hz, 0.6H), 3.06-3.14 (m, 0.4H), 3.24 (s, 0.6H), 3.67 (d, J=12.6 Hz, 0.6H), 4.03-4.07 (m, 0.4H), 4.54-4.62 (m, 1.2H), 5.24-5.27 (m, 0.4H), 7.19-7.23 (m, 1H), 7.30-7.46 (m, 5H), 7.73-7.75 (m, 1H), 8.53 (br, 0.4H), 10.69 (br, 0.6H).
ESI-MS: m/z=484 (M+H)$^+$.

Example 7 Synthesis of N-(2-chloro-2'-(trifluoromethoxy)-[1,1'-biphenyl]-4-yl)-1-(2,2-difluoroacetyl)piperidine-2-carboxamide

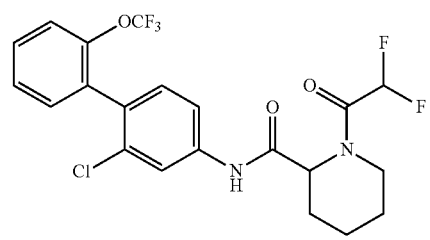 [SMILES: O=C(Nc1ccc(-c2ccccc2OC(F)(F)F)c(Cl)c1)C1CCCCN1C(=O)C(F)F]

According to the same procedure as in Example 4, except that difluoroacetic acid was used in place of 2-methoxyacetic acid, N-(2-chloro-2'-(trifluoromethoxy)-[1,1'-biphenyl]-4-yl)-1-(2,2-difluoroacetyl)piperidine-2-carboxamide (hereinafter referred to as the compound of Example 7) (0.0212 g, 0.0444 mmol, 59.1%) was obtained as a white solid.

$^1$H-NMR (400 MHz, DMSO-D$_6$) δ: 1.40-1.80 (m, 5.0H), 2.21-2.24 (m, 0.7H), 2.29-2.34 (m, 0.3H), 2.65-2.68 (m, 0.3H), 3.46-3.55 (m, 0.7H), 3.82-3.88 (m, 0.7H), 4.28-4.34 (m, 0.3H), 4.79-4.81 (m, 0.3H), 5.07-5.10 (m, 0.7H), 6.73 (t, J=52.6 Hz, 0.3H), 6.83 (t, J=52.7 Hz, 0.7H), 7.32 (d, J=8.3

Hz, 1H), 7.39-7.43 (m, 1H), 7.45-7.51 (m, 2H), 7.53-7.60 (m, 2H), 7.90-7.93 (m, 1H), 10.19 (br, 0.3H), 10.25 (br, 0.7H).

ESI-MS: m/z=477 (M+H)+.

Example 8 Synthesis of N-(2-chloro-2'-(trifluoromethoxy)-[1,1'-biphenyl]-4-yl)-1-(2-(trifluoromethoxy)acetyl)piperidine-2-carboxamide

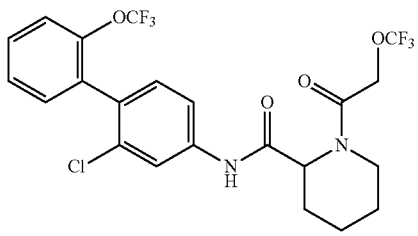 [SMILES: O=C(Nc1ccc(-c2ccccc2OC(F)(F)F)c(Cl)c1)C1CCCCN1C(=O)COC(F)(F)F]

According to the same procedure as in Example 4, except that 2-trifluoromethoxyacetic acid was used in place of 2-methoxyacetic acid, N-(2-chloro-2'-(trifluoromethoxy)-[1,1'-biphenyl]-4-yl)-1-(2-(trifluoromethoxy)acetyl)piperidine-2-carboxamide (hereinafter referred to as the compound of Example 8) (0.00890 g, 0.0170 mmol, 16.9%) was obtained as a white solid.

$^1$H-NMR (400 MHz, CDCl$_3$) δ: 1.55-1.71 (m, 2H), 1.76-1.84 (m, 2H), 1.94-2.03 (m, 1H), 2.32 (d, J=14.5 Hz, 1H), 3.29 (td, J=13.1, 2.7 Hz, 1H), 3.67 (d, J=12.7 Hz, 1H), 4.68-4.76 (m, 2H), 5.22 (d, J=5.4 Hz, 1H), 7.21-7.45 (m, 6H), 7.81 (br, 1H), 8.26 (s, 1H).

ESI-MS: m/z=523 (M−H)⁻.

Reference Example 4 Synthesis of tert-butyl (2-(2-((2-chloro-2'-(trifluoromethoxy)-[1,1'-biphenyl]-4-yl)carbamoyl)piperidin-1-yl)-2-oxoethyl)carbamate

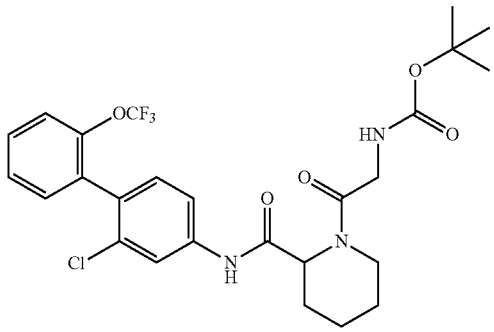 [SMILES: CC(C)(C)OC(=O)NCC(=O)N1CCCCC1C(=O)Nc1ccc(-c2ccccc2OC(F)(F)F)c(Cl)c1]

According to the same procedure as in Example 4, except that 2-((tert-butoxycarbonyl)amino)acetic acid was used in place of 2-methoxyacetic acid, tert-butyl (2-(2-((2-chloro-2'-(trifluoromethoxy)-[1,1'-biphenyl]-4-yl)carbamoyl)piperidin-1-yl)-2-oxoethyl)carbamate (hereinafter referred to as the compound of Reference Example 4) (0.116 g, 0.208 mmol, quantitative) was obtained as a white solid.

$^1$H-NMR (400 MHz, CDCl$_3$) δ: 1.46 (s, 9H), 1.45-1.90 (m, 5H), 2.38 (d, J=13.2 Hz, 1H), 3.21 (t, J=12.1 Hz, 1H), 3.75 (d, J=13.9 Hz, 1H), 3.95 (dd, J=16.7, 5.0 Hz, 1H), 4.09-4.15 (m, 1H), 5.32 (d, J=4.9 Hz, 1H), 5.42 (br, 1H), 7.21 (d, J=8.3 Hz, 1H), 7.29-7.36 (m, 3H), 7.40-7.45 (m, 1H), 7.52 (br, 1H), 7.80 (br, 1H), 8.31 (br, 1H).

ESI-MS: m/z=556 (M+H)+.

Reference Example 5 Synthesis of 1-(2-aminoacetyl)-N-(2-chloro-2'-(trifluoromethoxy)-[1,1'-biphenyl]-4-yl)piperidine-2-carboxamide

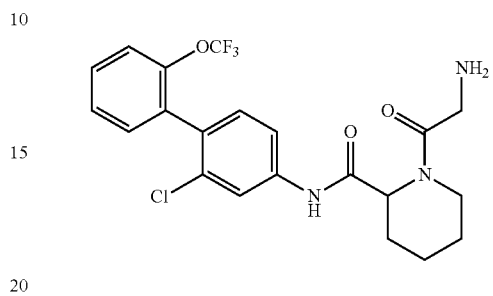

To a dichloromethane (1.0 mL) solution of the compound of Reference Example 4 (0.115 g, 0.207 mmol), trifluoroacetic acid (0.112 mL, 1.45 mmol) was added at room temperature, followed by stirring at the same temperature for 15 hours. The reaction solution was concentrated under reduced pressure, neutralized with an aqueous potassium carbonate solution, and then extracted with chloroform. The organic layer was dried over anhydrous sodium sulfate and filtered, and then the filtrate was concentrated under reduced pressure. The residue was purified by column chromatography (amine silica gel, chloroform/methanol=100/0 to 96/4) to obtain 1-(2-aminoacetyl)-N-(2-chloro-2'-(trifluoromethoxy)-[1,1'-biphenyl]-4-yl)piperidine-2-carboxamide (hereinafter referred to as the compound of Reference Example 5) (0.0613 g, 0.134 mmol, 65.0%) as a white solid.

$^1$H-NMR (400 MHz, CDCl$_3$) δ: 1.45-1.63 (m, 2H), 1.70-1.81 (m, 2H), 1.89-1.99 (m, 1H), 2.31 (d, J=14.0 Hz, 1H), 3.16 (td, J=14.0, 2.3 Hz, 1H), 3.60 (d, J=1.0 Hz, 2H), 3.68 (d, J=14.0 Hz, 1H), 5.27 (d, J=5.4 Hz, 1H), 7.21 (d, J=8.3 Hz, 1H), 7.30-7.45 (m, 5H), 7.77 (br, 1H), 8.39 (br, 1H).

ESI-MS: m/z=456 (M+H)⁺.

Reference Example 6 Synthesis of tert-butyl (2-(2-((2-chloro-2'-(trifluoromethoxy)-[1,1'-biphenyl]-4-yl)carbamoyl)piperidin-1-yl)-2-oxoethyl)(methyl)carbamate

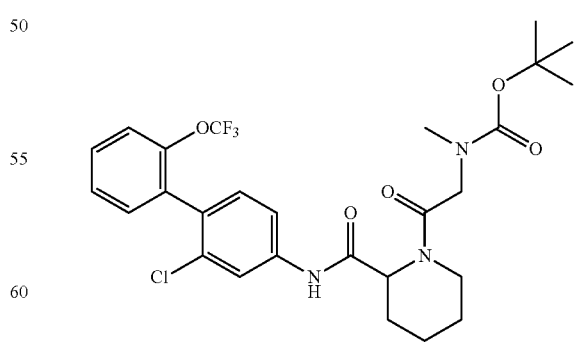

According to the same procedure as in Example 4, except that N-(tert-butoxycarbonyl)-N-methylglycine was used in place of 2-methoxyacetic acid, tert-butyl (2-(2-((2-chloro-2'-(trifluoromethoxy)-[1,1'-biphenyl]-4-yl)carbamoyl)piperidin-1-yl)-2-oxoethyl)(methyl)carbamate (hereinafter referred to as the compound of Reference Example 6) (0.132 g, 0.232 mmol, 92.6%) was obtained as a white solid.

$^1$H-NMR (400 MHz, CDCl$_3$) G: 1.57 (s, 9H), 1.38-1.80 (m, 5H), 2.46-2.53 (m, 1H), 3.05 (s, 3H), 3.15-3.22 (m, 1H), 3.66 (d, J=15.7 Hz, 1H), 3.77-3.84 (m, 1H), 4.41 (d, J=15.7 Hz, 1H), 5.41-5.44 (m, 1H), 7.19 (d, J=8.3 Hz, 1H), 7.28-7.44 (m, 4H), 7.70 (br, 1H), 7.88 (br, 1H), 8.61 (br, 1H).

ESI-MS: m/z=571 (M+H)$^+$.

Example 9 Synthesis of 1-(2-acetamideacetyl)-N-(2-chloro-2'-(trifluoromethoxy)-[1,1'-biphenyl]-4-yl)piperidine-2-carboxamide

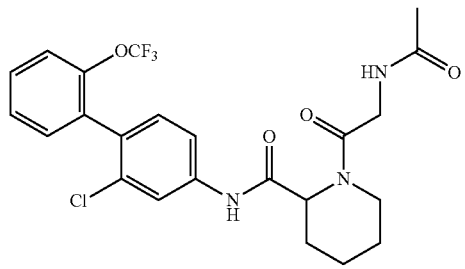 [SMILES: CC(=O)NCC(=O)N1CCCCC1C(=O)Nc1ccc(-c2ccccc2OC(F)(F)F)c(Cl)c1]

According to the same procedure as in Example 3, except that the compound of Reference Example 5 was used in place of the compound of Reference Example 3 and acetyl chloride was used in place of propionyl chloride, 1-(2-acetamideacetyl)-N-(2-chloro-2'-(trifluoromethoxy)-[1,1'-biphenyl]-4-yl)piperidine-2-carboxamide (hereinafter referred to as the compound of Example 9) (0.0274 g, 0.0550 mmol, 80.9%) was obtained as a white solid.

$^1$H-NMR (400 MHz, CDCl$_3$) δ: 1.50-1.90 (m, 5H), 2.09 (s, 3H), 2.37 (d, J=14.4 Hz, 1H), 3.25 (td, J=13.0, 2.4 Hz, 1H), 3.75 (d, J=12.4 Hz, 1H), 4.11 (dd, J=17.2, 4.0 Hz, 1H), 4.21 (dd, J=17.2, 4.0 Hz, 1H), 5.29 (d, J=5.1 Hz, 1H), 6.53 (br, 1H), 7.21 (d, J=8.5 Hz, 1H), 7.29-7.37 (m, 3H), 7.40-7.48 (m, 2H), 7.80 (br, 1H), 8.26 (br, 1H).

ESI-MS: m/z=498 (M+H)$^-$.

Example 10 Synthesis of N-(2-chloro-2'-(trifluoromethoxy)-[1,1'-biphenyl]-4-yl)-1-(2-(methylsulfonamide)acetyl)piperidine-2-carboxamide

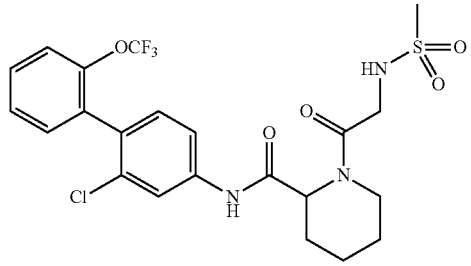 [SMILES: CS(=O)(=O)NCC(=O)N1CCCCC1C(=O)Nc1ccc(-c2ccccc2OC(F)(F)F)c(Cl)c1]

According to the same procedure as in Example 3, except that the compound of Reference Example 5 was used in place of the compound of Reference Example 3 and methanesulfonyl chloride was used in place of propionyl chloride, N-(2-chloro-2'-(trifluoromethoxy)-[1,1'-biphenyl]-4-yl)-1-(2-(methylsulfonamide)acetyl)piperidine-2-carboxamide (hereinafter referred to as the compound of Example 10) (0.0202 g, 0.0378 mmol, 79.2%) was obtained as a white solid.

$^1$H-NMR (400 MHz, CDCl$_3$) δ: 1.52-1.95 (m, 5H), 2.32 (d, J=14.1 Hz, 1H), 3.02 (s, 3H), 3.33 (t, J=12.8 Hz, 1H), 3.64 (d, J=13.0 Hz, 1H), 4.08 (d, J=4.6 Hz, 2H), 5.25 (d, J=4.6 Hz, 1H), 5.48 (br, 1H), 7.22 (d, J=8.3 Hz, 1H), 7.29-7.45 (m, 5H), 7.81 (br, 1H), 8.09 (br, 1H).

ESI-MS: m/z=534 (M+H)+.

Example 11 Synthesis of N-(2-chloro-2'-(trifluoromethoxy)-[1,1'-biphenyl]-4-yl)-1-(2-(methylamino)acetyl)piperidine-2-carboxamide

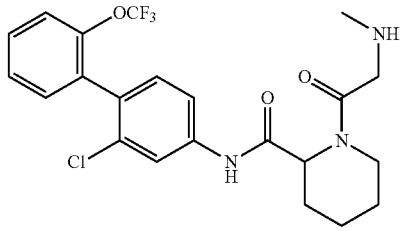 [SMILES: CNCC(=O)N1CCCCC1C(=O)Nc1ccc(-c2ccccc2OC(F)(F)F)c(Cl)c1]

According to the same procedure as in Reference Example 5, except that the compound of Reference Example 6 was used in place of the compound of Reference Example 4, N-(2-chloro-2'-(trifluoromethoxy)-[1,1'-biphenyl]-4-yl)-1-(2-(methylamino)acetyl)piperidine-2-carboxamide (hereinafter referred to as the compound of Example 11) (0.0799 g, 0.170 mmol, 73.4%) was obtained as a white solid.

$^1$H-NMR (400 MHz, CDCl$_3$) δ: 1.26-1.76 (m, 5H), 1.90-2.06 (m, 1H), 2.28-2.42 (m, 1H), 2.50 (s, 2.4H), 2.60-2.63 (m, 0.8H), 3.15 (t, J=12.2 Hz, 0.8H), 3.43 (d, J=12.7 Hz, 0.2H), 3.52 (s, 1.6H), 3.70-3.76 (m, 1H), 4.58-4.63 (m, 0.4H), 5.28 (d, J=4.9 Hz, 0.8H), 7.19-7.23 (m, 1H), 7.30-7.45 (m, 5H), 7.75-7.77 (m, 1H), 8.44 (s, 0.8H), 10.49 (s, 0.2H).

ESI-MS: m/z=470 (M+H)$^+$.

Example 12 Synthesis of N-(2-chloro-2'-(trifluoromethoxy)-[1,1'-biphenyl]-4-yl)-1-(2-(N-methylacetamide)acetyl)piperidine-2-carboxamide

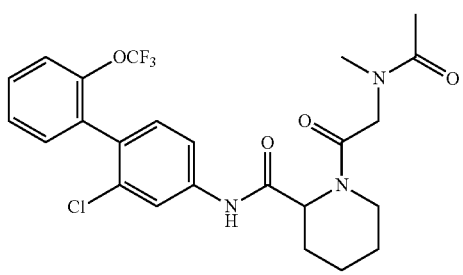 [SMILES: CC(=O)N(C)CC(=O)N1CCCCC1C(=O)Nc1ccc(-c2ccccc2OC(F)(F)F)c(Cl)c1]

According to the same procedure as in Example 3, except that the compound of Example 11 was used in place of the compound of Reference Example 3 and acetyl chloride was used in place of propionyl chloride, N-(2-chloro-2'-(trifluoromethoxy)-[1,1'-biphenyl]-4-yl)-1-(2-(N-methylacetamide)acetyl)piperidine-2-carboxamide (hereinafter referred to as the compound of Example 12) (0.0261 g, 0.0510 mmol, 95.8%) was obtained as a white solid.

¹H-NMR (400 MHz, CDCl₃) δ: 1.48-1.76 (m, 5H), 2.20 (s, 3H), 2.50-2.65 (m, 1H), 3.24 (s, 2.1H), 3.30 (s, 0.9H), 3.20-3.31 (m, 1H), 3.34 (d, J=15.0 Hz, 0.3H), 3.63 (d, J=15.0 Hz, 0.7H), 3.83-3.89 (m, 0.7H), 4.60 (d, J=15.0 Hz, 0.7H), 4.64-4.70 (m, 0.6H), 4.78 (d, J=15.0 Hz, 0.3H), 5.41 (d, J=4.5 Hz, 0.7H), 7.20-7.22 (m, 1H), 7.30-7.35 (m, 3H), 7.39-7.44 (m, 1H), 7.60-7.75 (m, 0.7H), 7.77 (dd, J=8.4, 2.0 Hz, 0.3H), 7.98-8.07 (m, 0.7H), 8.14 (d, J=1.8 Hz, 0.3H), 8.64 (br, 0.7H), 9.63 (br, 0.3H).
ESI-MS: m/z=512 (M+H)⁺.

Example 13 Synthesis of N-(2-chloro-2'-(trifluoromethoxy)-[1,1'-biphenyl]-4-yl)-1-(2-(N-methylmethylsulfonamide)acetyl)piperidine-2-carboxamide

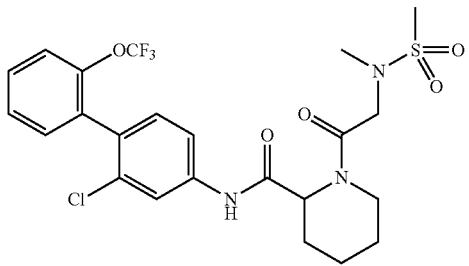 [SMILES: CN(CC(=O)N1CCCCC1C(=O)Nc1ccc(-c2ccccc2OC(F)(F)F)c(Cl)c1)S(C)(=O)=O]

According to the same procedure as in Example 3, except that the compound of Example 11 was used in place of the compound of Reference Example 3 and methanesulfonyl chloride was used in place of propionyl chloride, N-(2-chloro-2'-(trifluoromethoxy)-[1,1'-biphenyl]-4-yl)-1-(2-(N-methylmethylsulfonamide)acetyl)piperidine-2-carboxamide (hereinafter referred to as the compound of Example 13) (0.0264 g, 0.0482 mmol, 90.6%) was obtained as a white solid.

¹H-NMR (400 MHz, CDCl₃) δ: 1.52-1.89 (m, 5H), 2.35-2.38 (m, 1H), 3.03-3.07 (m, 6H), 3.20-3.31 (m, 1H), 3.67-3.76 (m, 1H), 4.16-4.27 (m, 2H), 5.25-5.26 (m, 1H), 7.21-7.23 (m, 1H), 7.30-7.45 (m, 5H), 7.83 (s, 1H), 8.22 (br, 1H).
ESI-MS: m/z=548 (M+H)⁺.

Example 14 Synthesis of N-(2-chloro-2'-(trifluoromethoxy)-[1,1'-biphenyl]-4-yl)-1-(ethylsulfonyl)piperidine-2-carboxamide

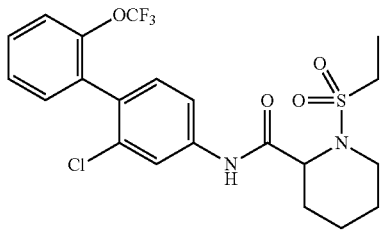 [SMILES: CCS(=O)(=O)N1CCCCC1C(=O)Nc1ccc(-c2ccccc2OC(F)(F)F)c(Cl)c1]

According to the same procedure as in Example 3, except that ethanesulfonyl chloride was used in place of propionyl chloride, N-(2-chloro-2'-(trifluoromethoxy)-[1,1'-biphenyl]-4-yl)-1-(ethylsulfonyl)piperidine-2-carboxamide (hereinafter referred to as the compound of Example 14) (0.0660 g, 0.134 mmol, 99.3%) was obtained as a white solid.

¹H-NMR (400 MHz, CDCl₃) δ: 1.47 (t, J=7.4 Hz, 3H), 1.58-1.68 (m, 2H), 1.69-1.84 (m, 3H), 2.59 (d, J=12.4 Hz, 1H), 3.06-3.21 (m, 4H), 3.88 (d, J=12.0 Hz, 1H), 4.56 (d, J=8.3 Hz, 1H), 7.24 (d, J=8.3 Hz, 1H), 7.31-7.38 (m, 3H), 7.40-7.50 (m, 2H), 7.85 (s, 1H), 8.53 (br, 1H).
ESI-MS: m/z=491 (M+H)⁺.

Example 15 Synthesis of N-(2-chloro-2'-(trifluoromethoxy)-[1,1'-biphenyl]-4-yl)-1-(methylsulfonyl)piperidine-2-carboxamide

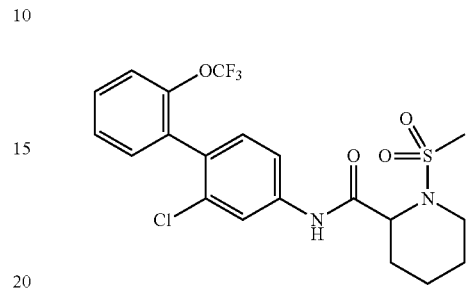

According to the same procedure as in Example 3, except that methanesulfonyl chloride was used in place of propionyl chloride, N-(2-chloro-2'-(trifluoromethoxy)-[1,1'-biphenyl]-4-yl)-1-(methylsulfonyl)piperidine-2-carboxamide (hereinafter referred to as the compound of Example 15) (0.0800 g, 0.168 mmol, 66.9%) was obtained as a white solid.

¹H-NMR (400 MHz, CDCl₃) δ: 1.47-1.61 (m, 1H), 1.62-1.81 (m, 4H), 2.45 (d, J=10.4 Hz, 1H), 3.04 (s, 3H), 3.23 (td, J=13.3, 2.4 Hz, 1H), 3.93 (t, J=7.0 Hz, 1H), 4.64 (br, 1H), 7.25 (d, J=8.5 Hz, 1H), 7.30-7.38 (m, 3H), 7.43 (dt, J=10.8, 3.7 Hz, 2H), 7.84 (d, J=2.2 Hz, 1H), 8.29 (br, 1H).
ESI-MS: m/z=477 (M+H)⁺.

Example 16 Synthesis of N-(2-chloro-2'-(trifluoromethoxy)-[1,1'-biphenyl]-4-yl)-1-formylpiperidine-2-carboxamide

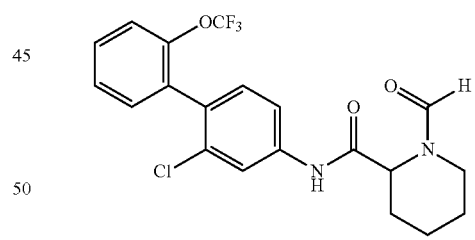

To a dichloromethane (1.0 mL) solution of the compound of Reference Example 3 (0.0400 g, 0.100 mmol), ethyl formate (0.567 mL, 7.02 mmol) was added at 0° C. and the temperature was raised to 90° C., followed by stirring for 18 hours. The reaction solution was concentrated under reduced pressure and the residue was purified by column chromatography (silica gel, chloroform/methanol=100/0 to 90/10) to obtain N-(2-chloro-2'-(trifluoromethoxy)-[1,1'-biphenyl]-4-yl)-1-formylpiperidine-2-carboxamide (hereinafter referred to as the compound of Example 16) (0.0300 g, 0.0703 mmol, 70.1%) as a white solid.

¹H-NMR (400 MHz, CDCl₃) δ: 1.42-1.64 (m, 2H), 1.82 (d, J=10.0 Hz, 2H), 1.95 (dt, J=8.8, 4.3 Hz, 1H), 2.35 (d,

J=13.9 Hz, 1H), 3.29 (td, J=13.2, 2.8 Hz, 1H), 3.63 (d, J=9.5 Hz, 1H), 5.12 (d, J=5.6 Hz, 1H), 7.21 (d, J=8.3 Hz, 1H), 7.28-7.45 (m, 5H), 7.80 (br, 1H), 8.21 (d, J=9.2 Hz, 1H), 8.32 (br, 1H).

ESI-MS: m/z=427 (M+H)⁺.

Example 17 Synthesis of N²-(2-chloro-2'-(trifluoromethoxy)-[1,1'-biphenyl]-4-yl)piperidine-1,2-dicarboxamide

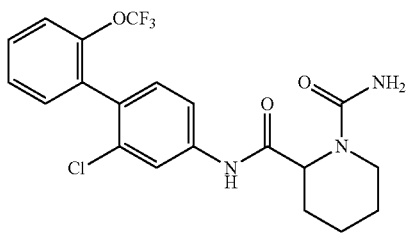

To a dichloromethane (3.0 mL) solution of the compound of Reference Example 3 (0.100 g, 0.251 mmol), trimethylsilyl isocyanate (0.0333 mL, 0.251 mmol) and triethylamine (0.0349 mL, 0.251 mmol) were added at 0° C. and the temperature was raised to room temperature, followed by stirring for 72 hours. To the reaction solution, methanol was added, and the solution was concentrated under reduced pressure. The residue was purified by column chromatography (silica gel, chloroform) to obtain N²-(2-chloro-2'-(trifluoromethoxy)-[1,1'-biphenyl]-4-yl)piperidine-1,2-dicarboxamide (hereinafter referred to as the compound of Example 17) (0.0300 g, 0.0679 mmol, 27.1%) as a white solid.

¹H-NMR (400 MHz, CDCl₃) δ: 1.50-1.68 (m, 2H), 1.73 (br, 2H), 1.81-1.92 (m, 1H), 2.30 (d, J=12.9 Hz, 1H), 3.21 (dt, J=12.8, 2.6 Hz, 1H), 3.52 (d, J=13.2 Hz, 1H), 4.81 (br, 2H), 5.03 (d, J=4.6 Hz, 1H), 7.20 (d, J=8.3 Hz, 1H), 7.29-7.37 (m, 3H), 7.42 (dt, J=10.8, 3.8 Hz, 2H), 7.81 (br, 1H), 8.95 (br, 1H).

ESI-MS: m/z=442 (M+H)⁺.

Example 18 Synthesis of N²-(2-chloro-2'-(trifluoromethoxy)-[1,1'-biphenyl]-4-yl)-N',N' dimethylpiperidine-1,2-dicarboxamide

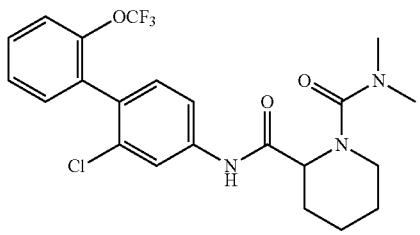 [SMILES: CN(C)C(=O)N1CCCCC1C(=O)Nc1ccc(-c2ccccc2OC(F)(F)F)c(Cl)c1]

According to the same procedure as in Example 3, except that dimethylcarbamoyl chloride was used in place of propionyl chloride, N²-(2-chloro-2'-(trifluoromethoxy)-[1,1'-biphenyl]-4-yl)-N¹,N¹-dimethylpiperidine-1,2-dicarboxamide (hereinafter referred to as the compound of Example 18) (0.0231 g, 0.0492 mmol, 65.4%) was obtained as a white solid.

¹H-NMR (400 MHz, CDCl₃) δ: 1.48-1.78 (m, 4H), 1.92-2.05 (m, 1H), 2.27-2.35 (m, 1H), 2.94 (s, 6H), 2.87-2.99 (m, 1H), 3.40-3.46 (m, 1H), 4.47-4.51 (m, 1H), 7.20 (d, J=8.6 Hz, 1H), 7.30-8.00 (m, 6H), 10.60 (br, 1H).

ESI-MS: m/z=470 (M+H).

Example 19 Synthesis of methyl 2-((2-chloro-2'-(trifluoromethoxy)-[1,1'-biphenyl]-4-yl)carbamoyl)piperidine-1-carboxylate

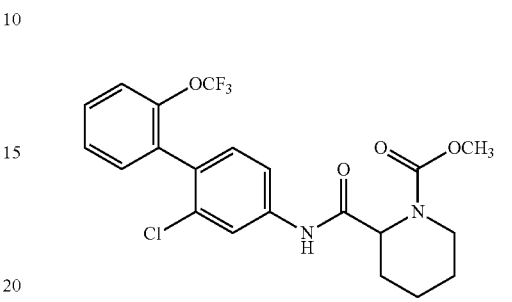

According to the same procedure as in Example 3, except that methyl chloroformate was used as propionyl chloride, methyl 2-((2-chloro-2'-(trifluoromethoxy)-[1,1'-biphenyl]-4-yl)carbamoyl)piperidine-1-carboxylate (hereinafter referred to as the compound of Example 19) (0.0316 g, 0.0692 mmol, 92.0%) was obtained as a white solid.

¹H-NMR (400 MHz, CDCl₃) δ: 1.46-1.78 (m, 5H), 2.30-2.41 (m, 1H), 2.92 (t, J=12.1 Hz, 1H), 3.81 (s, 3H), 4.05-4.20 (br, 1H), 4.93 (d, J=4.6 Hz, 1H), 7.23 (d, J=8.5 Hz, 1H), 7.31-7.45 (m, 5H), 7.74-7.86 (m, 1H), 8.21 (br, 1H).

ESI-MS: m/z=457 (M+H)⁺.

Reference Example 7 Synthesis of tert-butyl (R)-2-((2-chloro-2'-(trifluoromethoxy)-[1,1'-biphenyl]-4-yl)carbamoyl)piperidine-1-carboxylate

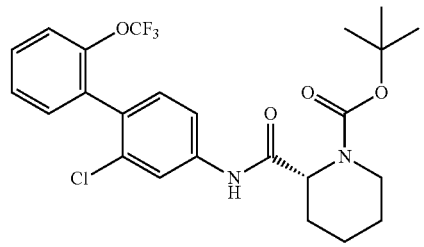 [SMILES: CC(C)(C)OC(=O)N1CCCC[C@@H]1C(=O)Nc1ccc(-c2ccccc2OC(F)(F)F)c(Cl)c1]

To a DMF (18 mL) solution of (R)-(+)-1-(tert-butoxycarbonyl)piperidine-2-carboxylic acid (0.840 g, 3.66 mmol), the compound of Reference Example 1 (1.05 g, 3.66 mmol), HATU (1.53 g, 4.03 mmol), and diisopropylethylamine (0.768 mL, 4.40 mmol) were added at room temperature, followed by stirring at the same temperature for 18 hours. To the reaction solution, distilled water was added, and the solution was extracted with ethyl acetate. The organic layer was washed with saturated brine, dried over anhydrous sodium sulfate and filtered, and then the filtrate was concentrated under reduced pressure. The residue was purified by column chromatography (silica gel, n-hexane/ethyl acetate=80/20) to obtain tert-butyl (R)-2-((2-chloro-2'-(trifluoromethoxy)-[1,1'-biphenyl]-4-yl)carbamoyl)piperidine-1-carboxylate (hereinafter referred to as the compound of Reference Example 7) (1.60 g, 3.20 mmol, 87.3%) as a white solid.

$^1$H-NMR (400 MHz, CDCl$_3$) δ: 1.43-1.51 (m, 2H), 1.53 (s, 9H), 1.60-1.75 (m, 3H), 2.35 (d, J=12.7 Hz, 1H), 2.80-2.89 (m, 1H), 4.03-4.13 (m, 1H), 4.86-4.89 (m, 1H), 7.22 (d, J=8.3 Hz, 1H), 7.29-7.45 (m, 6H), 7.80 (br, 1H).
ESI-MS: m/z=499 (M+H)$^+$.

Reference Example 8 Synthesis of (R)—N-(2-chloro-2'-(trifluoromethoxy)-[1,1'-biphenyl]-4-yl)piperidine-2-carboxamide

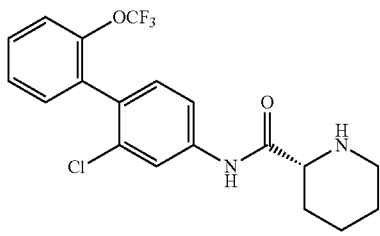

To a dichloromethane (30 mL) solution of the compound of Reference Example 7 (1.60 g, 3.21 mmol), trifluoroacetic acid (8.02 mL, 104 mmol) was added at room temperature, followed by stirring at the same temperature for 2 hours. To the reaction solution, distilled water was added, and the solution was extracted with chloroform. The aqueous layer was neutralized by adding an aqueous 1M sodium hydroxide solution and then extracted with chloroform. The organic layer was washed with distilled water and saturated brine, dried over anhydrous sodium sulfate, and filtered, and then the filtrate was concentrated under reduced pressure to obtain (R)—N-(2-chloro-2'-(trifluoromethoxy)-[1,1'-biphenyl]-4-yl)piperidine-2-carboxamide (hereinafter referred to as the compound of Reference Example 8) (1.13 g, 2.84 mmol, 88.6%) as a white solid.
$^1$H-NMR (400 MHz, CDCl$_3$) δ: 1.53 (ddd, J=36.8, 17.9, 8.8 Hz, 4H), 1.78-1.86 (m, 1H), 2.00-2.07 (m, 1H), 2.74-2.82 (m, 1H), 3.03-3.10 (m, 1H), 3.38 (dd, J=9.6, 3.5 Hz, 1H), 7.23 (d, J=8.3 Hz, 1H), 7.31-7.37 (m, 3H), 7.40-7.45 (m, 1H), 7.53 (dd, J=8.3, 2.0 Hz, 1H), 7.82 (d, J=2.2 Hz, 1H), 9.02 (br, 1H).
ESI-MS: m/z=399 (M+H)$^+$.

Example 20 Synthesis of (R)-1-acetyl-N-(2-chloro-2'-(trifluoromethoxy)-[1,1'-biphenyl]-4-yl)piperidine-2-carboxamide

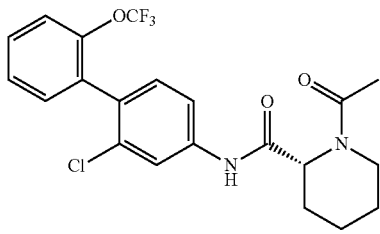

To a dichloromethane (36 mL) solution of the compound of Reference Example 8 (1.43 g, 3.59 mmol), triethylamine (0.750 mL, 5.38 mmol) and acetic anhydride (0.338 mL, 3.59 mmol) were added at 0° C. and the temperature was raised to room temperature, followed by stirring for 30 minutes. To the reaction solution, distilled water was added, and the solution was extracted with chloroform. The organic layer was washed with distilled water and saturated brine, dried over anhydrous sodium sulfate and filtered, and then the filtrate was concentrated under reduced pressure. The residue was purified by column chromatography (silica gel, chloroform/methanol=95/5) to obtain (R)-1-acetyl-N-(2-chloro-2'-(trifluoromethoxy)-[1,1'-biphenyl]-4-yl)piperidine-2-carboxamide (hereinafter referred to as the compound of Example 20) (1.02 g, 2.32 mmol, 64.6%) as a white solid. As a result of analysis using a chiral column, the retention time of the thus obtained compound of Example 20 was 32.8 minutes, and the optical purity at that time was 99.0% ee. The analysis conditions using the chiral column are as follows.
Measurement equipment; High-performance liquid chromatograph LC-2010CHT, manufactured by Shimadzu Corporation
Column; CHIRALCEL OD-RH 0.46 cmφ×15 cm, particle size of 5 m, manufactured by Daicel Chemical Industries Ltd.
Column temperature; 40° C.
Mobile phase; (Solution A) aqueous 20 mM potassium dihydrogen phosphate solution, (Solution B) acetonitrile
Composition of mobile phase; Solution A:Solution B=60:40 to 50:50 (0 to 40 minutes, linear gradient)
Solution A:Solution B=50:50 to 60:40 (40 to 41 minutes, linear gradient)
Solution A:Solution B=60:40 (41 to 50 minutes)
Flow rate; 0.5 mL/minute
Detection; UV (210 nm)
$^1$H-NMR (400 MHz, CDCl$_3$) δ: 1.46-1.63 (m, 1H), 1.67 (d, J=7.8 Hz, 1H), 1.89-2.02 (m, 2H), 2.22 (s, 3H), 2.29 (d, J=12.9 Hz, 1H), 3.22 (t, J=13.2 Hz, 1H), 3.78 (d, J=12.7 Hz, 1H), 5.29 (d, J=5.1 Hz, 1H), 7.20 (d, J=8.3 Hz, 1H), 7.29-7.37 (m, 3H), 7.40-7.44 (m, 2H), 7.80 (br, 1H), 8.65 (br, 1H).
ESI-MS: m/z=441 (M+H)$^+$.

Example 21 Synthesis of (R)—N-(2-chloro-2'-(trifluoromethoxy)-[1,1'-biphenyl]-4-yl)-1-(methylsulfonyl)piperidine-2-carboxamide

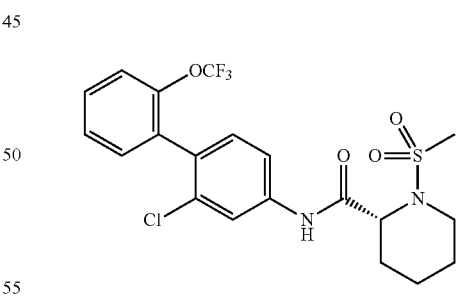

According to the same procedure as in Example 3, except that the compound of Reference Example 8 was used in place of the compound of Reference Example 3 and methanesulfonyl chloride was used in place of propionyl chloride, (R)—N-(2-chloro-2'-(trifluoromethoxy)-[1,1'-biphenyl]-4-yl)-1-(methylsulfonyl)piperidine-2-carboxamide (hereinafter referred to as the compound of Example 21) (0.0600 g, 0.126 mmol, 99.0%) was obtained as a white solid. $^1$H-NMR (400 MHz, CDCl$_3$) δ: 1.47-1.61 (m, 1H), 1.62-1.81 (m, 4H), 2.45 (d, J=10.4 Hz, 1H), 3.04 (s, 3H), 3.23 (td, J=13.3, 2.4 Hz, 1H), 3.93 (t, J=7.0 Hz, 1H), 4.64

(br, 1H), 7.25 (d, J=8.5 Hz, 1H), 7.30-7.38 (m, 3H), 7.43 (dt, J=10.8, 3.7 Hz, 2H), 7.84 (d, J=2.2 Hz, 1H), 8.29 (br, 1H).
ESI-MS: m/z=477 (M+H)$^+$.

Example 22 Synthesis of (R)—N$^2$-(2-chloro-2'-(trifluoromethoxy)-[1,1'-biphenyl]-4-yl)piperidine-1,2-dicarboxamide

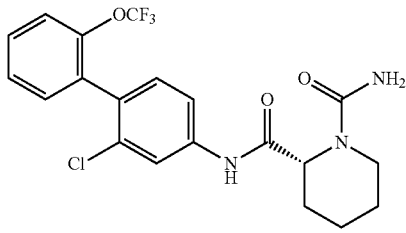 [SMILES: NC(=O)N1CCCC[C@@H]1C(=O)Nc1ccc(-c2ccccc2OC(F)(F)F)c(Cl)c1]

To a dichloromethane (30 mL) solution of the compound of Reference Example 8 (3.00 g, 7.52 mmol), trimethylsilyl isocyanate (2.00 mL, 15.04 mmol) and triethylamine (1.05 mL, 7.57 mmol) were added at 0° C. and the temperature was raised to room temperature, followed by stirring for 18 hours. To the reaction solution, methanol was added, and the solution was concentrated under reduced pressure. The residue was purified by column chromatography (silica gel, chloroform) to obtain (R)—N$^2$-(2-chloro-2'-(trifluoromethoxy)-[1,1'-biphenyl]-4-yl)piperidine-1,2-dicarboxamide (hereinafter referred to as the compound of Example 22) (2.50 g, 5.66 mmol, 75.2%) as a white solid.
$^1$H-NMR (400 MHz, CDCl$_3$) δ: 1.50-1.68 (m, 2H), 1.73 (br, 2H), 1.81-1.92 (m, 1H), 2.30 (d, J=12.9 Hz, 1H), 3.21 (dt, J=12.8, 2.6 Hz, 1H), 3.52 (d, J=13.2 Hz, 1H), 4.81 (br, 2H), 5.03 (d, J=4.6 Hz, 1H), 7.20 (d, J=8.3 Hz, 1H), 7.29-7.37 (m, 3H), 7.42 (dt, J=10.8, 3.8 Hz, 2H), 7.81 (br, 1H), 8.95 (br, 1H).
ESI-MS: m/z=442 (M+H)$^+$.

Example 23 Synthesis of (R)—N-(2-chloro-2'-(trifluoromethoxy)-[1,1'-biphenyl]-4-yl)-1-(2,2,2-trifluoroacetyl)piperidine-2-carboxamide

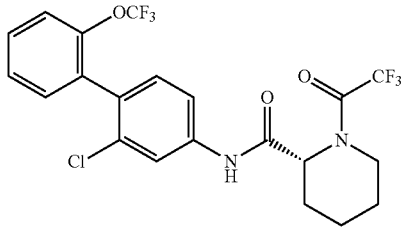

To a dichloromethane (75 mL) solution of the compound of Reference Example 8 (3.00 g, 7.52 mmol), triethylamine (1.57 mL, 11.28 mmol) and trifluoroacetic anhydride (1.17 mL, 8.27 mmol) were added at 0° C. and the temperature was raised to room temperature, followed by stirring for 30 minutes. To the reaction solution, distilled water was added, and the solution was extracted with chloroform. The organic layer was washed with distilled water and saturated brine, dried over anhydrous sodium sulfate and filtered, and then the filtrate was concentrated under reduced pressure. The residue was purified by column chromatography (silica gel, n-hexane/ethyl acetate=20/80) to obtain (R)—N-(2-chloro-2'-(trifluoromethoxy)-[1,1'-biphenyl]-4-yl)-1-(2,2,2-trifluoroacetyl)piperidine-2-carboxamide (hereinafter referred to as the compound of Example 23) (2.50 g, 5.05 mmol, 67.2%) as a white solid. As a result of analysis using a chiral column, the retention time of the thus obtained compound of Example 23 was 33.6 minutes, and the optical purity at that time was 95.0% ee. The analysis conditions using the chiral column are as follows.
Measurement equipment; High-performance liquid chromatograph LC-2010CHT, manufactured by Shimadzu Corporation
Column; CHIRALCEL OD-RH 0.46 cmφ×15 cm, particle size of 5 μm, manufactured by Daicel Chemical Industries Ltd.
Column temperature; 40° C.
Mobile phase; (Solution A) 20 mM aqueous potassium dihydrogen phosphate solution, (Solution B) acetonitrile
Composition of mobile phase; Solution A:Solution B=60:40 to 50:50 (0 to 40 minutes, linear gradient)
Solution A:Solution B=50:50 to 60:40 (40 to 41 minutes, linear gradient)
Solution A:Solution B=60:40 (41 to 50 minutes)
Flow rate; 0.5 mL/minute
Detection; UV (210 nm)
$^1$H-NMR (400 MHz, CDCl$_3$) δ: 1.56-1.86 (m, 4H), 1.98 (dt, J=11.2, 4.6 Hz, 1H), 2.36 (d, J=14.1 Hz, 1H), 3.37 (td, J=13.4, 2.6 Hz, 1H), 4.01 (d, J=13.9 Hz, 1H), 5.18 (d, J=5.4 Hz, 1H), 7.21 (d, J=8.3 Hz, 1H), 7.30-7.46 (m, 5H), 7.79 (br, 1H), 7.89 (br, 1H).
ESI-MS: m/z=495 (M+H)$^+$.

Reference Example 9 Synthesis of (1R,5S)-2-((R)-1-phenylethyl)-6-oxa-2-azabicyclo[3.2.1]octan-7-one

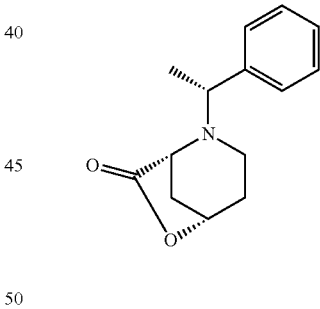

To a DMF (30 mL) solution of (R)-α-methylbenzylamine (3.77 mL, 29.6 mmol), potassium carbonate (4.09 g, 29.6 mmol) and 4-bromo-1-butene (3.01 mL, 29.6 mmol) were added at room temperature, followed by stirring at the same temperature for 24 hours. To the reaction solution, distilled water was added, and the solution was extracted with diethyl ether. The organic layer was washed with saturated brine, dried over anhydrous sodium sulfate and filtered, and then the filtrate was concentrated under reduced pressure. To a tetrahydrofuran (12 mL) solution of the residue, glyoxylic acid (4.09 mL, 36.8 mmol) was added at 0° C. and the temperature was raised to 60° C., followed by stirring for 9 hours. To the reaction solution, distilled water and an aqueous 1M sodium hydroxide solution was added, and the solution was extracted with ethyl acetate. The organic layer was washed with an aqueous saturated sodium hydrogen carbonate solution, distilled water, and saturated brine, dried over anhydrous sodium sulfate and filtered, and then the filtrate was concentrated under reduced pressure. The residue was purified by column chromatography (silica gel, n-hexane/ethyl acetate=91/9 to 85/15) to obtain (1R,5S)-2-((R)-1-phenylethyl)-6-oxa-2-azabicyclo[3.2.1]octan-7-one (hereinafter referred to as the compound of Reference Example 9) (1.73 g, 7.48 mmol, 25.3%) as a pale yellow oily product.

$^1$H-NMR (400 MHz, CDCl$_3$) δ: 1.33 (d, J=6.6 Hz, 3H), 1.82 (d, J=11.7 Hz, 1H), 1.87-1.95 (m, 1H), 2.03-2.12 (m, 2H), 2.47 (td, J=11.8, 5.1 Hz, 1H), 3.19 (d, J=5.1 Hz, 1H), 3.35 (dd, J=12.0, 6.6 Hz, 1H), 3.70 (q, J=6.6 Hz, 1H), 4.78 (t, J=5.1 Hz, 1H), 7.23-7.27 (m, 1H), 7.31-7.35 (m, 2H), 7.39-7.41 (m, 2H).

ESI-MS: m/z=232 (M+H)$^+$.

Reference Example 10 Synthesis of (1R,5S)-2-(tert-butoxycarbonyl)-6-oxa-2-azabicyclo[3.2.1]-octan-7-one

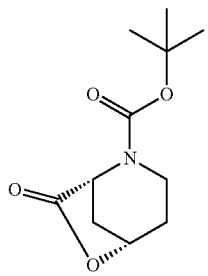 [SMILES: CC(C)(C)OC(=O)N1CC[C@H]2C[C@@H]1C(=O)O2]

To an ethyl acetate (25 mL) solution of the compound of Reference Example 9 (1.73 g, 7.48 mmol), 20% by weight palladium hydroxide-carbon (containing 50% by weight of water, 0.210 g) and di-tert-butyl dicarbonate (1.80 g, 8.23 mmol) were added at room temperature, followed by stirring in a hydrogen atmosphere at the same temperature for 36 hours. The reaction solution was filtered through Celite and then the filtrate was concentrated under reduced pressure. The residue was suspended in diethyl ether/n-hexane=1/9 (v/v) and the obtained solid was collected by filtration and dried to obtain (1R,5S)-2-(tert-butoxycarbonyl)-6-oxa-2-azabicyclo[3.2.1]-octan-7-one (hereinafter referred to as the compound of Reference Example 10) (1.63 g, 7.17 mmol, 95.9%) as a white solid.

$^1$H-NMR (400 MHz, CDCl$_3$) δ: 1.48 (s, 9H), 1.84-1.93 (m, 1H), 1.95 (d, J=12.0 Hz, 1H), 2.03-2.06 (m, 1H), 2.29-2.32 (m, 1H), 3.18-3.21 (m, 1H), 4.06 (m, 1H), 4.70-4.85 (m, 1H), 4.97 (t, J=5.1 Hz, 1H).

ESI-MS: m/z=228 (M+H)$^+$.

Reference Example 11 Synthesis of tert-butyl (2R,4S)-2-((2-chloro-2'-(trifluoromethoxy)-[1,1'-biphenyl]-4-yl)carbamoyl)-4-hydroxypiperidine-1-carboxylate

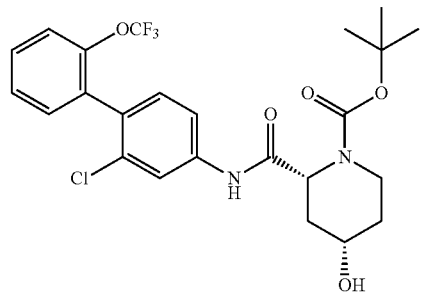 [SMILES: CC(C)(C)OC(=O)N1CC[C@H](O)C[C@@H]1C(=O)Nc1ccc(-c2ccccc2OC(F)(F)F)c(Cl)c1]

To a toluene (2.3 mL) solution of the compound of Reference Example 10 (0.320 g, 1.41 mmol), a trimethylaluminum-toluene solution (1.4M, 1.31 mL, 1.83 mmol) was added at 0° C. and the temperature was raised to room temperature, followed by stirring for 30 minutes. A toluene (2.3 mL) solution of the compound of Reference Example 1 (0.486 g, 1.690 mmol) was added and the temperature was raised to 50° C., followed by stirring for 4 hours. To the reaction solution, 1M hydrochloric acid was added, and the solution was extracted with ethyl acetate. The organic layer was washed with distilled water and saturated brine, dried over anhydrous sodium sulfate and filtered, and then the filtrate was concentrated under reduced pressure. The residue was purified by column chromatography (silica gel, n-hexane/ethyl acetate=80/20 to 50/50) to obtain tert-butyl (2R,4S)-2-((2-chloro-2'-(trifluoromethoxy)-[1,1'-biphenyl]-4-yl)carbamoyl)-4-hydroxypiperidine-1-carboxylate (hereinafter referred to as the compound of Reference Example 11) (0.654 g, 1.27 mmol, 90.2%) as a white solid.

$^1$H-NMR (400 MHz, CDCl$_3$) δ: 1.54 (s, 9H), 1.66-1.69 (m, 1H), 1.78-1.82 (m, 1H), 1.93-2.00 (m, 1H), 2.40 (d, J=13.4 Hz, 1H), 3.25 (td, J=13.2, 2.4 Hz, 1H), 3.86-3.88 (m, 1H), 4.12-4.14 (m, 1H), 4.98-5.00 (m, 1H), 5.20 (br, 1H), 7.24 (d, J=8.3 Hz, 1H), 7.30-7.46 (m, 5H), 7.75-7.78 (m, 1H), 9.08 (br, 1H).

ESI-MS: m/z=515 (M+H)$^+$.

Reference Example 12 Synthesis of (2R,4S)—N-(2-chloro-2'-(trifluoromethoxy)-[1,1'-biphenyl]-4-yl)-4-hydroxypiperidine-2-carboxamide hydrochloride

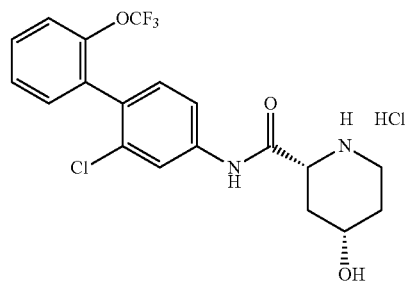

To an ethyl acetate (0.5 mL) solution of the compound of Reference Example 11 (0.0500 g, 0.0973 mmol), a hydrogen chloride-ethyl acetate solution (4.0M, 0.486 mL, 1.94 mmol) was added at 0° C. and the temperature was raised to room temperature, followed by stirring for 3 hours. The reaction solution was filtered and the obtained solid collected by filtration was washed with ethyl acetate and then dried to obtain (2R,4S)—N-(2-chloro-2'-(trifluoromethoxy)-[1,1'-biphenyl]-4-yl)-4-hydroxypiperidine-2-carboxamide hydrochloride (hereinafter referred to as the compound of Reference Example 12) (0.0409 g, 0.0908 mmol, 93.3%) as a white solid.

$^{1}$H-NMR (DMSO-D$_{6}$) δ: 1.46-1.62 (m, 2H), 1.91-1.94 (m, 1H), 2.42-2.45 (m, 1H), 3.01 (t, J=12.2 Hz, 1H), 3.28-3.32 (m, 1H), 3.69-3.78 (m, 1H), 4.00 (d, J=12.0 Hz, 1H), 5.28 (d, J=4.9 Hz, 1H), 7.38 (d, J=8.3 Hz, 1H), 7.42 (dd, J=7.8, 1.7 Hz, 1H), 7.48-7.52 (m, 2H), 7.56-7.64 (m, 2H), 7.94 (s, 1H), 8.93 (br, 1H), 11.00 (s, 1H).

ESI-MS: m/z=415 (M+H)$^{+}$.

Reference Example 13 Synthesis of tert-butyl (2R,4R)-2-((2-chloro-2'-(trifluoromethoxy)-[1,1'-biphenyl]-4-yl)carbamoyl)-4-fluoropiperidine-1-carboxylate

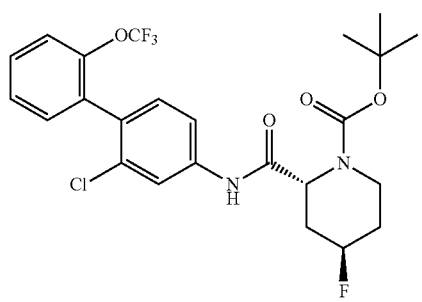 [SMILES: CC(C)(C)OC(=O)N1CC[C@@H](F)C[C@@H]1C(=O)Nc1ccc(-c2ccccc2OC(F)(F)F)c(Cl)c1]

To a dichloromethane (1.9 mL) solution of the compound of Reference Example 11 (0.100 g, 0.194 mmol), (diethylamino)sulfur trifluoride (0.0380 mL, 0.291 mmol) was added at −78° C. and the temperature was raised to room temperature, followed by stirring for 24 hours. To the reaction solution, an aqueous saturated sodium hydrogen carbonate solution was added, and the solution was extracted with chloroform. The organic layer was washed with saturated brine, dried over anhydrous sodium sulfate and filtered, and then the filtrate was concentrated under reduced pressure. The residue was purified by column chromatography (silica gel, n-hexane/ethyl acetate=90/10 to 80/20) to obtain tert-butyl (2R,4R)-2-((2-chloro-2'-(trifluoromethoxy)-[1,1'-biphenyl]-4-yl)carbamoyl)-4-fluoropiperidine-1-carboxylate (hereinafter referred to as the compound of Reference Example 13) (0.0272 g, 0.0527 mmol, 27.2%) as a white solid.

$^{1}$H-NMR (400 MHz, CDCl$_{3}$) δ: 1.48-1.56 (m, 1H), 1.54 (s, 9H), 1.59-1.86 (m, 2H), 2.07-2.19 (m, 1H), 2.65-2.71 (m, 1H), 2.93 (t, J=12.8 Hz, 1H), 4.10-4.13 (m, 1H), 5.04-5.06 (m, 1H), 7.22 (d, J=8.3 Hz, 1H), 7.29-7.36 (m, 4H), 7.41-7.45 (m, 1H), 7.76 (br, 1H).

ESI-MS: m/z=517 (M+H)+.

Reference Example 14 Synthesis of (2R,4R)—N-(2-chloro-2'-(trifluoromethoxy)-[1,1'-biphenyl]-4-yl)-4-fluoropiperidine-2-carboxamide hydrochloride

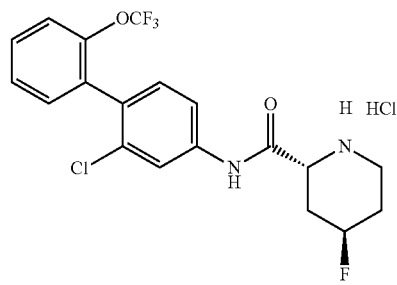

According to the same procedure as in Example 12, except that the compound of Reference Example 13 was used in place of the compound of Reference Example 11, (2R,4R)—N-(2-chloro-2'-(trifluoromethoxy)-[1,1'-biphenyl]-4-yl)-4-fluoropiperidine-2-carboxamide hydrochloride (hereinafter referred to as the compound of Reference Example 14) (0.0186 g, 0.0410 mmol, 84.9%) was obtained as a white solid.

$^{1}$H-NMR (DMSO-D$_{6}$) δ: 1.89-2.06 (m, 2H), 2.24-2.33 (m, 1H), 3.12-3.27 (m, 2H), 4.18 (d, J=12.4 Hz, 1H), 5.16 (d, J=47.1 Hz, 1H), 7.38 (d, J=8.5 Hz, 1H), 7.42 (dd, J=7.9, 1.8 Hz, 1H), 7.48-7.52 (m, 2H), 7.56-7.61 (m, 2H), 7.95 (br, 1H), 9.12 (br, 1H), 10.97 (s, 1H).

ESI-MS: m/z=417 (M+H)$^{+}$.

Reference Example 15 Synthesis of tert-butyl (2R,4R)-2-((2-chloro-2'-(trifluoromethoxy)-[1,1'-biphenyl]-4-yl)carbamoyl)-4-(formyloxy)piperidine-1-carboxylate

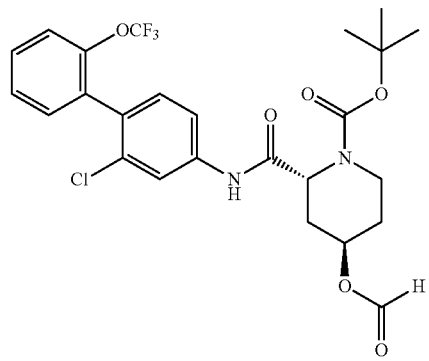 [SMILES: CC(C)(C)OC(=O)N1CC[C@@H](OC=O)C[C@@H]1C(=O)Nc1ccc(-c2ccccc2OC(F)(F)F)c(Cl)c1]

To a tetrahydrofuran (1.0 mL) solution of triphenylphosphine (0.153 g, 0.583 mmol), diisopropyl azodicarboxylate (0.113 mL, 0.583 mmol) was added at 0° C. and, after stirring at the same temperature for 1 hour, formic acid (0.0220 mL, 0.583 mmol) was added and the mixture was stirred at the same temperature for 30 minutes. A tetrahydrofuran (1.00 mL) solution of the compound of Reference Example 11 (0.200 g, 0.388 mmol) was added dropwise and the temperature was raised to room temperature, followed by stirring for 12 hours. The reaction solution was concentrated under reduced pressure and the residue was purified by column chromatography (silica gel, n-hexane/ethyl acetate=85/15 to 70/30) to obtain tert-butyl (2R,4R)-2-((2-chloro-2'-(trifluoromethoxy)-[1,1'-biphenyl]-4-yl)carbamoyl)-4-(formyloxy)piperidine-1-carboxylate (hereinafter referred to as the compound of Reference Example 15) (0.0939 g, 0.173 mmol, 44.5%) as a white solid.

$^1$H-NMR (400 MHz, CDCl$_3$) δ: 1.28-1.37 (m, 2H), 1.54 (s, 9H), 1.67-1.74 (m, 1H), 2.07-2.12 (m, 1H), 2.61-2.63 (m, 1H), 2.96-3.02 (m, 1H), 4.12-4.14 (m, 1H), 5.06 (br, 1H), 5.43 (br, 1H), 7.22 (d, J=8.3 Hz, 1H), 7.32-7.37 (m, 3H), 7.41-7.45 (m, 2H), 7.80 (br, 1H), 8.06 (s, 1H).

ESI-MS: m/z=543 (M+H)$^+$.

Reference Example 16 Synthesis of tert-butyl (2R, 4R)-2-((2-chloro-2'-(trifluoromethoxy)-[1,1'-biphenyl]-4-yl)carbamoyl)-4-hydroxypiperidine-1-carboxylate

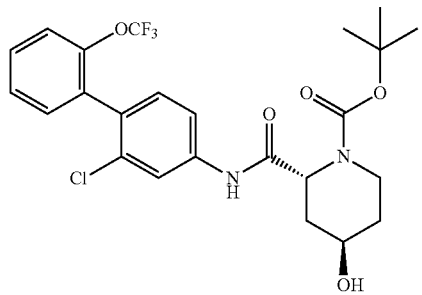 [SMILES: CC(C)(C)OC(=O)N1CC[C@@H](O)C[C@@H]1C(=O)Nc1ccc(-c2ccccc2OC(F)(F)F)c(Cl)c1]

To a methanol (1.1 mL) solution of the compound of Reference Example 15 (0.0900 g, 0.166 mmol), a sodium methoxide-methanol solution (4.0M, 0.0207 mL, 0.0828 mmol) was added at 0° C., followed by stirring at the same temperature for 15 minutes. To the reaction solution, 1M hydrochloric acid was added, and the solution was extracted with ethyl acetate. The organic layer was washed with saturated brine, dried over anhydrous sodium sulfate and filtered, and then the filtrate was concentrated under reduced pressure. The residue was purified by column chromatography (silica gel, n-hexane/ethyl acetate=80/20 to 50/50) to obtain tert-butyl (2R,4R)-2-((2-chloro-2'-(trifluoromethoxy)-[1,1'-biphenyl]-4-yl)carbamoyl)-4-hydroxypiperidine-1-carboxylate (hereinafter referred to as the compound of Reference Example 16) (0.0844 g, 0.164 mmol, 99.3%) as a white solid.

$^1$H-NMR (400 MHz, CDCl$_3$) δ: 1.46-1.54 (m, 2H), 1.54 (s, 9H), 1.68-1.71 (m, 1H), 1.94-1.97 (m, 1H), 2.54-2.56 (m, 1H), 2.86-2.93 (m, 1H), 4.13-4.22 (m, 2H), 5.04 (br, 1H), 7.22 (d, J=8.3 Hz, 1H), 7.30-7.45 (m, 5H), 7.78 (br, 1H), 8.52 (s, 1H).

ESI-MS: m/z=515 (M+H)$^+$.

Reference Example 17 Synthesis of tert-butyl (R)-2-((2-chloro-2'-(trifluoromethoxy)-[1,1'-biphenyl]-4-yl)carbamoyl)-4-oxopiperidine-1-carboxylate

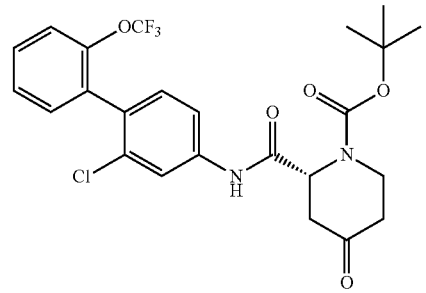 [SMILES: CC(C)(C)OC(=O)N1CCC(=O)C[C@@H]1C(=O)Nc1ccc(-c2ccccc2OC(F)(F)F)c(Cl)c1]

To a dichloromethane (2.0 mL) solution of the compound of Reference Example 11 (0.210 g, 0.408 mmol), Dess-Martin periodinane (0.190 g, 0.449 mmol) was added at 0° C. and the temperature was raised to room temperature, followed by stirring for 3 hours. To the reaction solution, an aqueous sodium thiosulfate solution was added, and the solution was extracted with ethyl acetate. The organic layer was washed with distilled water and saturated brine, dried over anhydrous sodium sulfate and filtered, and then the filtrate was concentrated under reduced pressure. The residue was purified by column chromatography (silica gel, n-hexane/ethyl acetate=90/10 to 60/40) to obtain tert-butyl (R)-2-((2-chloro-2'-(trifluoromethoxy)-[1,1'-biphenyl]-4-yl) carbamoyl)-4-oxopiperidine-1-carboxylate (hereinafter referred to as the compound of Reference Example 17) (0.190 g, 0.370 mmol, 90.9%) as a white solid.

$^1$H-NMR (400 MHz, CDCl$_3$) δ: 1.56 (s, 9H), 2.46-2.53 (m, 1H), 2.61-2.73 (m, 2H), 3.00 (dd, J=16.5, 3.3 Hz, 1H), 3.66-3.73 (m, 1H), 3.82 (br, 1H), 5.05 (s, 1H), 7.22 (d, J=8.3 Hz, 1H), 7.29-7.36 (m, 3H), 7.41-7.45 (m, 2H), 7.78 (br, 1H), 9.14 (br, 1H).

ESI-MS: m/z=513 (M+H)$^+$.

Reference Example 18 Synthesis of tert-butyl (R)-2-((2-chloro-2'-(trifluoromethoxy)-[1,1'-biphenyl]-4-yl)carbamoyl)-4,4-difluoropiperidine-1-carboxylate

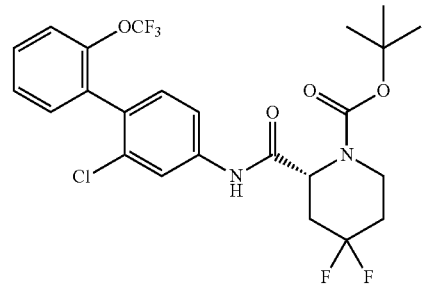 [SMILES: CC(C)(C)OC(=O)N1CCC(F)(F)C[C@@H]1C(=O)Nc1ccc(-c2ccccc2OC(F)(F)F)c(Cl)c1]

To a dichloromethane (1.9 mL) solution of the compound of Reference Example 17 (0.190 g, 0.370 mmol), (diethylamino)sulfur trifluoride (0.108 mL, 0.815 mmol) was added at 0° C. and the temperature was raised to room temperature, followed by stirring for 24 hours. To the reaction solution, an aqueous saturated sodium hydrogen carbonate solution was added, and the solution was extracted with chloroform.

The organic layer was washed with saturated brine, dried over anhydrous sodium sulfate and filtered, and then the filtrate was concentrated under reduced pressure. The residue was purified by column chromatography (silica gel, n-hexane/ethyl acetate=85/15 to 70/30) to obtain tert-butyl (R)-2-((2-chloro-2'-(trifluoromethoxy)-[1,1'-biphenyl]-4-yl)carbamoyl)-4,4-difluoropiperidine-1-carboxylate (hereinafter referred to as the compound of Reference Example 18) (0.0393 g, 0.0735 mmol, 19.8%) as a white solid.

$^1$H-NMR (400 MHz, CDCl$_3$) δ: 1.54 (s, 9H), 1.86-2.15 (m, 3H), 2.99-3.07 (m, 1H), 3.21 (td, J=13.3, 2.7 Hz, 1H), 4.22-4.25 (m, 1H), 5.07 (br, 1H), 7.24 (d, J=8.5 Hz, 1H), 7.30-7.37 (m, 3H), 7.41-7.46 (m, 2H), 7.76 (s, 1H), 7.97 (br, 1H).

ESI-MS: m/z=535 (M+H)$^+$.

Example 24 Synthesis of (2R,4S)-1-acetyl-N-(2-chloro-2'-(trifluoromethoxy)-[1,1'-biphenyl]-4-yl)-4-hydroxypiperidine-2-carboxamide

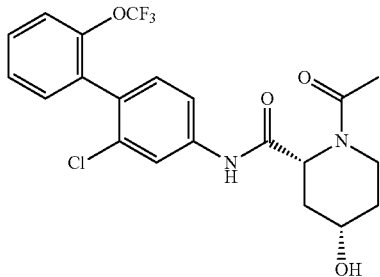 [SMILES: CC(=O)N1CC[C@H](O)C[C@@H]1C(=O)Nc1ccc(-c2ccccc2OC(F)(F)F)c(Cl)c1]

According to the same procedure as in Example 3, except that the compound of Reference Example 12 was used in place of the compound of Reference Example 3 and acetyl chloride was used in place of propionyl chloride, (2R,4S)-1-acetyl-N-(2-chloro-2'-(trifluoromethoxy)-[1,1'-biphenyl]-4-yl)-4-hydroxypiperidine-2-carboxamide (hereinafter referred to as the compound of Example 24) (0.0166 g, 0.0363 mmol, 91.1%) was obtained as a white solid.

$^1$H-NMR (400 MHz, CDCl$_3$) δ: 1.68-1.76 (m, 1H), 1.87-1.98 (m, 2H), 2.24 (s, 3H), 2.39 (d, J=14.6 Hz, 1H), 3.50-3.57 (m, 1H), 3.61-3.66 (m, 1H), 4.14-4.17 (m, 1H), 5.42 (d, J=6.8 Hz, 1H), 5.52 (d, J=6.8 Hz, 1H), 7.23 (d, J=8.5 Hz, 1H), 7.31-7.37 (m, 3H), 7.41-7.46 (m, 2H), 7.77 (br, 1H), 9.15 (s, 1H).

ESI-MS: m/z=457 (M+H)$^+$.

Example 25 Synthesis of (2R,4R)-1-acetyl-N-(2-chloro-2'-(trifluoromethoxy)-[1,1'-biphenyl]-4-yl)-4-fluoropiperidine-2-carboxamide

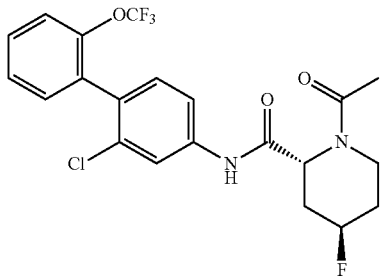 [SMILES: CC(=O)N1CC[C@@H](F)C[C@@H]1C(=O)Nc1ccc(-c2ccccc2OC(F)(F)F)c(Cl)c1]

According to the same procedure as in Example 3, except that the compound of Reference Example 14 was used in place of the compound of Reference Example 3 and acetyl chloride was used in place of propionyl chloride, (2R,4R)-1-acetyl-N-(2-chloro-2'-(trifluoromethoxy)-[1,1'-biphenyl]-4-yl)-4-fluoropiperidine-2-carboxamide (hereinafter referred to as the compound of Example 25) (0.0108 g, 0.0235 mmol, 62.8%) was obtained as a white solid.

$^1$H-NMR (400 MHz, CDCl$_3$) δ: 1.69-1.85 (m, 2H), 2.22-2.25 (m, 1H), 2.25 (s, 3H), 2.62-2.69 (m, 1H), 3.21-3.28 (m, 1H), 3.85 (dd, J=13.4, 2.9 Hz, 1H), 5.24-5.43 (m, 1H), 5.43 (d, J=5.4 Hz, 1H), 7.21 (d, J=8.3 Hz, 1H), 7.30-7.36 (m, 3H), 7.41-7.45 (m, 2H), 7.70-7.82 (m, 1H), 8.72 (s, 1H).

ESI-MS: m/z=459 (M+H)$^+$.

Example 26 Synthesis of (2R,4S)—N-(2-chloro-2'-(trifluoromethoxy)-[1,1'-biphenyl]-4-yl)-4-hydroxy-1-(methylsulfonyl)piperidine-2-carboxamide

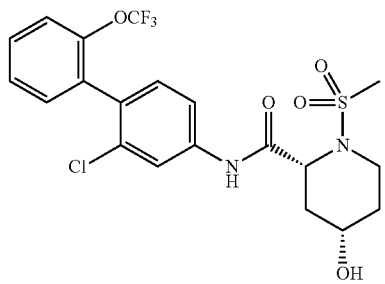 [SMILES: CS(=O)(=O)N1CC[C@H](O)C[C@@H]1C(=O)Nc1ccc(-c2ccccc2OC(F)(F)F)c(Cl)c1]

According to the same procedure as in Example 3, except that the compound of Reference Example 12 was used in place of the compound of Reference Example 3 and methanesulfonyl chloride was used in place of propionyl chloride, (2R,4S)—N-(2-chloro-2'-(trifluoromethoxy)-[1,1-biphenyl]-4-yl)-4-hydroxy-1-(methylsulfonyl)piperidine-2-carboxamide (hereinafter referred to as the compound of Example 26) (0.00841 g, 0.0171 mmol, 42.7%) was obtained as a white solid.

$^1$H-NMR (400 MHz, CDCl$_3$) δ: 1.68-1.76 (m, 1H), 1.85-1.88 (m, 1H), 1.99 (ddd, J=14.9, 6.9, 3.1 Hz, 1H), 2.61 (d, J=14.9 Hz, 1H), 3.03 (s, 3H), 3.55-3.62 (m, 1H), 3.72 (d, J=4.6 Hz, 1H), 3.75-3.79 (m, 1H), 4.22-4.24 (m, 1H), 4.66 (d, J=6.6 Hz, 1H), 7.25-7.27 (m, 1H), 7.31-7.37 (m, 3H), 7.42-7.46 (m, 2H), 7.81 (d, J=2.0 Hz, 1H), 8.58 (s, 1H).

ESI-MS: m/z=493 (M+H)$^+$.

Example 27 Synthesis of (2R,4R)-1-acetyl-N-(2-chloro-2'-(trifluoromethoxy)-[1,1'-biphenyl]-4-yl)-4-hydroxypiperidine-2-carboxamide

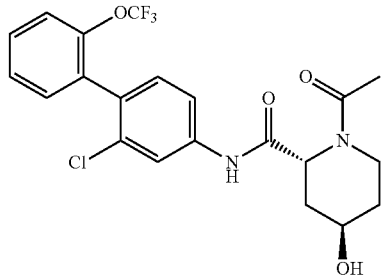 [SMILES: CC(=O)N1CC[C@@H](O)C[C@@H]1C(=O)Nc1ccc(-c2ccccc2OC(F)(F)F)c(Cl)c1]

To an ethyl acetate (0.4 mL) solution of the compound of Reference Example 16 (0.0200 g, 0.0388 mmol), a hydrogen chloride-ethyl acetate solution (4.0M, 0.194 mL, 1.94 mmol) was added at 0° C. and the temperature was raised to room temperature, followed by stirring for 3 hours. The reaction solution was concentrated under reduced pressure and the residue was dissolved in dichloromethane (0.8 mL) and then triethylamine (0.00135 mL, 0.0970 mmol) and acetyl chloride (0.00359 mL, 0.0504 mmol) were added at 0° C., followed by stirring at the same temperature for 1 hour. To the reaction solution, methanol was added, and the solution was concentrated under reduced pressure. The residue was purified by column chromatography (silica gel, ethyl acetate/methanol=100/0 to 97/3) to obtain (2R,4R)-1-acetyl-N-(2-chloro-2'-(trifluoromethoxy)-[1,1'-biphenyl]-4-yl)-4-hydroxypiperidine-2-carboxamide (hereinafter referred to as the compound of Example 27) (0.0106 g, 0.0232 mmol, 59.7%) as a white solid.

$^1$H-NMR (400 MHz, CDCl$_3$) δ: 1.47-1.57 (m, 2H), 1.81 (d, J=3.6 Hz, 1H), 2.04-2.09 (m, 1H), 2.25 (s, 3H), 2.50 (ddt, J=13.1, 5.0, 1.8 Hz, 1H), 3.22 (td, J=13.4, 2.6 Hz, 1H), 3.85 (d, J=13.4 Hz, 1H), 4.40-4.48 (m, 1H), 5.43 (d, J=5.9 Hz, 1H), 7.21 (d, J=8.2 Hz, 1H), 7.30-7.37 (m, 3H), 7.41-7.45 (m, 2H), 7.69-7.83 (m, 1H), 8.65 (s, 1H).

ESI-MS: m/z=457 (M+H)$^+$.

Example 28 Synthesis of (R)—N-(2-chloro-2'-(trifluoromethoxy)-[1,1'-biphenyl]-4-yl)-4,4-difluoro-1-(methylsulfonyl)piperidine-2-carboxamide

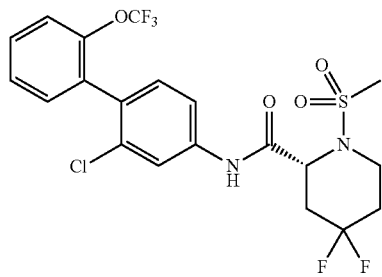 [SMILES: CS(=O)(=O)N1CCC(F)(F)C[C@@H]1C(=O)Nc1ccc(-c2ccccc2OC(F)(F)F)c(Cl)c1]

According to the same procedure as in Example 27, except that the compound of Reference Example 18 was used in place of the compound of Reference Example 16 and methanesulfonyl chloride was used in place of acetyl chloride, (R)—N-(2-chloro-2'-(trifluoromethoxy)-[1,1'-biphenyl]-4-yl)-4,4-difluoro-1-(methylsulfonyl)piperidine-2-carboxamide (hereinafter referred to as the compound of Example 28) (0.0127 g, 0.0248 mmol, 77.0%) was obtained as a white solid.

$^1$H-NMR (400 MHz, CDCl$_3$): 1.95-2.12 (m, 1H), 2.15-2.32 (m, 2H), 2.95-3.02 (m, 1H), 3.10 (s, 3H), 3.60 (td, J=13.5, 3.0 Hz, 1H), 4.02-4.08 (m, 1H), 4.89 (d, J=7.2 Hz, 1H), 7.26 (d, J=8.2 Hz, 1H), 7.30-7.37 (m, 3H), 7.42-7.46 (m, 2H), 7.76 (s, 1H), 7.93 (s, 1H).

ESI-MS: m/z=513 (M+H)$^+$.

Reference Example 19 Synthesis of tert-butyl 2-(N-methylmethylsulfonamide)acetate

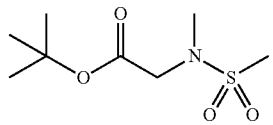

To a dichloromethane (2.0 mL) solution of tert-butyl 2-(methylamino)acetate hydrochloride (0.100 g, 0.550 mmol), triethylamine (0.192 mL, 1.385 mmol) and methanesulfonyl chloride (0.0515 mL, 0.661 mmol) were added at 0° C. and the temperature was raised to room temperature, followed by stirring for 3 hours. To the reaction solution, an aqueous saturated ammonium chloride solution was added, and the solution was extracted with chloroform. The organic layer was dried over anhydrous sodium sulfate and filtered, and then the filtrate was concentrated under reduced pressure. The residue was purified by column chromatography (silica gel, n-hexane/ethyl acetate=90/10 to 70/30) to obtain tert-butyl 2-(N-methylmethylsulfonamide)acetate (hereinafter referred to as the compound of Reference Example 19) (0.117 g, 0.524 mmol, 95.2%) as a colorless oily product.

$^1$H-NMR (400 MHz, CDCl$_3$) δ: 1.48 (s, 9H), 2.98 (s, 3H), 3.00 (s, 3H), 3.98 (s, 2H).

Reference Example 20 Synthesis of 2-(N-methylmethylsulfonamide)acetic Acid

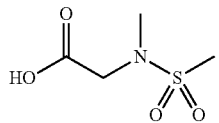

To an acetonitrile (1.5 mL) solution of the compound of Reference Example 19 (0.117 g, 0.524 mmol), a hydrogen chloride-ethyl acetate solution (4.0M, 1.31 mL, 5.24 mmol) was added at 0° C. and the temperature was raised to room temperature, followed by stirring for 16 hours. The reaction solution was concentrated under reduced pressure to obtain crude 2-(N-methylmethylsulfonamide)acetic acid (hereinafter referred to as the compound of Reference Example 20) (0.0855 g) as a colorless oily product. The compound of Reference Example 20 was directly used for the subsequent reaction.

$^1$H-NMR (400 MHz, CDCl$_3$) δ: 2.99 (s, 3H), 3.01 (s, 3H), 4.14 (s, 2H).

ESI-MS: m/z=168 (M+H)$^+$.

Example 29 Synthesis of (R)—N-(2-chloro-2'-(trifluoromethoxy)-[1,1'-biphenyl]-4-yl)-1-(2-(N-methyl-methylsulfonamide)acetyl)piperidine-2-carboxamide

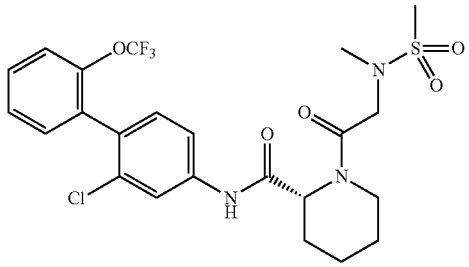

To a DMF (2.0 mL) solution of the compound of Reference Example 20 (0.0850 g, 0.508 mmol), a DMF (1.0 mL) solution of the compound of Reference Example 8 (0.184 g, 0.462 mmol), HATU (0.193 g, 0.508 mmol), and diisopropylethylamine (0.121 mL, 0.693 mmol) were added at room temperature, followed by stirring at the same temperature for 18 hours. To the reaction solution, distilled water was added, and the solution was extracted with a mixed solvent of n-hexane/ethyl acetate=20/80(v/v). The organic layer was washed with saturated brine, dried over anhydrous sodium sulfate and filtered, and then the filtrate was concentrated under reduced pressure. The residue was purified by column chromatography (silica gel, n-hexane/ethyl acetate=50/50 to 30/70) to obtain (R)—N-(2-chloro-2'-(trifluoromethoxy)-[1,1'-biphenyl]-4-yl)-1-(2-(N-methylmethylsulfonamide)acetyl)piperidine-2-carboxamide (hereinafter referred to as the compound of Example 29) (0.209 g, 0.380 mmol, 82.0%) as a white solid. As a result of analysis using a chiral column, the retention time of the thus obtained compound of Example 29 was 34.5 minutes, and the optical purity at that time was 98.2% ee. The analysis conditions using the chiral column are as follows.

Measurement equipment; High-performance liquid chromatograph LC-2010CHT, manufactured by Shimadzu Corporation
Column; CHIRALCEL OD-RH 0.46 cmφ×15 cm, particle size of 5 m, manufactured by Daicel Chemical Industries Ltd.
Column temperature; 40° C.
Mobile phase; (Solution A) 20 mM aqueous potassium dihydrogen phosphate solution, (Solution B) acetonitrile
Composition of mobile phase; Solution A:Solution B=60:40 to 50:50 (0 to 40 minutes, linear gradient)
Solution A:Solution B=50:50 to 60:40 (40 to 41 minutes, linear gradient)
Solution A:Solution B=60:40 (41 to 50 minutes)
Flow rate; 0.5 mL/minute
Detection; UV (210 nm)

$^1$H-NMR (400 MHz, CDCl$_3$) δ: 1.52-1.89 (m, 5H), 2.35-2.38 (m, 1H), 3.03-3.07 (m, 6H), 3.20-3.31 (m, 1H), 3.67-3.76 (m, 1H), 4.16-4.27 (m, 2H), 5.25-5.26 (m, 1H), 7.21-7.23 (m, 1H), 7.30-7.45 (m, 5H), 7.83 (s, 1H), 8.22 (br, 1H).

ESI-MS: m/z=548 (M+H)$^+$.

Reference Example 21 Synthesis of tert-butyl (3-(2-((2-chloro-2'-(trifluoromethoxy)-[1,1'-biphenyl]-4-yl)carbamoyl)piperidin-1-yl)-3-oxopropyl)carbamate

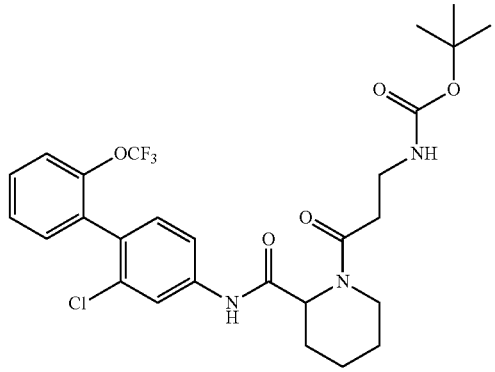

According to the same procedure as in Example 4, except that 3-((tert-butoxycarbonyl)amino)propanoic acid was used in place of 2-methoxyacetic acid, tert-butyl (3-(2-((2-chloro-2'-(trifluoromethoxy)-[1,1'-biphenyl]-4-yl)carbamoyl)piperidin-1-yl)-3-oxopropyl)carbamate (hereinafter referred to as the compound of Reference Example 21) (0.288 g, 0.505 mmol, quantitative) was obtained as a white solid.

$^1$H-NMR (400 MHz, CDCl$_3$) δ: 1.39 (s, 9H), 1.50-1.90 (5H, m), 2.35 (d, J=13.7 Hz, 1H), 2.55-2.75 (m, 2H), 3.20 (t, J=12.8 Hz, 1H), 3.41-3.49 (m, 1H), 3.50-3.60 (m, 1H), 3.80 (d, J=13.7 Hz, 1H) 5.17 (br, 1H), 5.33 (d, J=4.9 Hz, 1H), 7.20 (d, J=8.3 Hz, 1H), 7.29-7.60 (m, 5H), 7.70-7.89 (m, 1H), 8.65 (br, 1H).

ESI-MS: m/z=570 (M+H)$^+$.

Example 30 Synthesis of 1-(3-aminopropanoyl)-N-(2-chloro-2'-(trifluoromethoxy)-[1,1'-biphenyl]-4-yl)piperidine-2-carboxamide

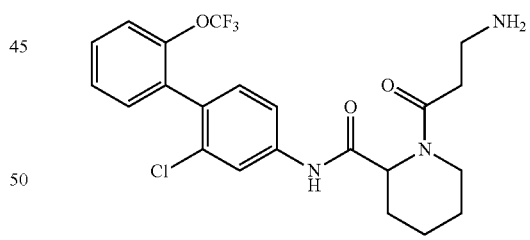

According to the same procedure as in Reference Example 5, except that the compound of Reference Example 21 was used in place of the compound of Reference Example 4, 1-(3-aminopropanoyl)-N-(2-chloro-2'-(trifluoromethoxy)-[1,1'-biphenyl]-4-yl)piperidine-2-carboxamide (hereinafter referred to as the compound of Example 30) (0.155 g, 0.329 mmol, 65.6%) was obtained as a white solid.

$^1$H-NMR (400 MHz, CDCl$_3$) δ: 1.46-1.82 (m, 5H), 2.43 (d, J=13.1 Hz, 1H) 2.56 (dt, J=15.3, 6.2 Hz, 1H), 2.71-2.79 (m, 1H), 3.09-3.21 (m, 3H), 3.88 (d, J=13.1 Hz, 1H), 5.43 (d, J=5.0 Hz, 1H), 7.19 (d, J=8.2 Hz, 1H), 7.29-7.36 (m, 3H), 7.40-7.85 (m, 3H), 8.96 (br, 1H).

ESI-MS: m/z=470 (M+H)$^+$.

Example 31 Synthesis of 1-(3-acetamidepropanoyl)-N-(2-chloro-2'-(trifluoromethoxy)-[1,1'-biphenyl]-4-yl)piperidine-2-carboxamide

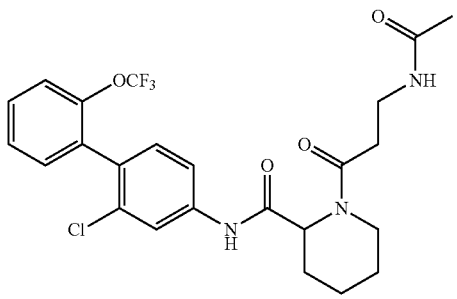 [SMILES: CC(=O)NCCC(=O)N1CCCCC1C(=O)Nc1ccc(-c2ccccc2OC(F)(F)F)c(Cl)c1]

According to the same procedure as in Example 3, except that the compound of Example 30 was used in place of the compound of Reference Example 3 and acetyl chloride was used in place of propionyl chloride, 1-(3-acetamidepropanoyl)-N-(2-chloro-2'-(trifluoromethoxy)-[1,1'-biphenyl]-4-yl)piperidine-2-carboxamide (hereinafter referred to as the compound of Example 31) (0.0218 g, 0.0420 mmol, 99.1%) was obtained as a white solid.

$^1$H-NMR (400 MHz, CDCl$_3$) δ: 1.46-1.94 (m, 5H), 1.98 (s, 3H), 2.34 (d, J=13.3 Hz, 1H), 2.60-2.73 (m, 2H), 3.20 (td, J=13.3, 2.4 Hz, 1H), 3.52-3.70 (m, 2H), 3.79 (d, J=13.3 Hz, 1H), 5.30 (d, J=4.5 Hz, 1H), 6.23 (br, 1H), 7.21 (d, J=8.2 Hz, 1H), 7.30-7.90 (m, 6H), 8.51 (br, 1H).

ESI-MS: m/z=512 (M+H)$^+$.

Example 32 Synthesis of N-(2-chloro-2'-(trifluoromethoxy)-[1,1'-biphenyl]-4-yl)-1-(3-(methylsulfonamide)propanoyl)piperidine-2-carboxamide

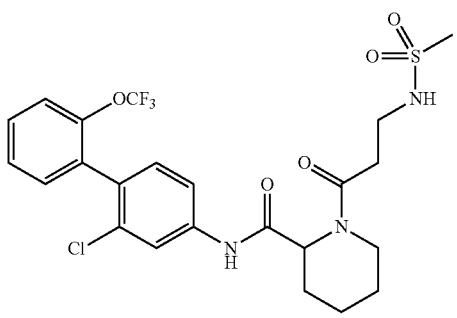 [SMILES: CS(=O)(=O)NCCC(=O)N1CCCCC1C(=O)Nc1ccc(-c2ccccc2OC(F)(F)F)c(Cl)c1]

According to the same procedure as in Example 3, except that the compound of Example 30 was used in place of the compound of Reference Example 3 and methanesulfonyl chloride was used in place of propionyl chloride, N-(2-chloro-2'-(trifluoromethoxy)-[1,1'-biphenyl]-4-yl)-1-(3-(methylsulfonamide)propanoyl)piperidine-2-carboxamide (hereinafter referred to as the compound of Example 32) (0.0224 g, 0.0409 mmol, 96.1%) was obtained as a white solid.

$^1$H-NMR (400 MHz, CDCl$_3$) δ: 1.50-1.90 (m, 5H), 2.33 (d, J=13.5 Hz, 1H), 2.75-2.80 (m, 2H) 3.00 (s, 3H), 3.22 (t, J=13.5 Hz, 1H), 3.45-3.51 (m, 2H), 3.77 (d, J=13.5 Hz, 1H), 5.26-5.30 (m, 2H), 7.22 (d, J=8.3 Hz, 1H), 7.30-7.44 (m, 5H), 7.80 (br, 1H), 8.22 (br, 1H).

ESI-MS: m/z=548 (M+H)+.

Example 33 Synthesis of N-(2-chloro-2'-(trifluoromethoxy)-[1,1'-biphenyl]-4-yl)-1-(3-(dimethylamino)propanoyl)piperidine-2-carboxamide

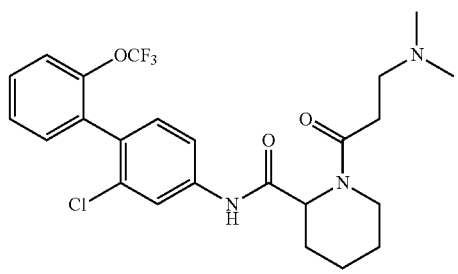

According to the same procedure as in Example 4, except that 3-(dimethylamino)propanoic acid hydrochloride was used as 2-methoxyacetic acid, N-(2-chloro-2'-(trifluoromethoxy)-[1,1'-biphenyl]-4-yl)-1-(3-(dimethylamino)propanoyl)piperidine-2-carboxamide (hereinafter referred to as the compound of Example 33) (0.0274 g, 0.0550 mmol, 73.2%) was obtained as a white solid.

$^1$H-NMR (400 MHz, CDCl$_3$) δ: 1.49-1.83 (m, 5H), 2.27 (s, 6H), 2.38-2.45 (m, 1H), 2.56-2.61 (m, 1H), 2.66-2.80 (m, 3H), 3.12-3.20 (m, 1H), 3.85-3.93 (m, 1H), 5.42 (d, J=5.4 Hz, 1H), 7.21 (d, J=8.3 Hz, 1H), 7.27-7.45 (m, 6H), 8.73 (br, 1H).

ESI-MS: m/z=498 (M+H).

Reference Example 22 Synthesis of tert-butyl (3-(2-((2-chloro-2'-(trifluoromethoxy)-[1,1'-biphenyl]-4-yl)carbamoyl)piperidin-1-yl)-3-oxopropyl)(methyl)carbamate

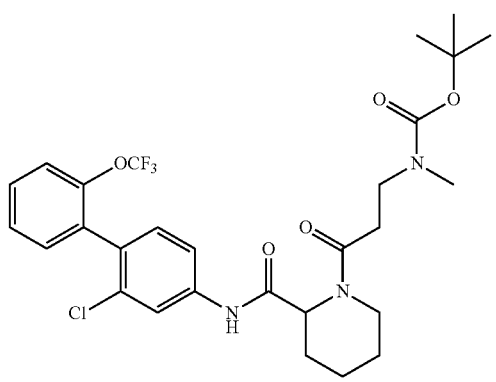 [SMILES: CN(CCC(=O)N1CCCCC1C(=O)Nc1ccc(-c2ccccc2OC(F)(F)F)c(Cl)c1)C(=O)OC(C)(C)C]

According to the same procedure as in Example 4, except that 3-((tert-butoxycarbonyl)(methyl)amino)propanoic acid was used in place of 2-methoxyacetic acid, tert-butyl (3-(2-((2-chloro-2'-(trifluoromethoxy)-[1,1'-biphenyl]-4-yl)carbamoyl)piperidin-1-yl)-3-oxopropyl)(methyl)carbamate (hereinafter referred to as the compound of Reference Example 22) (0.130 g, 0.223 mmol, 89.0%) was obtained as a white solid.

¹H-NMR (400 MHz, CDCl₃) δ: 1.35 (s, 9H), 1.30-1.77 (m, 5H), 2.37-2.80 (m, 3H), 2.93 (s, 3H), 3.18-3.30 (m, 2H) 3.84 (d, J=13.7 Hz, 1H), 3.95-4.03 (m, 1H), 5.38-5.42 (m, 1H), 7.20 (d, J=8.3 Hz, 1H), 7.31-7.46 (m, 4H), 7.66-7.72 (m, 1H), 7.90-7.92 (m, 1H), 9.10 (br, 1H).

ESI-MS: m/z=584 (M+H)⁺.

Example 34 Synthesis of N-(2-chloro-2'-(trifluoromethoxy)-[1,1'-biphenyl]-4-yl)-1-(3-(methylamino)propanoyl)piperidine-2-carboxamide

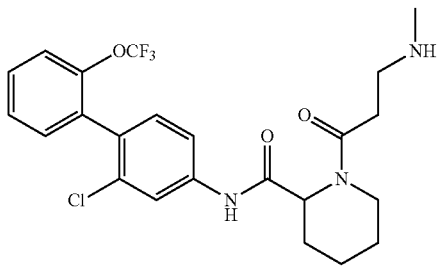 [SMILES: CNCCC(=O)N1CCCCC1C(=O)Nc1ccc(-c2ccccc2OC(F)(F)F)c(Cl)c1]

According to the same procedure as in Reference Example 5, except that the compound of Reference Example 22 was used in place of the compound of Reference Example 4, N-(2-chloro-2'-(trifluoromethoxy)-[1,1'-biphenyl]-4-yl)-1-(3-(methylamino)propanoyl)piperidine-2-carboxamide (hereinafter referred to as the compound of Example 34) (0.804 g, 0.166 mmol, 74.6%) was obtained as a white solid.

¹H-NMR (400 MHz, CDCl₃) δ: 1.46-1.83 (m, 5H), 2.47 (s, 3H), 2.40-2.48 (m, 1H), 2.75-2.83 (m, 1H), 2.94-2.99 (m, 2H), 3.16 (td, J=13.1, 2.6 Hz, 1H), 3.88 (d, J=13.1 Hz, 1H), 5.41 (d, J=5.4 Hz, 1H), 7.21 (d, J=8.3 Hz, 1H), 7.30-7.81 (m, 6H), 8.80 (br, 1H).

ESI-MS: m/z=484 (M+H)⁺.

Example 35 Synthesis of N-(2-chloro-2'-(trifluoromethoxy)-[1,1'-biphenyl]-4-yl)-1-(3-(N-methylacetamide)propanoyl)piperidine-2-carboxamide

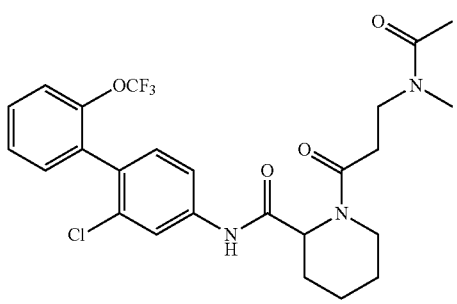 [SMILES: CC(=O)N(C)CCC(=O)N1CCCCC1C(=O)Nc1ccc(-c2ccccc2OC(F)(F)F)c(Cl)c1]

According to the same procedure as in Example 3, except that the compound of Example 34 was used in place of the compound of Reference Example 3 and acetyl chloride was used in place of propionyl chloride, N-(2-chloro-2'-(trifluoromethoxy)-[1,1'-biphenyl]-4-yl)-1-(3-(N-methylacetamide)propanoyl)piperidine-2-carboxamide (hereinafter referred to as the compound of Example 35) (0.0316 g, 0.0601 mmol, 74.5%) was obtained as a white solid.

¹H-NMR (400 MHz, CDCl₃) δ: 1.48-1.77 (m, 5H), 2.09 (s, 3H), 2.45 (d, J=13.7 Hz, 1H), 2.59-2.79 (m, 2H), 3.11 (s, 3H), 3.20-3.29 (m, 2H), 3.84 (d, J=13.7 Hz, 1H), 4.21-4.28 (m, 1H), 5.35 (d, J=5.1 Hz, 1H), 7.20 (d, J=8.3 Hz, 1H), 7.31-7.36 (m, 3H), 7.38-7.44 (m, 1H), 7.70-7.80 (m, 1H), 7.97-8.06 (m, 1H), 9.09 (br, 1H).

ESI-MS: m/z=526 (M+H)+.

Example 36 Synthesis of N-(2-chloro-2'-(trifluoromethoxy)-[1,1'-biphenyl]-4-yl)-1-(3-(N-methylmethylsulfonamide)propanoyl)piperidine-2-carboxamide

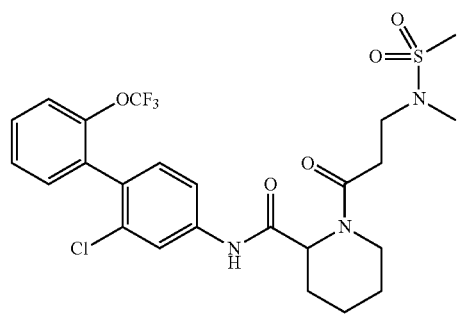 [SMILES: CN(CCC(=O)N1CCCCC1C(=O)Nc1ccc(-c2ccccc2OC(F)(F)F)c(Cl)c1)S(C)(=O)=O]

According to the same procedure as in Example 3, except that the compound of Example 34 was used in place of the compound of Reference Example 3 and methanesulfonyl chloride was used in place of propionyl chloride, N-(2-chloro-2'-(trifluoromethoxy)-[1,1'-biphenyl]-4-yl)-1-(3-(N-methylmethylsulfonamide)propanoyl)piperidine-2-carboxamide (hereinafter referred to as the compound of Example 36) (0.0380 g, 0.0676 mmol, 86.2%) was obtained as a white solid.

¹H-NMR (400 MHz, CDCl₃) δ: 1.50-1.98 (m, 5H), 2.35 (d, J=13.5 Hz, 1H), 2.76 (dt, J=15.9, 7.0 Hz, 1H), 2.86 (s, 3H), 2.83-2.89 (m, 1H), 2.95 (s, 3H), 3.20 (td, J=13.5, 2.7 Hz, 1H), 3.50-3.57 (m, 2H), 3.85 (d, J=13.5 Hz, 1H), 5.31 (d, J=5.0 Hz, 1H), 7.21 (d, J=8.2 Hz, 1H), 7.30-7.36 (m, 3H), 7.40-7.52 (m, 2H), 7.80-7.83 (m, 1H), 8.42 (br, 1H).

ESI-MS: m/z=584 (M+H)+.

Reference Example 23 Synthesis of N-(2-chloro-2'-(trifluoromethoxy)-[1,1-biphenyl]-4-yl)-1-(2-(ethylamino)acetyl)piperidine-2-carboxamide

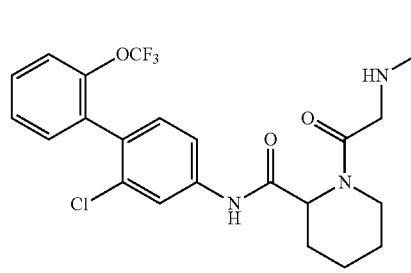

To a dichloromethane (1.0 mL) solution of the compound of Reference Example 5 (0.0400 g, 0.0877 mmol), a dichloromethane (0.0600 mL) solution of acetaldehyde (0.00464 g, 0.105 mmol), acetic acid (0.000502 mL, 0.00877 mmol), and sodium triacetoxyborohydride (0.0279 m g, 0.132 mmol) were added at 0° C. and the temperature was raised to room temperature, followed by stirring for 2.5 hours. To the reaction solution, an aqueous saturated sodium hydrogen carbonate solution was added, and the solution was extracted with chloroform. The organic layer was washed with saturated brine, dried over anhydrous sodium sulfate and filtered, and then the filtrate was concentrated under reduced pressure. The residue was purified by column chromatography (amine silica gel, n-hexane/ethyl acetate=40/60 to 0/100) to obtain N-(2-chloro-2'-(trifluoromethoxy)-[1,1'-biphenyl]-4-yl)-1-(2-(ethylamino)acetyl)piperidine-2-carboxamide (hereinafter referred to as the compound of Reference Example 23) (0.0193 g, 0.00399 mmol, 45.5%) as a white solid.

$^1$H-NMR (400 MHz, CDCl$_3$) δ: 1.17 (t, J=7.1 Hz, 3H), 1.38-1.80 (m, 5H), 1.90-2.00 (m, 1H), 2.30-2.45 (m, 1H), 2.55-2.90 (m, 2H), 3.16 (t, J=13.3 Hz, 1H), 3.56 (s, 2H), 3.70-3.76 (m, 1H), 5.29 (d, J=4.9 Hz, 1H), 7.20-7.45 (m, 6H), 7.70-7.90 (m, 1H), 8.46 (s, 1H).

ESI-MS: m/z=484 (M+H)$^+$.

Example 37 Synthesis of N-(2-chloro-2'-(trifluoromethoxy)-[1,1'-biphenyl]-4-yl)-1-(2-(N-ethylmethylsulfonamide)acetyl)piperidine-2-carboxamide

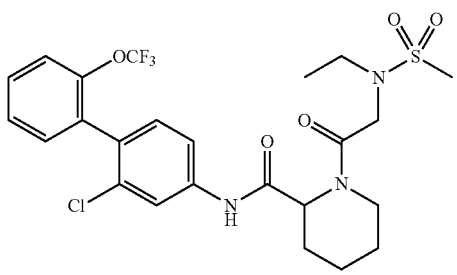 [SMILES: CCN(CC(=O)N1CCCCC1C(=O)Nc1ccc(-c2ccccc2OC(F)(F)F)c(Cl)c1)S(C)(=O)=O]

According to the same procedure as in Example 3, except that the compound of Reference Example 23 was used in place of the compound of Reference Example 3 and methanesulfonyl chloride was used in place of propionyl chloride, N-(2-chloro-2'-(trifluoromethoxy)-[1,1'-biphenyl]-4-yl)-1-(2-(N-ethylmethylsulfonamide)acetyl)piperidine-2-carboxamide (hereinafter referred to as the compound of Example 37) (0.0175 g, 0.0311 mmol, 78.1%) was obtained as a white solid.

$^1$H-NMR (400 MHz, CDCl$_3$) δ: 1.25 (t, J=7.1 Hz, 3H), 1.50-1.90 (m, 5H), 2.38 (d, J=13.0 Hz, 1H), 3.07 (s, 3H), 3.25 (t, J=13.0 Hz, 1H), 3.43 (q, J=7.1 Hz, 2H), 3.76 (d, J=13.0 Hz, 1H), 4.14 (d, J=17.0 Hz, 1H), 4.30 (d, J=17.0 Hz, 1H), 5.27 (d, J=4.6 Hz, 1H), 7.21 (d, J=8.3 Hz, 1H), 7.29-7.36 (m, 3H), 7.40-7.45 (m, 2H), 7.83-7.85 (m, 1H), 8.23 (br, 1H).

ESI-MS: m/z=584 (M+Na)$^+$.

Reference Example 24 Synthesis of tert-butyl (R)-(3-(2-((2-chloro-2'-(trifluoromethoxy)-[1,1'-biphenyl]-4-yl)carbamoyl)piperidin-1-yl)-3-oxopropyl)carbamate

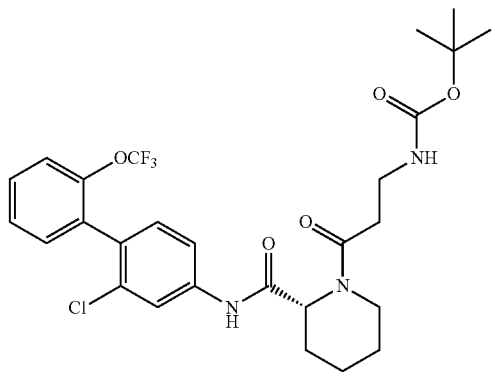 [SMILES: CC(C)(C)OC(=O)NCCC(=O)N1CCCC[C@@H]1C(=O)Nc1ccc(-c2ccccc2OC(F)(F)F)c(Cl)c1]

According to the same procedure as in Example 4, except that 3-((tert-butoxycarbonyl)amino)propanoic acid was used in place of 2-methoxyacetic acid and the compound of Reference Example 8 was used in place of the compound of Reference Example 3, tert-butyl (R)-(3-(2-((2-chloro-2'-(trifluoromethoxy)-[1,1'-biphenyl]-4-yl)carbamoyl)piperidin-1-yl)-3-oxopropyl)carbamate (hereinafter referred to as the compound of Reference Example 24) (0.104 g, 0.182 mmol, 96.7%) was obtained as a white solid.

$^1$H-NMR (400 MHz, CDCl$_3$) δ: 1.39 (s, 9H), 1.50-1.90 (5H, m), 2.35 (d, J=13.7 Hz, 1H), 2.55-2.75 (m, 2H), 3.20 (t, J=12.8 Hz, 1H), 3.41-3.49 (m, 1H), 3.50-3.60 (m, 1H), 3.80 (d, J=13.7 Hz, 1H), 5.17 (br, 1H), 5.33 (d, J=4.9 Hz, 1H), 7.20 (d, J=8.3 Hz, 1H), 7.29-7.60 (m, 5H), 7.70-7.89 (m, 11-H), 8.65 (br, 111).

ESI-MS: m/z=570 (M+H)$^+$.

Example 38 Synthesis of (R)-1-(3-aminopropanoyl)-N-(2-chloro-2'-(trifluoromethoxy)-[1,1'-biphenyl]-4-yl)piperidine-2-carboxamide

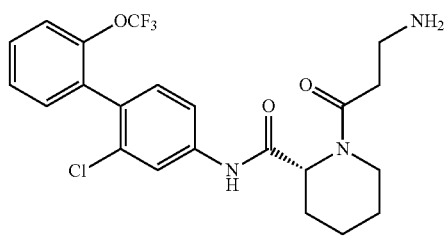

According to the same procedure as in Reference Example 5, except that the compound of Reference Example 24 was used in place of the compound of Reference Example 4, (R)-1-(3-aminopropanoyl)-N-(2-chloro-2'-(trifluoromethoxy)-[1,1'-biphenyl]-4-yl)piperidine-2-carboxamide (hereinafter referred to as the compound of Example 38) (0.497 g, 0.106 mmol, 58.5%) was obtained as a white solid.

¹H-NMR (400 MHz, CDCl₃) δ: 1.46-1.82 (m, 5H), 2.43 (d, J=13.1 Hz, 1H) 2.56 (dt, J=15.3, 6.2 Hz, 1H), 2.71-2.79 (m, 1H), 3.09-3.21 (m, 3H), 3.88 (d, J=13.1 Hz, 1H), 5.43 (d, J=5.0 Hz, 1H), 7.19 (d, J=8.2 Hz, 1H), 7.29-7.36 (m, 3H), 7.40-7.85 (m, 3H), 8.96 (br, 1H).

ESI-MS: m/z=470 (M+H)⁺.

Example 39 Synthesis of N-(2-chloro-2'-(trifluoromethoxy)-[1,1'-biphenyl]-4-yl)-1-(3-(methylthio)propanoyl)piperidine-2-carboxamide

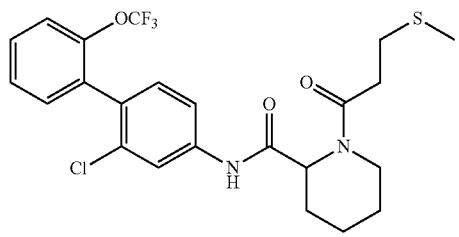 [SMILES: CSCCC(=O)N1CCCCC1C(=O)Nc1ccc(-c2ccccc2OC(F)(F)F)c(Cl)c1]

According to the same procedure as in Example 4, except that 3-(methylthio)propanoic acid was used in place of 2-methoxyacetic acid, N-(2-chloro-2'-(trifluoromethoxy)-[1,1'-biphenyl]-4-yl)-1-(3-(methylthio)propanoyl)piperidine-2-carboxamide (hereinafter referred to as the compound of Example 39) (0.0489 g, 0.0976 mmol, 97.4%) was obtained as a white solid.

¹H-NMR (400 MHz, CDCl₃) δ: 1.51-1.90 (m, 5H), 2.18 (s, 3H), 2.36 (d, J=13.9 Hz, 1H), 2.68-2.77 (m, 1H), 2.80-2.99 (m, 3H), 3.17 (td, J=13.2, 2.6 Hz, 1H), 3.86 (d, J=12.4 Hz, 1H), 5.37 (d, J=4.9 Hz, 1H), 7.20 (d, J=8.3 Hz, 1H), 7.30-7.52 (m, 5H), 7.66-7.90 (m, 1H), 8.49 (br, 1H).

ESI-MS: m/z=501 (M+H)⁺.

Example 40 Synthesis of N-(2-chloro-2'-(trifluoromethoxy)-[1,1'-biphenyl]-4-yl)-1-(3-(methylsulfonyl)propanoyl)piperidine-2-carboxamide

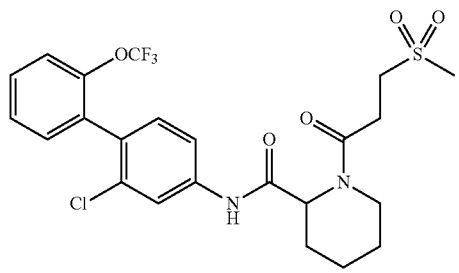 [SMILES: CS(=O)(=O)CCC(=O)N1CCCCC1C(=O)Nc1ccc(-c2ccccc2OC(F)(F)F)c(Cl)c1]

To a dichloromethane (1.0 mL) solution of the compound of Example 39 (0.0480 g, 0.0958 mmol), 3-chloroperbenzoic acid (0.0496 g, 0.287 mmol) was added at 0° C. and the temperature was raised to room temperature, followed by stirring for 17 hours. To the reaction solution, an aqueous saturated sodium thiosulfate solution and saturated sodium hydrogen carbonate were added, and the solution was extracted with chloroform. The organic layer was washed with saturated brine, dried over anhydrous sodium sulfate and filtered, and then the filtrate was concentrated under reduced pressure. The residue was purified by column chromatography (silica gel, n-hexane/ethyl acetate=50/50 to 25/75) to obtain N-(2-chloro-2'-(trifluoromethoxy)-[1,1'-biphenyl]-4-yl)-1-(3-(methylsulfonyl)propanoyl)piperidine-2-carboxamide (hereinafter referred to as the compound of Example 40) (0.0412 g, 0.0773 mmol, 80.6%) as a white solid.

¹H-NMR (400 MHz, CDCl₃) δ: 1.50-1.82 (m, 5H), 2.45-2.48 (m, 1H), 2.79 (td, J=11.0, 5.9 Hz, 1H), 3.06 (s, 3H), 3.18-3.27 (m, 2H), 3.40 (dt, J=13.8, 5.5 Hz, 1H), 3.77-3.79 (m, 1H), 3.93-3.96 (m, 1H), 5.41 (d, J=5.4 Hz, 1H), 7.20 (d, J=8.5 Hz, 1H), 7.30-7.36 (m, 3H), 7.40-7.44 (m, 1H), 7.51-7.53 (m, 1H), 7.86-7.89 (m, 1H), 8.28 (br, 1H).

ESI-MS: m/z=533 (M+H)⁺.

Reference Example 25 Synthesis of tert-butyl (R)-(3-(2-((2-chloro-2'-(trifluoromethoxy)-[1,1'-biphenyl]-4-yl)carbamoyl)piperidin-1-yl)-3-oxopropyl)(methyl)carbamate

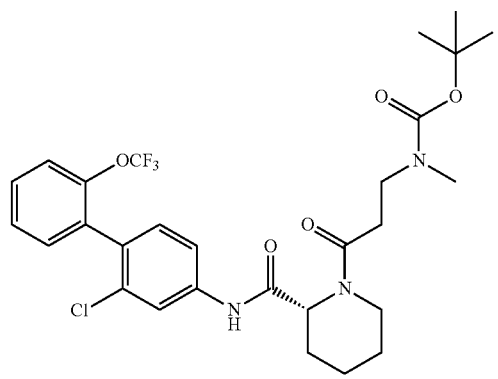 [SMILES: CN(CCC(=O)N1CCCC[C@@H]1C(=O)Nc1ccc(-c2ccccc2OC(F)(F)F)c(Cl)c1)C(=O)OC(C)(C)C]

According to the same procedure as in Example 4, except that 3-((tert-butoxycarbonyl)(methyl)amino)propanoic acid was used in place of 2-methoxyacetic acid and the compound of Reference Example 8 was used in place of the compound of Reference Example 3, tert-butyl (R)-(3-(2-((2-chloro-2'-(trifluoromethoxy)-[1,1'-biphenyl]-4-yl)carbamoyl)piperidin-1-yl)-3-oxopropyl)(methyl)carbamate (hereinafter referred to as the compound of Reference Example 25) (0.117 g, 0.201 mmol, 91.5%) was obtained as a white solid.

¹H-NMR (400 MHz, CDCl₃) δ: 1.35 (s, 9H), 1.30-1.77 (m, 5H), 2.37-2.80 (m, 3H), 2.93 (s, 3H), 3.18-3.30 (m, 2H), 3.84 (d, J=13.7 Hz, 1H), 3.95-4.03 (m, 1H), 5.38-5.42 (m, 1H), 7.20 (d, J=8.3 Hz, 1H), 7.31-7.46 (m, 4H), 7.66-7.72 (m, 1H), 7.90-7.92 (m, 1H), 9.10 (br, 1H).

ESI-MS: m/z=584 (M+H)⁺.

Example 41 Synthesis of (R)—N-(2-chloro-2'-(trifluoromethoxy)-[1,1'-biphenyl]-4-yl)-1-(3-(methylamino)propanoyl)piperidine-2-carboxamide

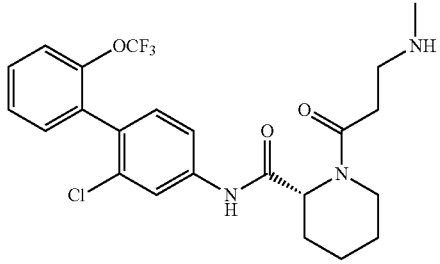 [SMILES: CNCCC(=O)N1CCCC[C@@H]1C(=O)Nc1ccc(-c2ccccc2OC(F)(F)F)c(Cl)c1]

According to the same procedure as in Reference Example 5, except that the compound of Reference Example 25 was used in place of the compound of Reference Example 4, (R)—N-(2-chloro-2'-(trifluoromethoxy)-[1,1'-biphenyl]-4-yl)-1-(3-(methylamino)propanoyl)piperidine-2-carboxamide (hereinafter referred to as the compound of Example 41) (0.748 g, 0.155 mmol, 77.1%) was obtained as a white solid.

$^1$H-NMR (400 MHz, CDCl$_3$) δ: 1.46-1.83 (m, 5H), 2.47 (s, 3H), 2.40-2.48 (m, 1H), 2.75-2.83 (m, 1H), 2.94-2.99 (m, 2H), 3.16 (td, J=13.1, 2.6 Hz, 1H), 3.88 (d, J=13.1 Hz, 1H), 5.41 (d, J=5.4 Hz, 1H), 7.21 (d, J=8.3 Hz, 1H), 7.30-7.81 (m, 6H), 8.80 (br, 1H).

ESI-MS: m/z=484 (M+H)$^+$.

Example 42 Synthesis of N-(2-chloro-2'-(trifluoromethoxy)-[1,1'-biphenyl]-4-yl)-1-(3-hydroxypropanoyl)piperidine-2-carboxamide

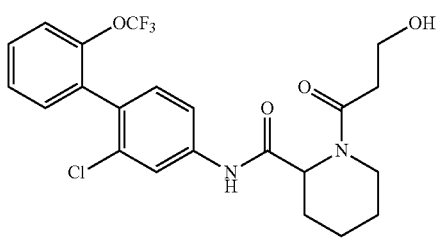 [SMILES: O=C(Nc1ccc(-c2ccccc2OC(F)(F)F)c(Cl)c1)C1CCCCN1C(=O)CCO]

According to the same procedure as in Example 4, except that 3-hydroxypropanoic acid was used in place of 2-methoxyacetic acid, N-(2-chloro-2'-(trifluoromethoxy)-[1,1'-biphenyl]-4-yl)-1-(3-hydroxypropanoyl)piperidine-2-carboxamide (hereinafter referred to as the compound of Example 42) (0.212 g, 0.450 mmol, 59.9%) was obtained as a white solid.

$^1$H-NMR (400 MHz, CDCl$_3$) δ: 1.50-1.92 (m, 4H), 2.35 (d, J=14.1 Hz, 1H), 2.64-2.80 (m, 2H), 3.06 (t, J=6.3 Hz, 1H), 3.19 (td, J=13.2, 2.4 Hz, 1H), 3.83 (d, J=14.1 Hz, 1H), 3.98 (q, J=5.4 Hz, 2H), 5.34 (d, J=5.4 Hz, 1H), 7.21 (d, J=8.0 Hz, 1H), 7.30-7.44 (m, 6H), 7.70-7.90 (brm, 1H), 8.39 (br, 1H).

ESI-MS: m/z=471 (M+H)$^+$.

Example 43 Synthesis of methyl 3-(2-((2-chloro-2'-(trifluoromethoxy)-[1,1'-biphenyl]-4-yl)carbamoyl)piperidin-1-yl)-3-oxopropanoate

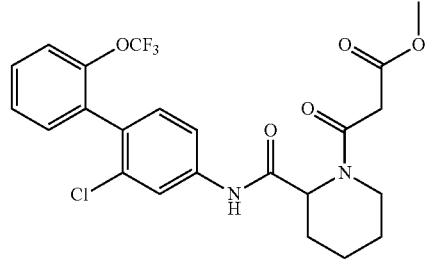 [SMILES: COC(=O)CC(=O)N1CCCCC1C(=O)Nc1ccc(-c2ccccc2OC(F)(F)F)c(Cl)c1]

According to the same procedure as in Example 3, except that methyl 3-chloro-3-oxopropanoate was used in place of propionyl chloride, methyl 3-(2-((2-chloro-2'-(trifluoromethoxy)-[1,1'-biphenyl]-4-yl)carbamoyl)piperidin-1-yl)-3-oxopropanoate (hereinafter referred to as the compound of Example 43) (0.0500 g, 0.100 mmol, 80.0%) was obtained as a white solid.

$^1$H-NMR (400 MHz, CDCl$_3$) δ: 1.50-1.80 (m, 5H), 2.57-2.62 (m, 1H), 3.16-3.25 (m, 1H), 3.57 (d, J=17.2 Hz, 1H), 3.59-3.65 (m, 1H), 3.84 (s, 3H), 3.85 (d, J=17.2 Hz, 2H), 5.49 (s, 1H), 7.22 (d, J=8.2 Hz, 1H), 7.30-7.37 (m, 3H), 7.40-7.44 (m, 1H), 7.92-7.95 (m, 1H), 8.87 (br, 1H).

ESI-MS: m/z=499 (M+H)$^+$.

Example 44 Synthesis of methyl 4-(2-((2-chloro-2'-(trifluoromethoxy)-[1,1'-biphenyl]-4-yl)carbamoyl)piperidin-1-yl)-4-oxobutanoate

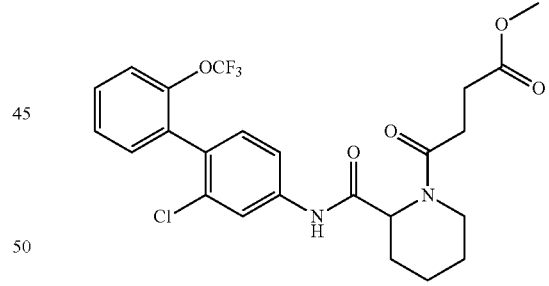

According to the same procedure as in Example 3, except that methyl 4-chloro-4-oxobutanoate was used in place of propionyl chloride, methyl 4-(2-((2-chloro-2'-(trifluoromethoxy)-[1,1'-biphenyl]-4-yl)carbamoyl)piperidin-1-yl)-4-oxobutanoate (hereinafter referred to as the compound of Example 44) (0.0390 g, 0.0760 mmol, quantitative) was obtained as a white solid.

$^1$H-NMR (400 MHz, CDCl$_3$) δ: 1.52-1.60 (m, 5H), 2.42-2.60 (m, 2H), 2.62-2.70 (m, 1H), 2.88-2.96 (m, 1H), 2.99-3.08 (m, 1H), 3.22 (d, J=14.6 Hz, 1H), 3.74 (s, 3H), 3.97 (d, J=14.6 Hz, 1H), 5.46 (d, J=5.4 Hz, 1H), 7.21 (d, J=8.3 Hz, 1H), 7.28-7.44 (m, 6H), 8.49 (br, 1H).

ESI-MS: m/z=513 (M+H)$^+$.

Example 45 Synthesis of N-(2-chloro-2'-(trifluoromethoxy)-[1,1'-biphenyl]-4-yl)-1-(3-methoxypropanoyl)piperidine-2-carboxamide

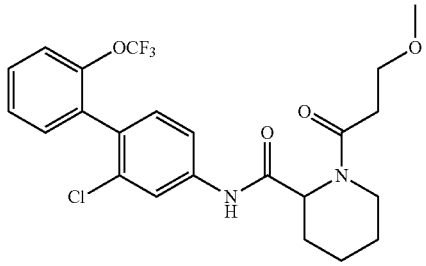 [SMILES: COCCC(=O)N1CCCCC1C(=O)Nc1ccc(-c2ccccc2OC(F)(F)F)c(Cl)c1]

According to the same procedure as in Reference Example 2, except that 1-(3-methoxypropanoyl)piperidine-2-carboxylic acid was used in place of 1-(tert-butoxycarbonyl)piperidine-2-carboxylic acid, N-(2-chloro-2'-(trifluoromethoxy)-[1,1'-biphenyl]-4-yl)-1-(3-methoxypropanoyl)piperidine-2-carboxamide (hereinafter referred to as the compound of Example 45) (0.0467 g, 0.0963 mmol, 50.6%) was obtained as a white solid.

$^1$H-NMR (400 MHz, CDCl$_3$) δ: 1.46-1.87 (m, 5H), 2.39 (d, J=13.9 Hz, 1H), 2.64 (dt, J=15.0, 5.7 Hz, 1H), 2.85-2.92 (m, 1H), 3.14 (td, J=13.1, 2.3 Hz, 1H), 3.38 (s, 3H), 3.67-3.78 (m, 1H), 3.81-3.86 (m, 1H), 3.92 (d, J=13.9 Hz, 1H), 5.40 (d, J=4.9 Hz, 1H), 7.21 (d, J=8.3 Hz, 1H), 7.29-7.80 (m, 6H), 8.46 (s, 1H).

ESI-MS: m/z=483 (M−H)$^-$.

Example 46 Synthesis of N-(2-chloro-2'-(trifluoromethoxy)-[1,1'-biphenyl]-4-yl)-1-(1-methyl-1H-pyrazole-4-carbonyl)piperidine-2-carboxamide

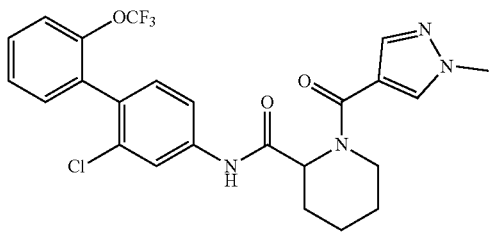 [SMILES: Cn1cc(C(=O)N2CCCCC2C(=O)Nc2ccc(-c3ccccc3OC(F)(F)F)c(Cl)c2)cn1]

According to the same procedure as in Example 4, except that 1-methyl-1H-pyrazole-4-carboxylic acid was used in place of 2-methoxyacetic acid, N-(2-chloro-2'-(trifluoromethoxy)-[1,1'-biphenyl]-4-yl)-1-(1-methyl-1H-pyrazole-4-carbonyl)piperidine-2-carboxamide (hereinafter referred to as the compound of Example 46) (0.0314 g, 0.0619 mmol, 82.4%) was obtained as a white solid.

$^1$H-NMR (400 MHz, CDCl$_3$) δ: 1.62-1.71 (m, 2H), 1.78-1.87 (m, 2H), 1.99-2.11 (m, 1H), 2.37 (d, J=12.9 Hz, 1H), 3.08-3.21 (m, 1H), 3.96 (s, 3H), 4.13-4.23 (m, 1H), 5.18-5.20 (m, 1H), 7.22 (d, J=8.3 Hz, 1H), 7.27-7.90 (m, 6H), 7.70 (s, 1H), 7.81 (s, 1H), 9.18 (br, 1H).

ESI-MS: m/z=507 (M+H)$^+$.

Example 47 Synthesis of N-(2-chloro-2'-(trifluoromethoxy)-[1,1'-biphenyl]-4-yl)-1-(1-methyl-1H-imidazole-4-carbonyl)piperidine-2-carboxamide

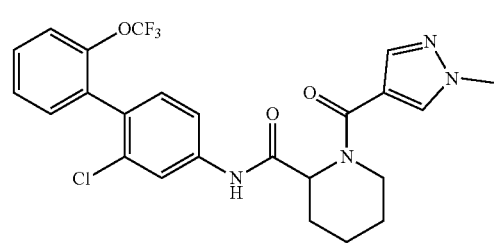

According to the same procedure as in Example 4, except that 1-methyl-1H-imidazole-4-carboxylic acid was used in place of 2-methoxyacetic acid, N-(2-chloro-2'-(trifluoromethoxy)-[1,1'-biphenyl]-4-yl)-1-(1-methyl-1H-imidazole-4-carbonyl)piperidine-2-carboxamide (hereinafter referred to as the compound of Example 47) (0.0369 g, 0.0728 mmol, 96.9%) was obtained as a white solid.

$^1$H-NMR (400 MHz, CDCl$_3$) δ: 1.45-1.83 (m, 4H), 2.15-2.32 (m, 2H), 2.75-2.87 (m, 1H), 3.79 (s, 3H), 4.55-4.65 (m, 1H), 5.31-5.37 (m, 1H), 7.21 (d, J=8.3 Hz, 1H), 7.31-7.63 (m, 7H), 7.75-7.90 (m, 1H), 11.47 (br, 1H).

ESI-MS: m/z=507 (M+H)$^+$.

Example 48 Synthesis of N-(2-chloro-2'-(trifluoromethoxy)-[1,1'-biphenyl]-4-yl)-1-(1H-pyrazole-4-carbonyl)piperidine-2-carboxamide

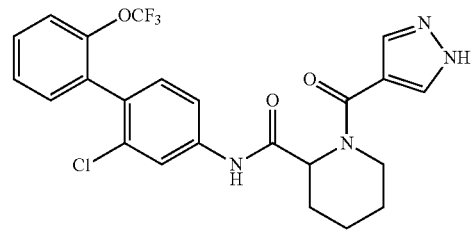 [SMILES: O=C(Nc1ccc(-c2ccccc2OC(F)(F)F)c(Cl)c1)C1CCCCN1C(=O)c1cn[nH]c1]

According to the same procedure as in Example 4, except that 1H-pyrazole-4-carboxylic acid was used in place of 2-methoxyacetic acid, N-(2-chloro-2'-(trifluoromethoxy)-[1,1'-biphenyl]-4-yl)-1-(1H-pyrazole-4-carbonyl)piperidine-2-carboxamide (hereinafter referred to as the compound of Example 48) (0.0163 g, 0.0331 mmol, 44.0%) was obtained as a white solid.

$^1$H-NMR (400 MHz, CDCl$_3$) δ: 1.45-1.90 (m, 4H), 1.95-2.17 (m, 1H), 2.33-2.43 (m, 1H), 3.15-3.26 (m, 1H), 4.09-4.21 (m, 1H), 5.20-5.27 (m, 1H), 7.22 (d, J=8.5 Hz, 1H), 7.28-7.52 (m, 5H), 7.70-8.00 (m, 3H), 9.16 (br, 1H), 10.79 (br, 1H).

ESI-MS: m/z=493 (M+H)$^+$.

Reference Example 26 Synthesis of methyl 1-(2-(N-methylmethylsulfonamide)acetyl)piperidine-2-carboxylate

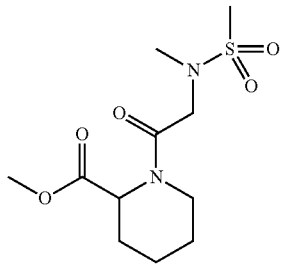 [SMILES: COC(=O)C1CCCCN1C(=O)CN(C)S(C)(=O)=O]

According to the same procedure as in Example 4, except that the compound of Reference Example 20 was used in place of 2-methoxyacetic acid and methyl piperidine-2-carboxylate hydrochloride was used in place of the compound of Reference Example 3, 1-(2-(N-methylmethylsulfonamide)acetyl)piperidine-2-carboxylic acidmethyl (hereinafter referred to as the compound of Reference Example 26) (0.934 g, 3.19 mmol, 82.0) was obtained as a white solid.

$^1$H-NMR (400 MHz, CDCl$_3$) δ: 1.24-1.76 (m, 5H), 2.25-2.32 (m, 1H), 2.99 (s, 3H), 3.00 (s, 3H), 3.25 (td, J=13.0, 3.2 Hz, 1H), 3.58-3.64 (m, 1H), 3.75 (d, J=4.6 Hz, 3H), 4.11 (d, J=17.1 Hz, 1H), 4.30 (d, J=17.1 Hz, 1H), 5.25 (d, J=5.6 Hz, 1H).

ESI-MS: m/z=293 (M+H).

Reference Example 27 Synthesis of 1-(2-(N-methylmethylsulfonamide)acetyl)piperidine-2-carboxylic acid

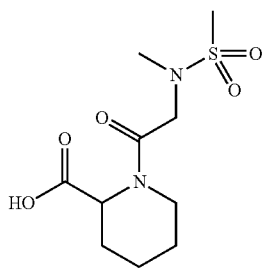 [SMILES: CN(CC(=O)N1CCCCC1C(=O)O)S(C)(=O)=O]

To a methanol (10.0 mL) solution of the compound of Reference Example 26 (0.933 g, 3.19 mmol), an aqueous 1M sodium hydroxide solution (3.83 mL, 3.83 mmol) was added at 0° C. and the temperature was raised to room temperature, followed by stirring for 17 hours. To the reaction solution, 1M hydrochloric acid was added, and the solution was extracted with chloroform. The organic layer was washed with saturated brine, dried over anhydrous sodium sulfate and filtered, and then the filtrate was concentrated under reduced pressure to obtain crude 1-(2-(N-methylmethylsulfonamide)acetyl)piperidine-2-carboxylic acid (hereinafter referred to as the compound of Reference Example 27) (0.812 g) as a white solid. The compound of Reference Example 27 was directly used for the subsequent reaction.

$^1$H-NMR (400 MHz, CDCl$_3$) δ: 1.18-1.75 (m, 5H), 2.30 (d, J=13.1 Hz, 1H), 2.98 (s, 3H), 2.99 (s, 3H), 3.24 (t, J=12.0 Hz, 1H), 3.63 (d, J=13.1 Hz, 1H), 4.13 (d, J=17.2 Hz, 1H), 4.27 (d, J=17.2 Hz, 1H), 5.24 (d, J=4.1 Hz, 1H).

ESI-MS: m/z=279 (M+H)$^+$.

Reference Example 28 Synthesis of N-(4-bromo-3-chlorophenyl)-1-(2-(N-methylmethylsulfonamide)acetyl)piperidine-2-carboxamide

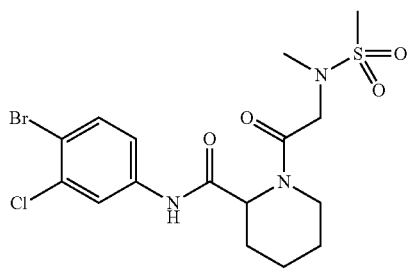 [SMILES: CN(CC(=O)N1CCCCC1C(=O)Nc1ccc(Br)c(Cl)c1)S(C)(=O)=O]

According to the same procedure as in Reference Example 2, except that the compound of Reference Example 27 was used in place of 1-(tert-butoxycarbonyl)piperidine-2-carboxylic acid and 4-bromo-3-chloroaniline was used in place of the compound of Reference Example 1, N-(4-bromo-3-chlorophenyl)-1-(2-(N-methylmethylsulfonamide)acetyl)piperidine-2-carboxamide (hereinafter referred to as the compound of Reference Example 28) (0.296 g, 0.634 mmol, 58.8%) was obtained as a white solid.

$^1$H-NMR (400 MHz, CDCl$_3$) δ: 1.49-1.85 (m, 5H), 2.34 (d, J=12.8 Hz, 1H), 3.03 (s, 3H), 3.03 (s, 3H), 3.20 (t, J=12.8 Hz, 1H), 3.71 (d, J=12.8 Hz, 1H), 4.12 (d, J=16.7 Hz, 1H), 4.23 (d, J=16.7 Hz, 1H), 5.22 (d, J=4.9 Hz, 1H), 7.20-7.24 (m, 1H), 7.50 (dd, J=8.5, 2.0 Hz, 1H), 7.84 (t, J=2.3 Hz, 1H), 8.20 (br, 111H).

ESI-MS: m/z=467 (M+H)$^+$.

Example 49 Synthesis of N-(2-chloro-2'-isopropoxy-[1,1'-biphenyl]-4-yl)-1-(2-(N-methylmethylsulfonamide)acetyl)piperidine-2-carboxamide

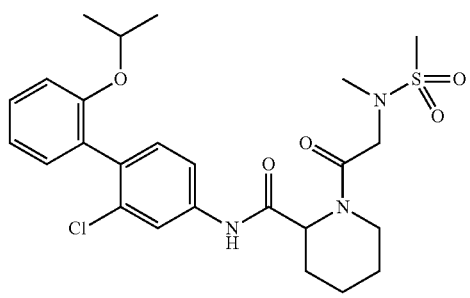 [SMILES: CC(C)Oc1ccccc1-c1ccc(NC(=O)C2CCCCN2C(=O)CN(C)S(C)(=O)=O)cc1Cl]

According to the same procedure as in Reference Example 1, except that 2-isopropoxyphenylboronic acid was used in place of 2-trifluoromethoxyphenylboronic acid and the compound of Reference Example 28 was used in place of 4-bromo-3-chloroaniline, N-(2-chloro-2'-isopropoxy-[1,1'-biphenyl]-4-yl)-1-(2-(N-methylmethylsulfonamide)acetyl)piperidine-2-carboxamide (hereinafter referred to as the compound of Example 49) (0.0253 g, 0.0485 mmol, 75.3%) was obtained as a white solid.

$^1$H-NMR (400 MHz, CDCl$_3$) δ: 1.20 (d, J=6.0 Hz, 6H), 1.50-1.88 (m, 5H), 2.31-2.39 (m, 1H), 3.05 (s, 3H), 3.05 (s, 3H), 3.21-3.28 (m, 1H), 3.69-3.74 (m, 1H), 4.19 (d, J=16.8 Hz, 1H), 4.25 (d, J=16.8 Hz, 1H), 4.41 (t, J=6.0 Hz, 1H), 5.23-5.26 (m, 1H), 6.95-7.00 (m, 2H), 7.17 (dd, J=7.4, 2.0 Hz, 1H), 7.22-7.37 (m, 3H), 7.76 (d, J=2.0 Hz, 1H), 8.11 (s, 1H).
ESI-MS: m/z=523 (M+H)$^+$.

Example 50 Synthesis of N-(2-chloro-2'-(trifluoromethoxy)-[1,1'-biphenyl]-4-yl)-1-(2-(1-methyl-1H-imidazol-2-yl)acetyl)piperidine-2-carboxamide

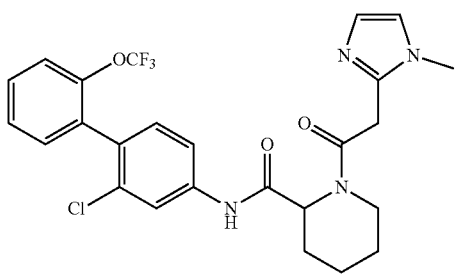 [SMILES: Cn1ccnc1CC(=O)N1CCCCC1C(=O)Nc1ccc(-c2ccccc2OC(F)(F)F)c(Cl)c1]

According to the same procedure as in Example 4, except that 2-(1-methyl-1H-imidazol-2-yl)acetic acid was used in place of 2-methoxyacetic acid, N-(2-chloro-2'-(trifluoromethoxy)-[1,1'-biphenyl]-4-yl)-1-(2-(1-methyl-1H-imidazol-2-yl)acetyl)piperidine-2-carboxamide (hereinafter referred to as the compound of Example 50) (0.0341 g, 0.0654 mmol, 87.0%) was obtained as a white solid.
$^1$H-NMR (400 MHz, CDCl$_3$) δ: 1.49-1.80 (m, 5H), 2.67-2.74 (m, 1H), 3.20-3.27 (m, 1H), 3.54-3.62 (m, 1H), 3.63 (s, 3H), 3.73 (d, J=15.9 Hz, 1H), 4.05 (d, J=15.9 Hz, 1H), 5.59-5.63 (m, 1H), 6.89-6.98 (m, 2H), 7.20-7.29 (m, 1H), 7.32-7.37 (m, 3H), 7.39-7.45 (m, 1H), 7.71-7.99 (m, 2H), 10.64 (br, 1H).
ESI-MS: m/z=521 (M+H)$^+$.

Reference Example 29 Synthesis of N-(4-bromo-3-fluorophenyl)-1-(2-(N-methylmethylsulfonamide)acetyl)piperidine-2-carboxamide

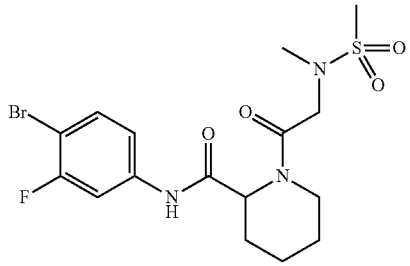 [SMILES: CN(CC(=O)N1CCCCC1C(=O)Nc1ccc(Br)c(F)c1)S(C)(=O)=O]

According to the same procedure as in Reference Example 2, except that the compound of Reference Example 27 was used in place of 1-(tert-butoxycarbonyl)piperidine-2-carboxylic acid and 4-bromo-3-fluoroaniline was used in place of the compound of Reference Example 1, N-(4-bromo-3-fluorophenyl)-1-(2-(N-methylmethylsulfonamide)acetyl)piperidine-2-carboxamide (hereinafter referred to as the compound of Reference Example 29) (0.0253 g, 0.0562 mmol, 52.1%) was obtained as a white solid.
$^1$H-NMR (400 MHz, CDCl$_3$) δ: 1.48-1.83 (m, 51H), 2.31-2.39 (m, 1H), 3.03 (s, 3H), 3.03 (s, 3H), 3.16-3.23 (m, 1H), 3.68-3.75 (m, 1H), 4.10 (d, J=16.6 Hz, 1H), 4.24 (d, J=16.6 Hz, 1H), 5.21-5.24 (m, 1H), 7.06 (dd, J=9.0, 2.0 Hz, 1H), 7.43 (t, J=8.2 Hz, 1H), 7.63 (dd, J=10.5, 2.4 Hz, 1H), 8.24 (br, 1H).
ESI-MS: m/z=451 (M+H)$^+$.

Example 51 Synthesis of N-(2-fluoro-2'-(trifluoromethoxy)-[1,1'-biphenyl]-4-yl)-1-(2-(N-methylmethylsulfonamide)acetyl)piperidine-2-carboxamide

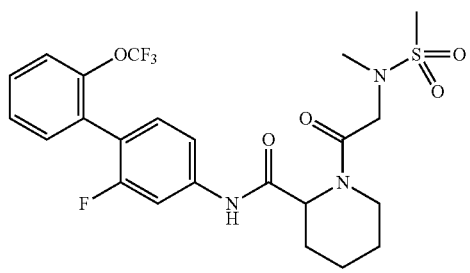 [SMILES: CN(CC(=O)N1CCCCC1C(=O)Nc1ccc(-c2ccccc2OC(F)(F)F)c(F)c1)S(C)(=O)=O]

According to the same procedure as in Reference Example 1, except that the compound of Reference Example 29 was used as 4-bromo-3-chloroaniline, N-(2-fluoro-2'-(trifluoromethoxy)-[1,1'-biphenyl]-4-yl)-1-(2-(N-methylmethylsulfonamide)acetyl)piperidine-2-carboxamide (hereinafter referred to as the compound of Example 51) (0.0132 g, 0.0248 mmol, 44.7%) was obtained as a white solid.
$^1$H-NMR (400 MHz, CDCl$_3$) δ: 1.45-1.90 (m, 5H), 2.33-2.41 (m, 1H), 3.05 (s, 6H), 3.20-3.29 (m, 1H), 3.69-3.76 (m, 1H), 4.17 (d, J=16.8 Hz, 1H), 4.25 (d, J=16.8 Hz, 1H), 5.23-5.27 (m, 1H), 7.20-7.44 (m, 6H), 7.62 (dd, J=11.7, 2.0 Hz, 1H), 8.24 (br, 1H).

Example 52 Synthesis of 1-(2-(1H-imidazol-1-yl)acetyl)-N-(2-chloro-2'-(trifluoromethoxy)-[1,1'-biphenyl]-4-yl)piperidine-2-carboxamide

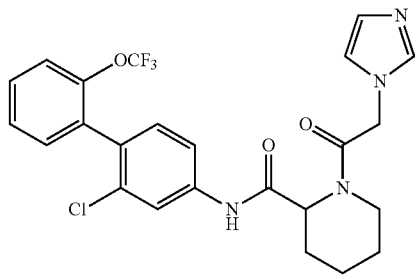 [SMILES: O=C(Nc1ccc(-c2ccccc2OC(F)(F)F)c(Cl)c1)C1CCCCN1C(=O)Cn1ccnc1]

According to the same procedure as in Example 4, except that 1-imidazoleacetic acid was used in place of 2-methoxyacetic acid, 1-(2-(1H-imidazol-1-yl)acetyl)-N-(2-chloro-2'-(trifluoromethoxy)-[1,1'-biphenyl]-4-yl)piperidine-2-carboxamide (hereinafter referred to as the compound of Example 52) (0.0189 g, 0.0373 mmol, 49.6%) was obtained as a white solid.
$^1$H-NMR (400 MHz, CDCl$_3$) δ: 1.44-2.05 (m, 5H), 2.23-2.31 (m, 1H), 3.37-3.47 (m, 1H), 3.67-3.74 (m, 1H), 4.86 (d, J=16.6 Hz, 1H), 4.91 (d, J=16.6 Hz, 1H), 5.16-5.22 (m, 1H), 6.97 (s, 1H), 7.13 (s, 1H), 7.20 (d, J=8.3 Hz, 1H), 7.29-7.37 (m, 4H), 7.40-7.45 (m, 1H), 7.53 (s, 1H), 7.70-7.87 (m, 1H), 8.41 (br, 1H).

ESI-MS: m/z=507 (M+H).

Example 53 Synthesis of 1-(2-(1H-tetrazol-1-yl)acetyl)-N-(2-chloro-2'-(trifluoromethoxy)-[1,1'-biphenyl]-4-yl)piperidine-2-carboxamide

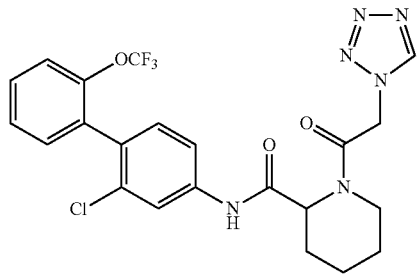

According to the same procedure as in Example 4, except that 1H-tetrazole-1-acetic acid was used in place of 2-methoxyacetic acid, 1-(2-(1H-tetrazol-1-yl)acetyl)-N-(2-chloro-2'-(trifluoromethoxy)-[1,1'-biphenyl]-4-yl)piperidine-2-carboxamide (hereinafter referred to as the compound of Example 53) (0.0244 g, 0.0479 mmol, 38.2%) was obtained as a white solid.

$^1$H-NMR (400 MHz, CDCl$_3$) δ: 1.59-2.02 (m, 5H), 2.29-2.32 (m, 1H), 3.49-3.57 (m, 1H), 3.73-3.77 (m, 1H), 5.18-5.19 (m, 1H), 5.40 (d, J=16.8 Hz, 1H), 5.48 (d, J=16.8 Hz, 1H), 7.21-7.46 (m, 6H), 7.81 (br, 1H), 8.02 (s, 1H), 8.86 (s, 1H).

ESI-MS: m/z=509 (M+H)$^+$.

Example 54 Synthesis of 1-(2-(furan-2-yl)acetyl)-N-(2-chloro-2'-(trifluoromethoxy)-[1,1'-biphenyl]-4-yl)piperidine-2-carboxamide

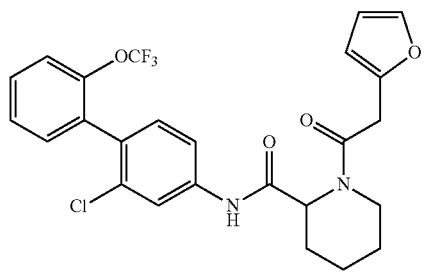 [SMILES: O=C(Nc1ccc(-c2ccccc2OC(F)(F)F)c(Cl)c1)C1CCCCN1C(=O)Cc1ccco1]

According to the same procedure as in Example 4, except that 2-furaneacetic acid was used in place of 2-methoxyacetic acid, 1-(2-(furan-2-yl)acetyl)-N-(2-chloro-2'-(trifluoromethoxy)-[1,1'-biphenyl]-4-yl)piperidine-2-carboxamide (hereinafter referred to as the compound of Example 54) (0.0605 g, 0.119 mmol, 95.2%) was obtained as a white amorphus.

$^1$H-NMR (400 MHz, CDCl$_3$) δ: 1.41-1.95 (m, 5H), 2.33-2.38 (m, 1H), 3.08-3.16 (m, 1H), 3.85-3.97 (m, 3H), 5.34-5.36 (m, 1H), 6.22-6.23 (m, 1H), 6.35-6.37 (m, 1H), 7.19-7.44 (m, 8H), 8.33 (br, 1H).

ESI-MS: m/z=505 (M–H)$^-$.

Example 55 Synthesis of 1-(2-(3,5-dimethyl-1H-pyrazol-1-yl)acetyl)-N-(2-chloro-2'-(trifluoromethoxy)-[1,1'-biphenyl]-4-yl)piperidine-2-carboxamide

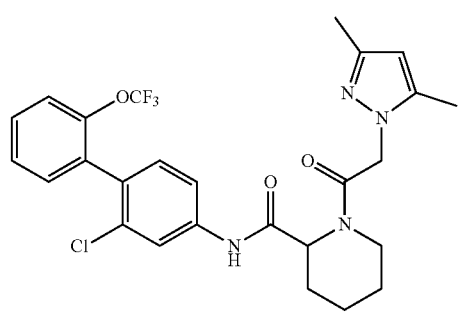 [SMILES: Cc1cc(C)n(CC(=O)N2CCCCC2C(=O)Nc2ccc(-c3ccccc3OC(F)(F)F)c(Cl)c2)n1]

According to the same procedure as in Example 4, except that 3,5-dimethyl-1H-pyrazole-1-acetic acid was used in place of 2-methoxyacetic acid, 1-(2-(3,5-dimethyl-1H-pyrazol-1-yl)acetyl)-N-(2-chloro-2'-(trifluoromethoxy)-[1,1'-biphenyl]-4-yl)piperidine-2-carboxamide (hereinafter referred to as the compound of Example 55) (0.0579 g, 0.108 mmol, 86.3%) was obtained as a white amorphus.

$^1$H-NMR (400 MHz, CDCl$_3$) δ: 1.46-1.66 (m, 2H), 1.74-1.79 (m, 3H), 2.08 (s, 3H), 2.27 (s, 3H), 2.47-2.50 (m, 1H), 3.11-3.19 (m, 1H), 3.69-3.74 (m, 1H), 4.83 (d, J=15.2 Hz, 1H), 4.96 (d, J=15.2 Hz, 1H), 5.35-5.36 (m, 1H), 5.89 (s, 1H), 7.21-7.45 (m, 7H), 8.86 (br, 1H).

ESI-MS: m/z=535 (M+H)$^+$.

Example 56 Synthesis of 1-(2-(3-methylisoxazol-5-yl)acetyl)-N-(2-chloro-2'-(trifluoromethoxy)-[1,1'-biphenyl]-4-yl)piperidine-2-carboxamide

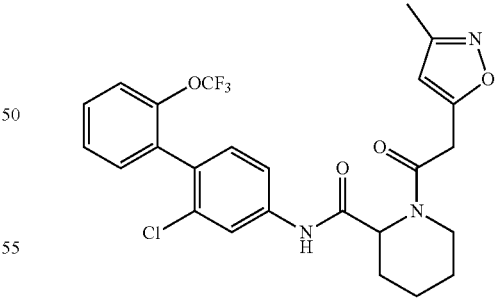

According to the same procedure as in Example 4, except that 3-methyl-5-isoxazoleacetic acid was used in place of 2-methoxyacetic acid, 1-(2-(3-methylisoxazol-5-yl)acetyl)-N-(2-chloro-2'-(trifluoromethoxy)-[1,1'-biphenyl]-4-yl)piperidine-2-carboxamide (hereinafter referred to as the compound of Example 56) (0.0652 g, 0.125 mmol, 99.6%) was obtained as a white amorphus.

$^1$H-NMR (400 MHz, CDCl$_3$): 1.47-1.96 (m, 5H), 2.29 (s, 3H), 2.33-2.39 (m, 1H), 3.21-3.28 (m, 1H), 3.82-3.87 (m,

1H), 3.95 (d, J=16.1 Hz, 1H), 4.01 (d, J=16.1 Hz, 1H), 5.32-5.33 (m, 1H), 6.08 (s, 1H), 7.21-7.45 (m, 7H), 8.27 (br, 1H).

ESI-MS: m/z=520 (M–H)⁻.

Example 57 Synthesis of (R)-1-(2-(1H-tetrazol-1-yl)acetyl)-N-(2-chloro-2'-(trifluoromethoxy)-[1,1'-biphenyl]-4-yl)piperidine-2-carboxamide

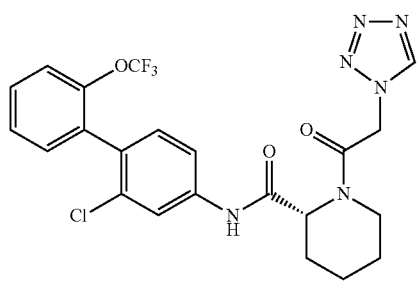

To a DMF (30 mL) solution of 1H-tetrazole-1-acetic acid (1.67 g, 13.04 mmol), a DMF (10 mL) solution of the compound of Reference Example 8 (4.00 g, 10.03 mmol), HATU (4.96 g, 13.04 mmol), and diisopropylethylamine (2.63 mL, 15.04 mmol) were added at room temperature, followed by stirring at the same temperature for 17 hours. To the reaction solution, distilled water was added, and the solution was extracted with toluene. The organic layer was concentrated under reduced pressure and the residue was purified by column chromatography (amine silica gel, n-hexane/ethyl acetate=40/60 to 0/100) to obtain (R)-1-(2-(1H-tetrazol-1-yl)acetyl)-N-(2-chloro-2'-(trifluoromethoxy)-[1,1'-biphenyl]-4-yl)piperidine-2-carboxamide (hereinafter referred to as the compound of Example 57) (3.87 g, 7.60 mmol, 75.9%) as a white amorphus. As a result of analysis using a chiral column, the retention time of the thus obtained compound of Example 57 was 55.3 minutes, and the optical purity at that time was 99.4% ee. The analysis conditions using the chiral column are as follows.

Measurement equipment; High-performance liquid chromatograph LC-2010CHT, manufactured by Shimadzu Corporation Column; CHIRALCEL OD-RH 0.46 cmφ×15 cm, particle size of 5 μm, manufactured by Daicel Chemical Industries Ltd.

Column temperature; 40° C.

Mobile phase; (Solution A) Distilled water, (Solution B) acetonitrile

Composition of mobile phase; Solution A:Solution B=60:40 (0 to 75 minutes)

Flow rate; 0.5 mL/minute

Detection; UV (210 nm)

¹H-NMR (400 MHz, CDCl₃) δ: 1.62-2.00 (m, 5H), 2.27-2.31 (m, 1H), 3.52-3.58 (m, 1H), 3.73-3.76 (m, 1H), 5.18-5.19 (m, 1H), 5.40 (d, J=16.5 Hz, 1H), 5.48 (d, J=16.5 Hz, 1H), 7.21-7.45 (m, 6H), 7.81 (br, 1H), 8.15 (s, 1H), 8.86 (s, 1H).

ESI-MS: m/z=509 (M+H)⁺.

Example 58 Synthesis of (R)-1-(3-(1H-tetrazol-1-yl)propanoyl)-N-(2-chloro-2'-(trifluoromethoxy)-[1,1'-biphenyl]-4-yl)piperidine-2-carboxamide

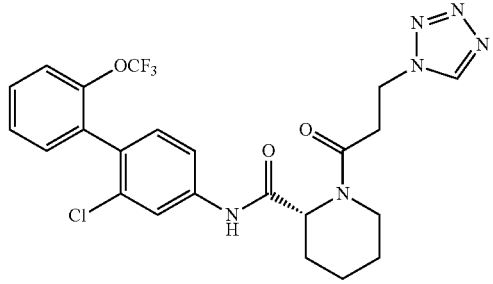 [SMILES: O=C(Nc1ccc(-c2ccccc2OC(F)(F)F)c(Cl)c1)[C@H]1CCCCN1C(=O)CCn1cnnn1]

According to the same procedure as in Example 4, except that 3-(tetrazol-1-yl)propionic acid was used in place of 2-methoxyacetic acid and the compound of Reference Example 8 was used in place of the compound of Reference Example 3, (R)-1-(3-(1H-tetrazol-1-yl)propanoyl)-N-(2-chloro-2'-(trifluoromethoxy)-[1,1'-biphenyl]-4-yl)piperidine-2-carboxamide (hereinafter referred to as the compound of Example 58) (0.117 g, 0.224 mmol, 89.1%) was obtained as a white amorphus.

¹H-NMR (400 MHz, CDCl₃) δ: 1.43-1.97 (m, 5H), 2.25-2.29 (m, 1H), 3.04-3.19 (m, 2H), 3.25 (td, J=13.0, 2.7 Hz, 1H), 3.70-3.74 (m, 1H), 4.79-4.92 (m, 2H), 5.18-5.19 (m, 1H), 7.22-7.44 (m, 6H), 7.79 (br, 1H), 8.13 (br, 1H), 8.84 (s, 1H).

ESI-MS: m/z=521 (M–H)⁻.

Example 59 Synthesis of (R)-1-(3-(1H-imidazol-1-yl)propanoyl)-N-(2-chloro-2'-(trifluoromethoxy)-[1,1'-biphenyl]-4-yl)piperidine-2-carboxamide

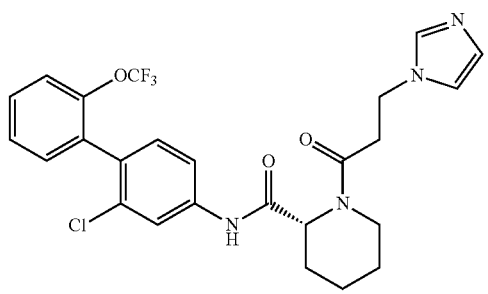 [SMILES: O=C(Nc1ccc(-c2ccccc2OC(F)(F)F)c(Cl)c1)[C@H]1CCCCN1C(=O)CCn1ccnc1]

According to the same procedure as in Example 4, except that 3-(imidazol-1-yl)propionic acid was used in place of 2-methoxyacetic acid and the compound of Reference Example 8 was used in place of the compound of Reference Example 3, (R)-1-(3-(1H-imidazol-1-yl)propanoyl)-N-(2-chloro-2'-(trifluoromethoxy)-[1,1'-biphenyl]-4-yl)piperidine-2-carboxamide (hereinafter referred to as the compound of Example 59) (0.0796 g, 0.153 mmol, 60.9%) was obtained as a white amorphus.

¹H-NMR (400 MHz, CDCl₃) δ: 1.37-1.99 (m, 5H), 2.26-2.29 (m, 1H), 2.87-2.91 (m, 2H), 3.17 (td, J=13.3, 2.7 Hz, 1H), 3.67-3.71 (m, 1H), 4.34-4.47 (m, 2H), 5.24-5.25 (m,

1H), 6.99 (s, 1H), 7.06 (s, 1H), 7.21-7.45 (m, 6H), 7.58 (br, 1H), 7.71-7.82 (m, 1H), 8.33 (br, 1H).

ESI-MS: m/z=521 (M+H)⁺.

Example 60 Synthesis of (R)-1-(3-(3-methyl-1H-pyrazol-1-yl)propanoyl)-N-(2-chloro-2'-(trifluoromethoxy)-[1,1'-biphenyl]-4-yl)piperidine-2-carboxamide

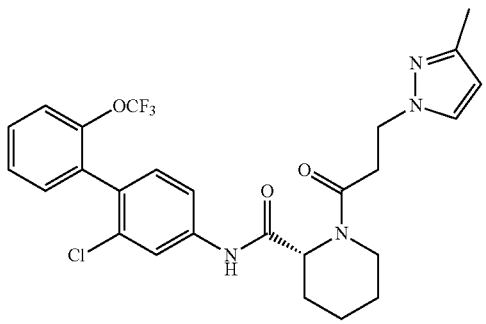 [SMILES: Cc1ccn(CCC(=O)N2CCCC[C@@H]2C(=O)Nc2ccc(-c3ccccc3OC(F)(F)F)c(Cl)c2)n1]

According to the same procedure as in Example 4, except that 3-(3-methyl-pyrazol-1-yl)propionic acid was used in place of 2-methoxyacetic acid and the compound of Reference Example 8 was used in place of the compound of Reference Example 3, (R)-1-(3-(3-methyl-1H-pyrazol-1-yl)propanoyl)-N-(2-chloro-2'-(trifluoromethoxy)-[1,1'-biphenyl]-4-yl)piperidine-2-carboxamide (hereinafter referred to as the compound of Example 60) (0.135 g, 0.252 mmol, quantitative) was obtained as a white amorphus.

¹H-NMR (400 MHz, CDCl₃) δ: 1.37-1.89 (m, 5H), 2.12 (s, 3H), 2.35-2.38 (m, 1H), 2.85-3.12 (m, 3H), 3.67-3.70 (m, 1H), 4.38-4.44 (m, 1H), 4.51-4.58 (m, 1H), 5.30-5.32 (m, 1H), 5.96-5.97 (m, 1H), 7.19-7.45 (m, 8H), 8.59 (br, 1H).

ESI-MS: m/z=535 (M+H)⁺.

Example 61 Synthesis of (R)-1-(2-(1H-pyrazol-1-yl)acetyl)-N-(2-chloro-2'-(trifluoromethoxy)-[1,1'-biphenyl]-4-yl)piperidine-2-carboxamide

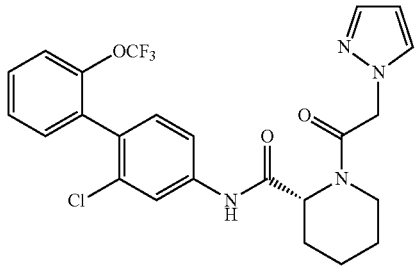 [SMILES: O=C(Nc1ccc(-c2ccccc2OC(F)(F)F)c(Cl)c1)[C@H]1CCCCN1C(=O)Cn1cccn1]

According to the same procedure as in Example 4, except that 2-(1H-pyrazol-1-yl)acetic acid was used in place of 2-methoxyacetic acid and the compound of Reference Example 8 was used in place of the compound of Reference Example 3, (R)-1-(2-(1H-pyrazol-1-yl)acetyl)-N-(2-chloro-2'-(trifluoromethoxy)-[1,1'-biphenyl]-4-yl)piperidine-2-carboxamide (hereinafter referred to as the compound of Example 61) (0.0623 g, 0.123 mmol, 98.0%) was obtained as a white solid.

¹H-NMR (400 MHz, CDCl₃) δ: 1.46-1.74 (m, 5H), 2.52-2.55 (m, 1H), 3.04-3.12 (m, 1H), 3.65-3.69 (m, 1H), 5.01 (d, J=14.5 Hz, 1H), 5.22 (d, J=14.5 Hz, 1H), 5.43-5.44 (m, 1H), 6.39 (dd, J=2.3, 2.0 Hz, 1H), 7.24 (d, J=8.2 Hz, 1H), 7.32-7.37 (m, 3H), 7.41-7.45 (m, 1H), 7.52-7.61 (m, 1H), 7.53 (d, J=2.3 Hz, 1H), 7.58 (d, J=2.0 Hz, 1H), 7.80-7.87 (brm, 1H), 9.02 (s, 1H).

ESI-MS: m/z=507 (M+H)⁺.

Example 62 Synthesis of (R)-1-(2-(4H-1,2,4-triazol-4-yl)acetyl)-N-(2-chloro-2'-(trifluoromethoxy)-[1,1'-biphenyl]-4-yl)piperidine-2-carboxamide

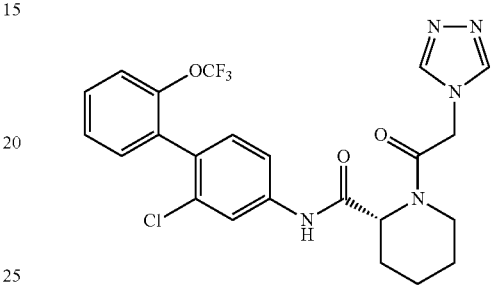

According to the same procedure as in Example 4, except that 2-(4H-1,2,4-triazol-4-yl)acetic acid was used in place of 2-methoxyacetic acid and the compound of Reference Example 8 was used in place of the compound of Reference Example 3, (R)-1-(2-(4H-1,2,4-triazol-4-yl)acetyl)-N-(2-chloro-2'-(trifluoromethoxy)-[1,1'-biphenyl]-4-yl)piperidine-2-carboxamide (hereinafter referred to as the compound of Example 62) (0.0575 g, 0.113 mmol, 90.3%) was obtained as a white solid.

¹H-NMR (400 MHz, CDCl₃) δ: 1.55-1.90 (m, 5H), 2.29-2.32 (m, 1H), 3.57-3.71 (m, 2H), 4.93 (d, J=16.8 Hz, 1H), 5.02 (d, J=16.8 Hz, 1H), 5.22-5.23 (m, 1H), 7.19 (d, J=8.2 Hz, 1H), 7.28-7.37 (m, 4H), 7.40-7.45 (m, 1H), 7.81 (s, 1H), 8.21 (s, 2H), 8.84 (s, 1H).

ESI-MS: m/z=508 (M+H)⁺.

Example 63 Synthesis of (R)-1-(2-(1H-1,2,4-triazol-1-yl)acetyl)-N-(2-chloro-2'-(trifluoromethoxy)-[1,1'-biphenyl]-4-yl)piperidine-2-carboxamide

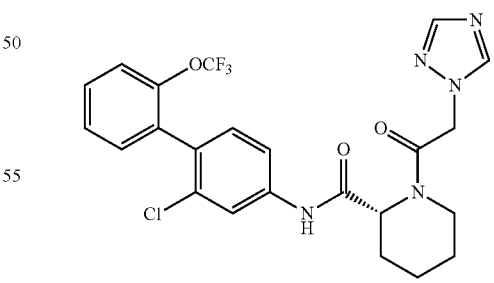

According to the same procedure as in Example 4, except that sodium 2-(1H-1,2,4-triazol-1-yl)acetate was used in place of 2-methoxyacetic acid and the compound of Reference Example 8 was used in place of the compound of Reference Example 3, (R)-1-(2-(1H-1,2,4-triazol-1-yl)acetyl)-N-(2-chloro-2'-(trifluoromethoxy)-[1,1'-biphenyl]-4-yl)piperidine-2-carboxamide (hereinafter referred to as the compound of Example 63) (0.0587 g, 0.116 mmol, 92.2%) was obtained as a white solid.

¹H-NMR (400 MHz, CDCl₃) δ: 1.54-1.70 (m, 2H), 1.77-1.90 (m, 3H), 2.38-2.41 (m, 1H), 3.31-3.39 (m, 1H), 3.74-3.78 (m, 1H), 5.13 (d, J=15.4 Hz, 1H), 5.22 (d, J=15.4 Hz, 1H), 5.29 (d, J=5.0 Hz, 1H), 7.23 (d, J=8.2 Hz, 1H), 7.30-7.37 (m, 4H), 7.41-7.45 (m, 1H), 7.79 (brs, 1H), 8.02 (s, 1H), 8.26 (s, 1H), 8.39 (s, 1H).

ESI-MS: m/z=508 (M+H).

Example 64 Synthesis of (R)-1-(2-(1H-1,2,3-triazol-1-yl)acetyl)-N-(2-chloro-2'-(trifluoromethoxy)-[1,1'-biphenyl]-4-yl)piperidine-2-carboxamide

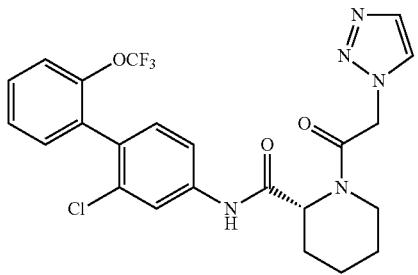 [SMILES: O=C(Nc1ccc(-c2ccccc2OC(F)(F)F)c(Cl)c1)[C@H]1CCCCN1C(=O)Cn1ccnn1]

According to the same procedure as in Example 4, except that 2-(1H-1,2,3-triazol-1-yl)acetic acid was used in place of 2-methoxyacetic acid and the compound of Reference Example 8 was used in place of the compound of Reference Example 3, (R)-1-(2-(1H-1,2,3-triazol-1-yl)acetyl)-N-(2-chloro-2'-(trifluoromethoxy)-[1,1'-biphenyl]-4-yl)piperidine-2-carboxamide (hereinafter referred to as the compound of Example 64) (0.0619 g, 0.122 mmol, 97.2%) was obtained as a white solid.

¹H-NMR (400 MHz, CDCl₃) δ: 1.51-1.70 (m, 2H), 1.76-1.88 (m, 3H), 2.39-2.42 (m, 1H), 3.32-3.39 (m, 1H), 3.74-3.78 (m, 1H), 5.30-5.31 (m, 1H), 5.34 (d, J=15.4 Hz, 1H), 5.41 (d, J=15.4 Hz, 1H), 7.23 (d, J=8.6 Hz, 1H), 7.30-7.37 (m, 3H), 7.41-7.45 (m, 1H), 7.52 (brs, 1H), 7.76 (d, J=0.9 Hz, 1H), 7.82 (d, J=0.9 Hz, 1H), 7.91 (brs, 1H), 8.43 (s, 1H).

ESI-MS: m/z=508 (M+H)⁺.

Example 65 Synthesis of (R)-1-(2-(1H-imidazol-1-yl)acetyl)-N-(2-chloro-2'-(trifluoromethoxy)-[1,1'-biphenyl]-4-yl)piperidine-2-carboxamide

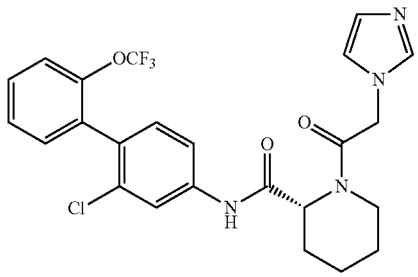 [SMILES: O=C(Nc1ccc(-c2ccccc2OC(F)(F)F)c(Cl)c1)[C@H]1CCCCN1C(=O)Cn1ccnc1]

According to the same procedure as in Example 4, except that 1-imidazoleacetic acid was used in place of 2-methoxyacetic acid and the compound of Reference Example 8 was used in place of the compound of Reference Example 3, (R)-1-(2-(1H-imidazol-1-yl)acetyl)-N-(2-chloro-2'-(trifluoromethoxy)-[1,1'-biphenyl]-4-yl)piperidine-2-carboxamide (hereinafter referred to as the compound of Example 65) (0.635 g, 1.25 mmol, 63.5%) was obtained as a white amorphus.

¹H-NMR (400 MHz, CDCl₃) δ: 1.44-2.05 (m, 5H), 2.23-2.31 (m, 1H), 3.37-3.47 (m, 1H), 3.67-3.74 (m, 1H), 4.86 (d, J=16.6 Hz, 1H), 4.91 (d, J=16.6 Hz, 1H), 5.16-5.22 (m, 1H), 6.97 (s, 1H), 7.13 (s, 1H), 7.20 (d, J=8.3 Hz, 1H), 7.29-7.37 (m, 4H), 7.40-7.45 (m, 1H), 7.53 (s, 1H), 7.70-7.87 (m, 1H), 8.41 (brs, 1H).

ESI-MS: m/z=507 (M+H)*.

Example 66 Synthesis of (R)-1-(2-(2H-1,2,3-triazol-2-yl)acetyl)-N-(2-chloro-2'-(trifluoromethoxy)-[1,1'-biphenyl]-4-yl)piperidine-2-carboxamide

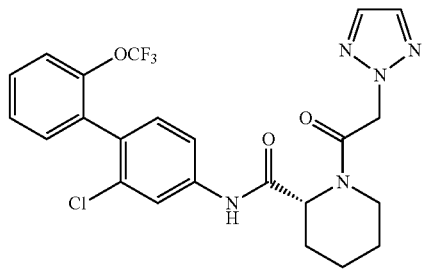 [SMILES: O=C(Nc1ccc(-c2ccccc2OC(F)(F)F)c(Cl)c1)[C@H]1CCCCN1C(=O)Cn1nccn1]

According to the same procedure as in Example 4, except that 2-(2H-1,2,3-triazol-2-yl)acetic acid was used in place of 2-methoxyacetic acid and the compound of Reference Example 8 was used in place of the compound of Reference Example 3, (R)-1-(2-(2H-1,2,3-triazol-2-yl)acetyl)-N-(2-chloro-2'-(trifluoromethoxy)-[1,1'-biphenyl]-4-yl)piperidine-2-carboxamide (hereinafter referred to as the compound of Example 66) (0.0321 g, 0.0632 mmol, 50.4%) was obtained as a white amorphus.

¹H-NMR (400 MHz, CDCl₃) δ: 1.47-1.65 (m, 2H), 1.68-1.77 (m, 3H), 2.49-2.52 (m, 1H), 2.98-3.06 (m, 1H), 3.55-3.58 (m, 1H), 5.33 (d, J=15.0 Hz, 1H), 5.42 (d, J=5.0 Hz, 1H), 5.57 (d, J=15.0 Hz, 1H), 7.24 (d, J=8.2 Hz, 1H), 7.32-7.37 (m, 3H), 7.41-7.46 (m, 1H), 7.42-7.88 (brm, 2H), 7.73 (s, 2H), 8.63 (s, 1H).

ESI-MS: m/z=530 (M+Na)⁺.

Reference Example 30 Synthesis of ethyl 2-(5-methyl-1,3,4-oxadiazol-2-yl)acetate

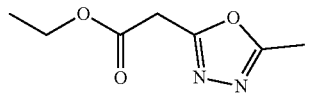

To a dichloroethane (6.4 mL) solution of ethyl 2-(1H-tetrazol-5-yl)acetate (0.500 g, 3.20 mmol), acetic anhydride (0.393 mL, 4.16 mmol) was added at room temperature and the temperature was raised to 100° C., followed by stirring for 11 hours. To the reaction solution, an aqueous 1M sodium hydroxide solution was added, and the solution was extracted with ethyl acetate. The organic layer was washed with an aqueous 1M sodium hydroxide solution and saturated brine, dried over anhydrous sodium sulfate and filtered, and then the filtrate was concentrated under reduced pressure. The residue was purified by column chromatography (silica gel, n-hexane/ethyl acetate=70/30 to 40/60) to obtain ethyl 2-(5-methyl-1,3,4-oxadiazol-2-yl)acetate (hereinafter referred to as the compound of Reference Example 30) (0.0908 g, 0.534 mmol, 16.7%) as a colorless oily product.

$^1$H-NMR (400 MHz, CDCl$_3$) δ: 1.29 (t, J=7.2 Hz, 3H), 2.55 (s, 3H), 3.92 (s, 2H), 4.23 (q, J=7.2 Hz, 2H).

ESI-MS: m/z=171 (M+H)$^+$.

Reference Example 31 Synthesis of sodium 2-(5-methyl-1,3,4-oxadiazol-2-yl)acetate

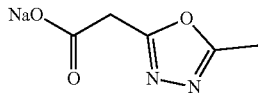

To a tetrahydrofuran (1.0 mL) solution of the compound of Reference Example 30 (0.0900 g, 0.529 mmol), an aqueous 1M sodium hydroxide solution (1.06 mL, 1.06 mmol) and ethanol (1.0 mL) were added at room temperature, followed by stirring at the same temperature for 2 hours. The reaction solution was concentrated under reduced pressure to obtain crude sodium 2-(5-methyl-1,3,4-oxadiazol-2-yl)acetate (hereinafter referred to as the compound of Reference Example 31) (0.0835 g) as a white solid. The compound of Reference Example 31 was directly used for the subsequent reaction.

$^1$H-NMR (400 MHz, DMSO-D$_6$) δ: 2.41 (s, 3H), 3.38 (s, 2H).

ESI-MS: m/z=143 (M+H)$^+$.

Example 67 Synthesis of (R)—N-(2-chloro-2'-(trifluoromethoxy)-[1,1'-biphenyl]-4-yl)-1-(2-(5-methyl-1,3,4-oxadiazol-2-yl)acetyl)piperidine-2-carboxamide

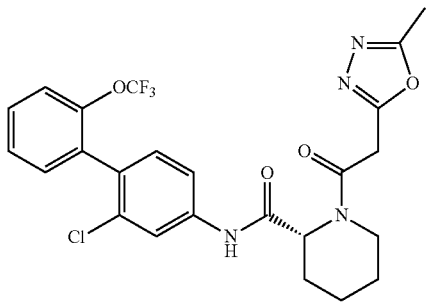 [SMILES: Cc1nnc(CC(=O)N2CCCC[C@@H]2C(=O)Nc2ccc(-c3ccccc3OC(F)(F)F)c(Cl)c2)o1]

According to the same procedure as in Example 4, except that the compound of Reference Example 31 was used in place of 2-methoxyacetic acid and the compound of Reference Example 8 was used in place of the compound of Reference Example 3, (R)—N-(2-chloro-2'-(trifluoromethoxy)-[1,1'-biphenyl]-4-yl)-1-(2-(5-methyl-1,3,4-oxadiazol-2-yl)acetyl)piperidine-2-carboxamide (hereinafter referred to as the compound of Example 67) (0.0524 g, 0.0910 mmol, 90.8%) was obtained as a white amorphus.

$^1$H-NMR (400 MHz, CDCl$_3$) δ: 1.50-1.66 (m, 3H), 1.74-1.77 (m, 2H), 2.57 (s, 3H), 2.62-2.65 (m, 1H), 3.27-3.34 (m, 1H), 3.61-3.64 (m, 1H), 3.94 (d, J=17.4 Hz, 1H), 4.21 (d, J=17.4 Hz, 1H), 5.54-5.55 (m, 1H), 7.25-7.27 (m, 1H), 7.33-7.36 (m, 3H), 7.40-7.44 (m, 1H), 7.77 (brs, 1H), 8.18 (brs, 1H), 9.38 (s, 1H).

ESI-MS: m/z=545 (M+Na)$^+$.

Example 68 Synthesis of (R)—N-(2-chloro-2'-(trifluoromethoxy)-[1,1'-biphenyl]-4-yl)-1-(3-(dimethylamino)propanoyl)piperidine-2-carboxamide

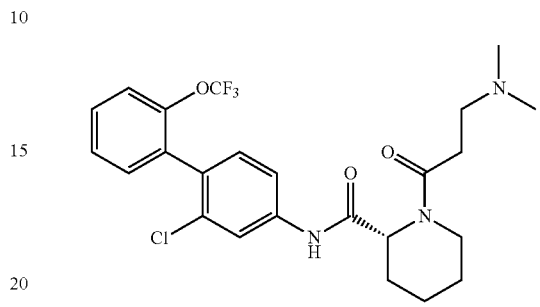

According to the same procedure as in Example 4, except that 3-(dimethylamino)propanoic acid hydrochloride was used in place of 2-methoxyacetic acid and the compound of Reference Example 8 was used in place of the compound of Reference Example 3, (R)—N-(2-chloro-2'-(trifluoromethoxy)-[1,1'-biphenyl]-4-yl)-1-(3-(dimethylamino)propanoyl)piperidine-2-carboxamide (hereinafter referred to as the compound of Example 68) (0.0826 g, 0.166 mmol, 66.2%) was obtained as a white amorphus.

$^1$H-NMR (400 MHz, CDCl$_3$) δ: 1.46-1.83 (m, 5H), 2.26 (s, 0.6H), 2.28 (s, 5.4H), 2.40-2.44 (m, 1H), 2.55-2.62 (m, 1H), 2.65-2.81 (m, 3H), 2.99-3.05 (m, 0.1H), 3.13-3.20 (m, 0.9H), 3.88-3.91 (m, 0.9H), 4.69 (d, J=5.0 Hz, 0.1H), 4.73-4.76 (m, 0.1H), 5.43 (d, J=5.0 Hz, 0.9H), 7.21 (d, J=8.6 Hz, 1H), 7.31-7.86 (m, 6H), 8.76 (br, 0.9H), 9.33 (br, 0.1H).

ESI-MS: m/z=498 (M+H)$^+$.

Example 69 Synthesis of methyl (R)-5-(2-((2-chloro-2'-(trifluoromethoxy)-[1,1'-biphenyl]-4-yl)carbamoyl)piperidin-1-yl)-5-oxopentanoate

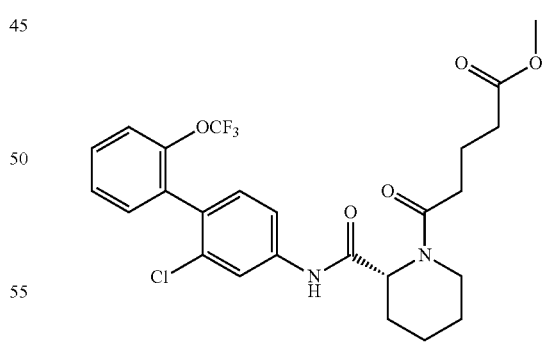

According to the same procedure as in Example 3, except that methyl 4-(chloroformyl)butyrate was used in place of propionyl chloride and the compound of Reference Example 8 was used in place of the compound of Reference Example 3, methyl (R)-5-(2-((2-chloro-2'-(trifluoromethoxy)-[1,1'-biphenyl]-4-yl)carbamoyl)piperidin-1-yl)-5-oxopentanoate (hereinafter referred to as the compound of Example 69) (0.130 g, 0.247 mmol, 98.4%) was obtained as a white amorphus.

$^1$H-NMR (400 MHz, CDCl$_3$) δ: 1.44-1.79 (m, 4H), 1.84-1.95 (m, 1H), 1.96-2.13 (m, 2H), 2.35 (d, J=13.7 Hz, 1H), 2.40-2.62 (m, 4H), 2.63-2.70 (m, 0.1H), 3.14-3.21 (m, 0.9H), 3.68 (s, 2.7H), 3.69 (s, 0.3H), 3.84-3.88 (m, 0.9H), 4.66-4.69 (m, 0.2H), 5.34 (d, J=5.0 Hz, 0.9H), 7.20 (d, J=8.2 Hz, 1H), 7.29-7.94 (m, 6H), 8.68 (s, 0.9H), 8.90 (s, 0.1H).

Example 70 Synthesis of (R)-5-(2-((2-chloro-2'-(trifluoromethoxy)-[1,1'-biphenyl]-4-yl)carbamoyl)piperidin-1-yl)-5-oxopentanoic acid

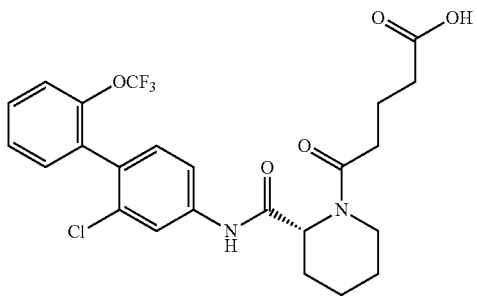 [SMILES: O=C(O)CCCC(=O)N1CCCC[C@@H]1C(=O)Nc1ccc(-c2ccccc2OC(F)(F)F)c(Cl)c1]

To a methanol (2.5 mL) solution of the compound of Example 69 (0.130 g, 0.247 mmol), an aqueous 1M sodium hydroxide solution (2.47 mL, 2.47 mmol) and tetrahydrofuran (2.5 mL) were added at 0° C. and the temperature was raised to room temperature, followed by stirring for 5 hours. To the reaction solution, 1M hydrochloric acid was added, and the solution was extracted with chloroform. The organic layer was washed with saturated brine, dried over anhydrous sodium sulfate and filtered, and then the filtrate was concentrated under reduced pressure. The residue was purified by column chromatography (silica gel, chloroform/methanol=98/2 to 90/10) to obtain (R)-5-(2-((2-chloro-2'-(trifluoromethoxy)-[1,1'-biphenyl]-4-yl)carbamoyl)piperidin-1-yl)-5-oxopentanoic acid (hereinafter referred to as the compound of Example 70) (0.0592 g, 0.115 mmol, 46.7%) as a white amorphus.

$^1$H-NMR (400 MHz, CDCl$_3$) δ: 1.49-1.79 (m, 4H), 1.84-1.94 (m, 1H), 2.00-2.10 (m, 2H), 2.32 (d, J=13.6 Hz, 1H), 2.44-2.63 (m, 4H), 3.20 (td, J=13.3, 2.6 Hz, 1H), 3.81-3.87 (m, 1H), 5.30 (d, J=4.5 Hz, 1H), 7.20 (d, J=8.6 Hz, 1H), 7.29-7.36 (m, 3H), 7.40-7.45 (m, 2H), 7.75-7.88 (m, 1H), 8.62 (s, 1H).

ESI-MS: m/z=535 (M+Na)$^+$.

Example 71 Inhibitory Effect on RORγ-Coactivator Binding

The inhibitory effect of cyclic amine derivative (I) or a pharmacologically acceptable salt thereof on the binding between a ligand-binding domain of RORγ (hereinafter referred to as RORγ-LBD) and a coactivator was evaluated using Invitrogen's LanthaScreen™ TR-FRET Retinoid-Related Orphan Receptor (ROR) gamma Coactivator Assay kit utilizing time-resolved fluorescence energy transfer (TR-FRET).

The test compound was dissolved in DMSO and diluted with TR-FRET Coregulator Buffer D (Invitrogen) containing 5 mmol/L of DTT to have a final DMSO concentration of 1% before use. To each well of a 384-well black plate (Corning Inc.), 4 nmol/L of GST-fused RORγ-LBD (Invitrogen) diluted with the buffer mentioned above and the test compound were added. A well without addition of the test compound and without addition of GST-fused RORγ-LBD (background) and a well without addition of the test compound and with addition of GST-fused RORγ-LBD (control) were prepared. Next, 150 nmol/L of fluorescein-labeled TRAP220/DRIP-2 (Invitrogen) diluted with the buffer mentioned above and 32 nmol/L of terbium-labeled anti-GST antibody (Invitrogen) were added to each well. After incubating the plate at room temperature for 16 to 24 hours, the fluorescence at 495 nm and 520 nm when excited at 320 nm was measured for each well and the ratio (fluorescence value at 520 nm/fluorescence value at 495 nm) was calculated.

The fold change with addition of the test compound (ratio with addition of the test compound/ratio of the background), the fold change of the control (ratio of the control/ratio of the background), and the fold change of the background (ratio of the background/ratio of the background) were calculated, and then the inhibition rate of binding between RORγ-LBD and a coactivator (hereinafter referred to as RORγ-coactivator binding inhibition rate) (%) was calculated from formula (1):

RORγ-coactivator binding inhibition rate (%)=(1−((Fold change with addition of the test compound)−(Fold change of the background))/((Fold change of the control)−(Fold change of the background)))×100  (1)

The RORγ-coactivator binding inhibition rate (%) at 33 μmol/L of the test compound is shown in Tables 2-1 and 2-2.

TABLE 2-1

| Test compound | RORγ-coactivator binding inhibition rate (%) |
|---|---|
| Compound of Example 1 | 90.9 |
| Compound of Example 2 | 91.9 |
| Compound of Example 3 | 88.2 |
| Compound of Example 4 | 90.3 |
| Compound of Example 5 | 96.9 |
| Compound of Example 8 | 95.2 |
| Compound of Example 10 | 100.1 |
| Compound of Example 13 | 101.4 |
| Compound of Example 14 | 94.0 |
| Compound of Example 15 | 100.1 |
| Compound of Example 16 | 99.3 |
| Compound of Example 17 | 93.8 |
| Compound of Example 18 | 95.9 |
| Compound of Example 19 | 93.4 |
| Compound of Example 20 | 100.7 |
| Compound of Example 21 | 98.2 |
| Compound of Example 22 | 92.4 |
| Compound of Example 23 | 98.4 |
| Compound of Example 25 | 94.2 |
| Compound of Example 28 | 100.9 |
| Compound of Example 29 | 101.3 |
| Compound of Example 32 | 94.7 |
| Compound of Example 36 | 97.2 |
| Compound of Example 37 | 103.5 |
| Compound of Example 39 | 98.8 |
| Compound of Example 40 | 98.7 |
| Compound of Example 42 | 92.8 |
| Compound of Example 43 | 99.0 |
| Compound of Example 44 | 97.1 |
| Compound of Example 45 | 92.0 |
| Compound of Example 46 | 99.3 |
| Compound of Example 47 | 98.8 |
| Compound of Example 48 | 101.6 |
| Compound of Example 49 | 99.3 |
| Compound of Example 50 | 101.1 |
| Compound of Example 51 | 100.4 |
| Compound of Example 52 | 97.3 |
| Compound of Example 53 | 104.7 |
| Compound of Example 54 | 101.5 |
| Compound of Example 55 | 103.5 |
| Compound of Example 56 | 103.5 |

TABLE 2-1-continued

| Test compound | RORγ-coactivator binding inhibition rate (%) |
|---|---|
| Compound of Example 57 | 103.0 |
| Compound of Example 58 | 100.5 |

TABLE 2-2

| Test compound | RORγ-coactivator binding inhibition rate (%) |
|---|---|
| Compound of Example 59 | 95.5 |
| Compound of Example 60 | 93.6 |
| Compound of Example 61 | 101.9 |
| Compound of Example 64 | 97.3 |
| Compound of Example 65 | 91.7 |
| Compound of Example 66 | 103.2 |
| Compound of Example 67 | 99.1 |
| Compound of Example 69 | 95.9 |

These results revealed that cyclic amine derivative (I) or a pharmacologically acceptable salt thereof markedly inhibits the binding between RORγ-LBD and a coactivator.

Example 72 Suppressive Effect on IL-17 Production in Mouse Splenocytes:

Using mouse splenocytes, the suppressive effect of cyclic amine derivative (I) or a pharmacologically acceptable salt thereof on IL-17 production by IL-23 stimulation was evaluated by a partially modified method mentioned in The Journal of Biological Chemistry, 2003, Vol. 278, No. 3, p. 1910-1914.

A single cell suspension was prepared from the spleen of C57BL/6J mice (male, 7 to 23 weeks old) (Charles River Laboratories Japan, Inc.) and splenocytes were prepared using Histopaque-1083 (Sigma-Aldrich Japan). The culture medium was used by adding 10% FBS (Gibco), 50 U/mL of penicillin-50 μg/mL of streptomycin (Gibco), 50 μmol/L of 2-mercaptoethanol (Gibco), and 100 U/mL of human IL-2 (Cell Science & Technology Institute, Inc.) to RPMI1640 medium (Gibco). The test compound was dissolved in DMSO and then diluted with the culture medium to have a final concentration of DMSO of 0.1% before use. Splenocytes ($3 \times 10^5$ cells/well) prepared in the culture medium were seeded in wells of a 96-well flat-bottom plate (Corning Incorporated), the test compound and 10 ng/mL of human IL-23 (R & D systems, Inc.) were added thereto, and the cells were cultured at 37° C. under 5% $CO_2$ for 3 days. A well without addition of human IL-23 and without addition of the test compound and a well with addition of human IL-23 and without addition of the test compound were prepared. After completion of the culture, the culture supernatant was collected and the IL-17 production amount in the supernatant was determined by ELISA method (R & D systems, Inc.).

The IL-17 production inhibition rate (%) was calculated from Formula (2).

IL-17 production inhibition rate (%)=(1−((IL-17 production amount with addition of IL-23 and with addition of the test compound)−(IL-17 production amount without addition of IL-23 and without addition of the test compound))/((IL-17 production amount with addition of IL-23 and without addition of the test compound)−(IL-17 production amount without addition of IL-23 and without addition of the test compound)))× 100     (2)

The IL-17 production inhibition rate (%) at 5 μmol/L of the test compound is shown in Tables 3-1 and 3-2.

TABLE 3-1

| Test compound | IL-17 production inhibition rate (%) |
|---|---|
| Compound of Example 1 | 94.0 |
| Compound of Example 2 | 96.2 |
| Compound of Example 3 | 98.6 |
| Compound of Example 4 | 99.7 |
| Compound of Example 5 | 99.5 |
| Compound of Example 6 | 91.6 |
| Compound of Example 7 | 99.0 |
| Compound of Example 8 | 99.2 |
| Compound of Example 9 | 94.6 |
| Compound of Example 10 | 98.6 |
| Compound of Example 11 | 94.1 |
| Compound of Example 12 | 96.1 |
| Compound of Example 13 | 98.2 |
| Compound of Example 14 | 90.5 |
| Compound of Example 15 | 99.4 |
| Compound of Example 16 | 98.0 |
| Compound of Example 17 | 91.8 |
| Compound of Example 18 | 90.8 |
| Compound of Example 19 | 99.8 |
| Compound of Example 20 | 99.7 |
| Compound of Example 21 | 99.8 |
| Compound of Example 22 | 98.1 |
| Compound of Example 23 | 99.4 |
| Compound of Example 24 | 95.7 |
| Compound of Example 25 | 99.4 |
| Compound of Example 26 | 96.4 |
| Compound of Example 27 | 97.4 |
| Compound of Example 28 | 98.6 |
| Compound of Example 29 | 100.1 |
| Compound of Example 30 | 99.8 |
| Compound of Example 31 | 99.1 |
| Compound of Example 32 | 98.8 |
| Compound of Example 33 | 98.3 |
| Compound of Example 34 | 100.3 |
| Compound of Example 35 | 94.9 |
| Compound of Example 36 | 96.9 |
| Compound of Example 37 | 99.1 |
| Compound of Example 38 | 99.0 |
| Compound of Example 39 | 99.2 |
| Compound of Example 40 | 98.2 |
| Compound of Example 41 | 99.1 |
| Compound of Example 42 | 99.8 |
| Compound of Example 43 | 92.4 |

TABLE 3-2

| Test compound | IL-17 production inhibition rate (%) |
|---|---|
| Compound of Example 44 | 91.5 |
| Compound of Example 45 | 99.9 |
| Compound of Example 46 | 99.2 |
| Compound of Example 47 | 96.3 |
| Compound of Example 48 | 99.4 |
| Compound of Example 49 | 98.3 |
| Compound of Example 50 | 94.5 |
| Compound of Example 51 | 98.6 |
| Compound of Example 52 | 99.3 |
| Compound of Example 53 | 101.6 |
| Compound of Example 54 | 98.7 |
| Compound of Example 55 | 99.7 |
| Compound of Example 56 | 107.4 |
| Compound of Example 57 | 101.2 |
| Compound of Example 58 | 99.7 |
| Compound of Example 59 | 99.8 |
| Compound of Example 60 | 99.7 |
| Compound of Example 61 | 98.8 |
| Compound of Example 62 | 100.2 |
| Compound of Example 63 | 99.9 |
| Compound of Example 64 | 99.4 |
| Compound of Example 65 | 99.6 |
| Compound of Example 66 | 99.5 |
| Compound of Example 67 | 98.7 |

TABLE 3-2-continued

| Test compound | IL-17 production inhibition rate (%) |
| --- | --- |
| Compound of Example 68 | 99.4 |
| Compound of Example 69 | 99.5 |
| Compound of Example 70 | 99.7 |

These results revealed that cyclic amine derivative (I) or a pharmacologically acceptable salt thereof suppresses IL-17 production.

Example 73 Symptom-Suppressing Effect on a Mouse Alopecia Areata Model (Preventive Protocol)

The effect of cyclic amine derivative (I) or a pharmacologically acceptable salt thereof in a mouse alopecia areata model was evaluated using increase in the hair loss score as an index of worsening of symptoms. The mouse alopecia areata model was prepared by partially modifying the method by Wang et al. (Journal of Investigative Dermatology, 2015, Vol. 135, p. 2530-2532).

Female C3H/HeJ mice (CLEA Japan, Inc.) with spontaneous hair loss in 70% or more of the body surface were used as donor mice. The donor mice were euthanized by cervical dislocation, and then the inguinal, axilla, and auricular lymph nodes were aseptically removed. The lymph nodes were filtered through a 70 μm cell strainer to isolate lymphocytes. The lymphocytes were washed with Advanced RPMI media (containing 10% fetal bovine serum, 2 mM Gluta Max, and 100 U/mL penicillin streptomycin), and then suspended in Advanced RPMI media to which Human rIL-2 (Roche; final concentration of 30 U/mL), Mouse rIL-7 (R&D systems, Inc.; final concentration of 25 ng/mL), and Mouse rIL-15 (R&D systems, Inc.; final concentration of 50 ng/mL) were added so that the concentration was $2 \times 10^6$ cells/mL. The lymphocytes were seeded in 1 mL portions on 24-well plates, and 500 μL of Dynabead mouse T-activator CD3/CD28 (Life Technologies) was added, followed by culture in a $CO_2$ incubator. Culture was performed for 6 days so that the cell density was 1.5 to $2.0 \times 10^6$ cells/mL during culture.

The day of transplantation of lymphocytes derived from donor mice was regarded as Day 0. Two days before the day of transplantation (Day −2), hair on the back, which would be a transplantation site, of 10-week old female C3H/HeJ mice without hair loss (CLEA Japan, Inc.) was removed with an electric hair clipper under isoflurane anesthesia (1.5 cm×1.5 cm). Furthermore, grouping was performed using the body weight on Day −1 as an index.

On Day 0, lymphocytes in which beads were removed with EasySep magnet (Stemcell Technologies Inc.) were collected into new tubes. The collected lymphocytes were suspended in PBS(−) so that the concentration was $10 \times 10^7$ cells/mL, filled in a 1 mL syringe with a 26G injection needle, and stored on ice until transplantation. Under isoflurane anesthesia, the filled lymphocyte suspension was intradermally injected into the hair removal site in 100 μL/body portions. PBS(−) was intradermally administered in 100 μL/body portions to mice without transplantation of lymphocytes. Mice without transplantation of lymphocytes were regarded as the normal group. Mice with and without transplantation of lymphocytes were maintained on a low-fat diet (CR-LPF; Oriental Yeast Co., Ltd.) after Day 0.

Test compounds were administered to mice with lymphocyte transplantation at a dose of 10 mg/kg once daily for 63 days from Day 0 to Day 62. The compound of Example 29 and the compound of Example 57 were used as the test compounds. The compound of Example 29 and the compound of Example 57 were orally administered after suspended in a 0.5 w/v % methylcellulose solution. A group in which the compound of Example 29 was administered was regarded as the group of treatment with the compound of Example 29, and a group in which the compound of Example 57 was administered was regarded as the group of treatment with the compound of Example 57. A vehicle (0.5 w/v % methylcellulose solution) of each test compound was administered in the same manner to the normal group and the disease group (vehicle treatment group).

On Day 63, photographs of the back and the abdomen of the mice were taken under isoflurane anesthesia. The status of hair loss was evaluated by partially modifying the method by Alli et al. (Journal of Immunology, 2012, Vol. 188, p. 477-486). In other words, the ratio of the area of hair loss site to the body surface area was scored in accordance with the criteria mentioned in Table 4, and defined as the hair loss score. Specifically, the hair loss score was determined based on the numerical value of the ratio calculated from formula (3).

$$\text{Ratio of hair loss site (\%)} = (\text{area of hair loss site}/\text{body surface area}) \times 100 \quad (3)$$

TABLE 4

| Hair loss score | Ratio of hair loss site (%) (area of hair loss site/body surface area × 100) |
| --- | --- |
| 0 | ≤5 |
| 1 | >5 to ≤10 |
| 2 | >10 to ≤15 |
| 3 | >15 to ≤20 |
| 4 | >20 to ≤25 |
| 5 | >25 to ≤30 |
| 6 | >30 to ≤35 |
| 7 | >35 to ≤40 |
| 8 | >40 to ≤45 |
| 9 | >45 to ≤50 |
| 10 | >50% |

Figure 2:
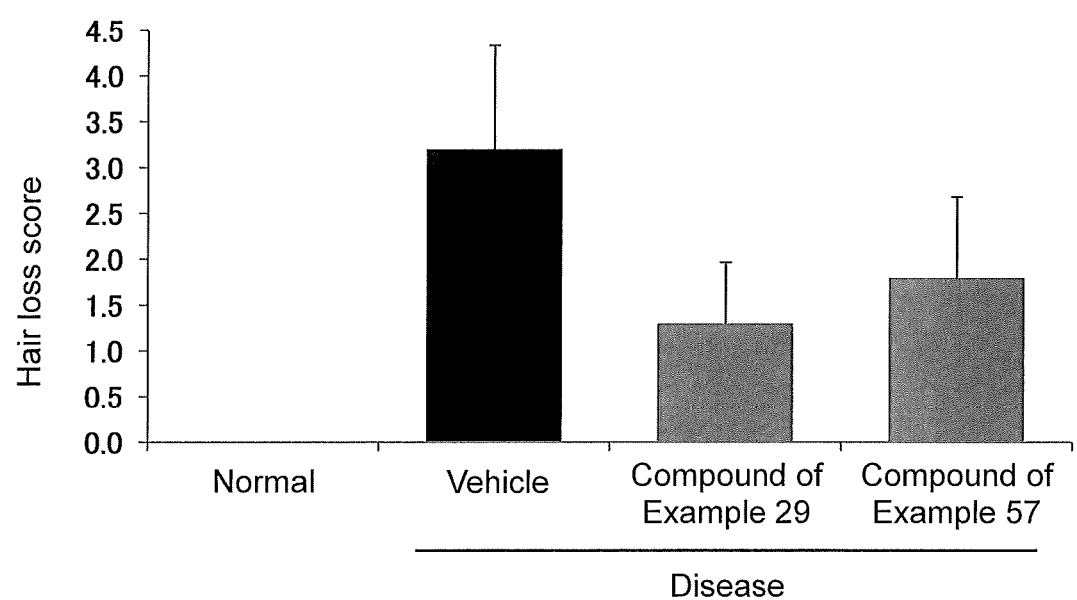
FIG. 2 is a graph showing the suppressing effects by the preventive protocol of the compound of Example 29 and the compound of Example 57 on increase in the hair loss score in a mouse alopecia areata model.

The results are shown in FIGS. 1 and 2. FIG. 1 is a photograph showing the abdomen of mice on Day 63, in which "normal" represents a typical example of the normal group, "vehicle" represents a typical example of the disease group (vehicle treatment group), "compound of Example 29" represents a typical example of the group of treatment with the compound of Example 29, and "compound of Example 57" represents a typical example of the group of treatment with the compound of Example 57. Transplantation of lymphocytes of donor mice resulted in a wider range of hair loss in the disease group (vehicle treatment group) compared with the normal group. Meanwhile, the range of hair loss was very smaller in the group of treatment with the compound of Example 29 and the group of treatment with the compound of Example 57 compared with the disease group (vehicle treatment group).

The vertical axis of FIG. 2 represents the hair loss score (mean±standard error) of each group. On the horizontal axis, "normal" represents the normal group (number of individuals: n=3), "vehicle" represents the disease group (vehicle treatment group) (n=10), "compound of Example 29" represents the group of treatment with the compound of Example 29 (n=10), and "compound of Example 57" represents the group of treatment with the compound of Example 57 (n=10). Transplantation of lymphocytes of donor mice resulted in remarkable increase in the hair loss score in the disease group (vehicle treatment group) compared with the normal group (hair loss score: 3.2±1.13). This increase in the hair loss score was suppressed by administration of the compound of Example 29 or the compound of Example 57 (the hair loss score of the group of treatment with the compound of Example 29: 1.3±0.67, the hair loss score of the group of treatment with the compound of Example 57: 1.8±0.88).

This result revealed that cyclic amine derivative (I) or a pharmacologically acceptable salt thereof exhibits a remarkable symptom-suppressing effect on hair loss symptoms by the preventive protocol.

Example 74 Symptom-Suppressing Effect on a Mouse Alopecia Areata Model (Therapeutic Protocol)

The effect of cyclic amine derivative (I) or a pharmacologically acceptable salt thereof in a mouse alopecia areata model was evaluated using increase in the hair loss score as an index of worsening of symptoms. The mouse alopecia areata model was prepared using the same method as in Example 73.

In other words, female C3H/HeJ mice (CLEA Japan, Inc.) with spontaneous hair loss in 70% or more of the body surface were used as donor mice. The donor mice were euthanized by cervical dislocation, and then the inguinal, axilla, and auricular lymph nodes were aseptically removed. The lymph nodes were filtered through a 70 μm cell strainer to isolate lymphocytes. The lymphocytes were washed with Advanced RPMI media (containing 10% fetal bovine serum, 2 mM Gluta Max, and 100 U/mL penicillin streptomycin), and then suspended in Advanced RPMI media to which Human rIL-2 (Roche; final concentration of 30 U/mL), Mouse rIL-7 (R&D systems, Inc.; final concentration of 25 ng/mL), and Mouse rIL-15 (R&D systems, Inc.; final concentration of 50 ng/mL) were added so that the concentration was $2 \times 10^6$ cells/mL. The lymphocytes were seeded in 1 mL portions on 24-well plates, and 500 μL of Dynabead mouse T-activator CD3/CD28 (Life Technologies) was added, followed by culture in a $CO_2$ incubator. Culture was performed for 6 days so that the cell density was 1.5 to $2.0 \times 10^6$ cells/mL during culture.

The day of transplantation of lymphocytes derived from donor mice was regarded as Day 0. Two days before the day of transplantation (Day −2), hair on the back, which would be a transplantation site, of 10-week old female C3H/HeJ mice without hair loss (CLEA Japan, Inc.) was removed with an electric hair clipper under isoflurane anesthesia (1.5 cm×1.5 cm). Furthermore, grouping was performed using the body weight on Day −1 as an index.

On Day 0, lymphocytes in which beads were removed with EasySep magnet (Stemcell Technologies Inc.) were collected into new tubes. The collected lymphocytes were suspended in PBS(−) so that the concentration was $10 \times 10^7$ cells/mL, filled in a 1 mL syringe with a 26G injection needle, and stored on ice until transplantation. Under isoflurane anesthesia, the filled lymphocyte suspension was intradermally injected into the hair removal site in 100 μL/body portions. PBS(−) was intradermally administered in 100 μL/body portions to mice without transplantation of lymphocytes. Mice without transplantation of lymphocytes were regarded as the normal group. Mice with and without transplantation of lymphocytes were maintained on a low-fat diet (CR-LPF; Oriental Yeast Co., Ltd.) after Day 0 until Day 49.

On Day 49, grouping was performed using the mouse hair loss score calculated in the same manner as in Example 73 as an index (the hair loss score on Day 49 (mean±standard error): 3.6±0.66). Test compounds were administered to mice with hair loss symptoms at a dose of 10 mg/kg once daily for 42 days from Day 49 to Day 90. The compound of Example 29 and the compound of Example 57 were used as the test compounds. The compound of Example 29 and the compound of Example 57 were orally administered after suspended in a 0.5 w/v % methylcellulose solution. A group in which the compound of Example 29 was administered was regarded as the group of treatment with the compound of Example 29, and a group in which the compound of Example 57 was administered was regarded as the group of treatment with the compound of Example 57. A vehicle (0.5 w/v % methylcellulose solution) of each test compound was administered in the same manner to the normal group and the disease group (vehicle treatment group).

Figure 3:
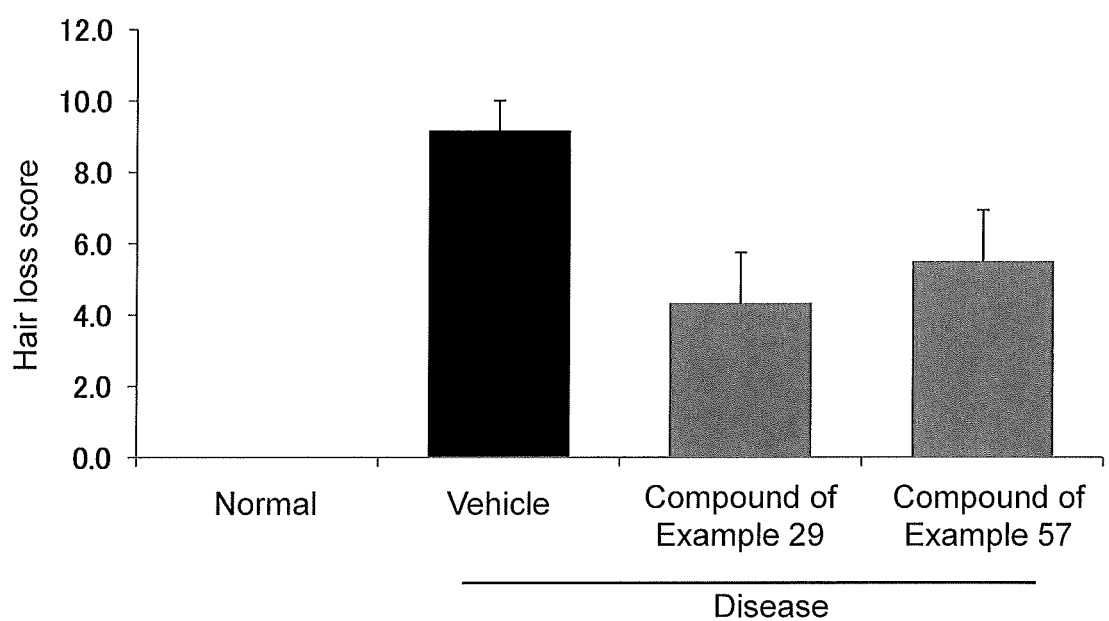
FIG. 3 is a graph showing the suppressing effects by the therapeutic protocol of the compound of Example 29 and the compound of Example 57 on increase in the hair loss score in a mouse alopecia areata model.

On Day 91, the mouse hair loss score was calculated in the same manner as in Example 73. The results are shown in FIG. 3. The vertical axis of FIG. 3 represents the hair loss score (mean±standard error) of each group. On the horizontal axis, "normal" represents the normal group (number of individuals: n=3), "vehicle" represents the disease group (vehicle treatment group) (n=6), "compound of Example 29" represents the group of treatment with the compound of Example 29 (n=6), and "compound of Example 57" represents the group of treatment with the compound of Example 57 (n=6). On Day 91, the hair loss score was remarkably increased in the disease group (vehicle treatment group) (hair loss score: 9.2±0.83) compared with the mean hair loss score (3.6±0.66) on Day 49. This increase in the hair loss score was suppressed by administration of the compound of Example 29 or the compound of Example 57 (the hair loss score of the group of treatment with the compound of Example 29: 4.3±1.41, the hair loss score of the group of treatment with the compound of Example 57: 5.5±1.43).

This result revealed that cyclic amine derivative (I) or a pharmacologically acceptable salt thereof exhibits a remarkable symptom-suppressing effect on hair loss symptoms by the therapeutic protocol.

INDUSTRIAL APPLICABILITY

Our cyclic amine derivative or a pharmacologically acceptable salt thereof remarkably suppresses the worsening of hair loss symptoms in the preventive protocol and the therapeutic protocol in an alopecia areata model, and thus can be utilized as a therapeutic agent or a preventive agent for alopecia areata.

The invention claimed is:

1. A method of treating or preventing alopecia areata, comprising administering to an individual in need thereof a cyclic amine derivative represented by general formula (I) or a pharmacologically acceptable salt thereof as an active ingredient:

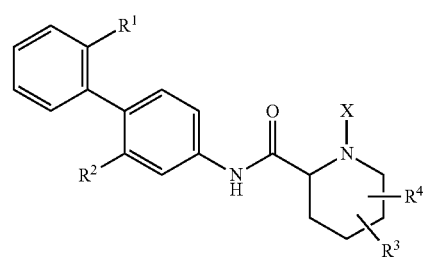

wherein
R¹ represents an alkyloxy group having 1 to 3 carbon atoms, any 1 to 3 hydrogen atoms of which are optionally substituted with a halogen atom(s),
R² represents a halogen atom,
R³ represents a hydrogen atom, a halogen atom, or a hydroxy group,
R⁴ represents a hydrogen atom or a halogen atom,
X represents —C(=O)—(CH₂)ₙ—R⁵ or —S(=O)₂—R⁶,
n represents an integer of 0 to 5,
R⁵ represents a hydrogen atom, —OR⁷, —SR⁷, —S(=O)₂—R⁷, —N(R⁷)R⁸, an alkyl group having 1 to 3 carbon atoms, any 1 to 3 hydrogen atoms of which are optionally substituted with a halogen atom(s), or a heteroaryl group, any hydrogen atom(s) of which is/are optionally substituted with an alkyl group(s) having 1 to 3 carbon atoms,
R⁶ represents an alkyl group having 1 to 5 carbon atoms,
R⁷ represents a hydrogen atom or an alkyl group having 1 to 3 carbon atoms, any 1 to 3 hydrogen atoms of which are optionally substituted with a halogen atom(s), and
R⁸ represents a hydrogen atom, an alkyl group having 1 to 3 carbon atoms, an acyl group having 2 to 4 carbon atoms, or an alkylsulfonyl group having 1 to 3 carbon atoms.

2. The method according to claim 1, wherein
R¹ is an alkyloxy group having 1 to 3 carbon atoms, any 1 to 3 hydrogen atoms of which are optionally substituted with a fluorine atom(s) or a chlorine atom(s),
R² is a fluorine atom or a chlorine atom,
R³ is a hydrogen atom, a fluorine atom, a chlorine atom, or a hydroxy group,
R⁴ is a hydrogen atom, a fluorine atom, or a chlorine atom,
R⁵ is a hydrogen atom, —OR⁷, —SR⁷, —S(=O)₂—R⁷, —C(=O)—OR⁷, —N(R⁷)R⁸, an alkyl group having 1 to 3 carbon atoms, any 1 to 3 hydrogen atoms of which are optionally substituted with a fluorine atom(s) or a chlorine atom(s), or a heteroaryl group, any hydrogen atom(s) of which is/are optionally substituted with a methyl group(s),
R⁶ is an alkyl group having 1 to 3 carbon atoms, and
R⁷ is a hydrogen atom or an alkyl group having 1 to 3 carbon atoms, any 1 to 3 hydrogen atoms of which are optionally substituted with a fluorine atom(s) or a chlorine atom(s).

3. The method according to claim 1, wherein
R¹ is a methoxy group, any 1 to 3 hydrogen atoms of which are optionally substituted with a fluorine atom(s),
R² is a fluorine atom or a chlorine atom,
R³ is a hydrogen atom, a fluorine atom, or a hydroxy group,
R⁴ is a hydrogen atom or a fluorine atom,
n is an integer of 0 to 4,
R⁵ is a hydrogen atom, —OR⁷, —N(R⁷)R⁸, an alkyl group having 1 to 3 carbon atoms, any 1 to 3 hydrogen atoms of which are optionally substituted with a fluorine atom(s), or a 5-membered heteroaryl group, any hydrogen atom(s) of which is/are optionally substituted with a methyl group(s),
R⁶ is a methyl group or an ethyl group,
R⁷ is a hydrogen atom or an alkyl group having 1 to 3 carbon atoms, any 1 to 3 hydrogen atoms of which are optionally substituted with a fluorine atom(s), and
R⁸ is a hydrogen atom, a methyl group, an acyl group having 2 to 4 carbon atoms, or an alkylsulfonyl group having 1 to 3 carbon atoms.

4. The method according to claim 1, wherein
R¹ is a trifluoromethoxy group,
R² is a chlorine atom,
R³ is a hydrogen atom,
R⁴ is a hydrogen atom,
X is —C(=O)—(CH₂)ₙ—R⁵,
n is an integer of 0 to 3,
R⁵ is a methyl group, a trifluoromethyl group, —N(R⁷)R⁸, an imidazolyl, triazolyl, or tetrazolyl group, any hydrogen atom(s) of which is/are optionally substituted with a methyl group(s),
R⁷ is a hydrogen atom, a methyl group, or an ethyl group, and
R⁸ is a hydrogen atom, a methyl group, an acetyl group, a propionyl group, a methylsulfonyl group, or an ethylsulfonyl group.

5. The method according to claim 1, which is a retinoid-related orphan receptor γ antagonist.

6. The method according to claim 2, which is a retinoid-related orphan receptor γ antagonist.

7. The method according to claim 3, which is a retinoid-related orphan receptor γ antagonist.

8. The method according to claim 4, which is a retinoid-related orphan receptor γ antagonist.

* * * * *